United States Patent
Davenport et al.

(10) Patent No.: US 11,976,137 B2
(45) Date of Patent: May 7, 2024

(54) COMPOUNDS FOR USE AS APELIN RECEPTOR ANTAGONISTS

(71) Applicant: Cambridge Enterprise Limited, Cambridge (GB)

(72) Inventors: Anthony Peter Davenport, Bourn (GB); Robert Charles Glen, Suffolk (GB); Janet Julie Maguire, Cambridge (GB)

(73) Assignee: Cambridge Enterprise Limited, Cambridge (GB)

( * ) Notice: Subject to any disclaimer, the term of this patent is extended or adjusted under 35 U.S.C. 154(b) by 0 days.

(21) Appl. No.: 17/044,923

(22) PCT Filed: Apr. 4, 2019

(86) PCT No.: PCT/GB2019/050992
§ 371 (c)(1),
(2) Date: Oct. 2, 2020

(87) PCT Pub. No.: WO2019/193355
PCT Pub. Date: Oct. 10, 2019

(65) Prior Publication Data
US 2021/0155659 A1 May 27, 2021

(30) Foreign Application Priority Data
Apr. 5, 2018 (GB) .................................. 1805675

(51) Int. Cl.
*C07K 7/08* (2006.01)
*A61K 38/00* (2006.01)
(52) U.S. Cl.
CPC ................ *C07K 7/08* (2013.01); *A61K 38/00* (2013.01)
(58) Field of Classification Search
None
See application file for complete search history.

(56) References Cited

FOREIGN PATENT DOCUMENTS

| CN | 105026423 A | | 3/2014 |
| EP | 3 228 630 A1 | | 10/2017 |
| EP | 3228630 | * | 10/2017 |
| WO | 2013/082186 A2 | | 6/2013 |

OTHER PUBLICATIONS

Macaluso et al. (ChemMedChem 2011, 6, 1017-1023) (Year: 2011).*
Harford-Wright et al. (Brain 2017: 140; 2939-2954) (Year: 2017).*
Le Gonidec et al. (FASEB J. Jun. 2017; 31(6): 2507-2519) (Year: 2017).*
Brame et al., 2015, "Design, Characterization, and First-In-Human Study of the Vascular Actions of a Novel Biased Apelin Receptor Agonist" Hypertension, vol. 65, No. 4, pp. 834-840.
Davenport et al., 2009, "Abtract 5787: Discovery and Characterisation of Linear and Cyclic Peptide Agonists of Apelins" 82d Scientific Session of the American-Heart-Association, Cirulation.
Harford-Wright et al., 2017, "Pharmacological targeting of apelin impairs glioblastoma growth" Brain, vol. 140, No. Part 11, pp. 2939-2954.
Kalin et al., 2007, "Paracrine and autocrine mechanisms of apelin signaling govern embryonic and tumor angiogenesis" Development Biology 3055, pp. 599-614.
Le Gonidec et al., 2017, "Protamine is an antagonist of apelin receptor, and its activity is reversed by heparin" The FASEB Journal, 31, 2507-2519.
Lee et al., 2005, "Modification of the Terminal Residue of Apelin-13 Antagonizes Its Hypotensive Action" Endocrinology 146(1):231-236.
Macaluso et al., 2011, "Discovery of a Competitive Apelin Receptor (APJ) Antagonist" ChemMedChem 6, 1017-1023.
Maloney et al., 2012, "Discovery of 4-oxo-6((pyrimidin-2-ylthio)methyl)-4H-phyran-3-yl-4-nitrobenzoate (ML221) as a functional antagonist of the apelin (APJ) receptor" Bioorganic & Medicinal Chemistry Letters 22, pp. 6656-6660.
Maloney et al., 2011, "Functional antagonists of the Apelin (APJ) receptor," from Probe Reports from the NIH Molecular Libraries Program, accessed from www.ncbi.nlm.nih.gov/books/NBK133430.
Masri et al., 2010, REG PEP 2010 Platform Abstracts, Regulatory Peptides, 164, 26-34.
O'Dowd et al., 1993, "A human gene that shows identity with the gene encoding the angiotensin receptor is located on chromosome 11" Gene, 136, pp. 355-360.
Pitkin et al., 2010, "International Union of Basic and Clinical Pharmacology. LXXIV. Apelin Receptor Nomenclature, Distribution, Pharmacology and Function" Pharmacological Reviews, vol. 62, No. 3, pp. 331-342.
Sorli et al., 2007, "Apelin is a potent activator of tumor neoangiogenesis" Oncogene, 26, pp. 7692-7699.

(Continued)

*Primary Examiner* — Sergio Coffa
(74) *Attorney, Agent, or Firm* — Biospark Intellectual Property Law

(57) ABSTRACT

The present invention relates to synthetic polypeptide compounds which bind to a class A G-protein-coupled receptor, the Apelin receptor. These compounds may act as apelin receptor antagonists. These compounds and compositions comprising them may be useful in the treatment of diseases, such as cancer.

10 Claims, 4 Drawing Sheets
Specification includes a Sequence Listing.

(56) References Cited

OTHER PUBLICATIONS

Tatemoto et al., 1998, "Isolation and Characterization of a Novel Endogenous Peptide Ligand for the Human APJ Receptor" Biochemical and Biophysical Research Communications, 251, pp. 471-476.

Yang et al., 2016, "Apelin/APJ system and cancer" Clinica Chimica Acta, 457, 112-116.

International Search Report of the International Searching Authority for International Application No. PCT/GB2019/050992, dated Jul. 17, 2019.

* cited by examiner

SEQUENCE LISTING

```
<160> NUMBER OF SEQ ID NOS: 17

<210> SEQ ID NO 1
<211> LENGTH: 13
<212> TYPE: PRT
<213> ORGANISM: Unknown
<220> FEATURE:
<223> OTHER INFORMATION: Description of Unknown:
      Apelin sequence
<220> FEATURE:
<221> NAME/KEY: MOD_RES
<222> LOCATION: (1)..(1)
<223> OTHER INFORMATION: Pyrrolidone carboxylic acid

<400> SEQUENCE: 1

Glu Arg Pro Arg Leu Ser His Lys Gly Pro Met Pro Phe
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(6)
<223> OTHER INFORMATION: Disulphide bond between Cys residues
<220> FEATURE:
<221> NAME/KEY: SITE
<222> LOCATION: (9)..(14)
<223> OTHER INFORMATION: Disulphide bond between Cys residues

<400> SEQUENCE: 2

Cys Arg Pro Arg Leu Cys Lys His Cys Arg Pro Arg Leu Cys
1               5                   10
```

-continued

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Cys Arg Pro Arg Leu Cys His Lys Cys Arg Pro Arg Leu Cys
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Arg Pro Arg Leu Cys Lys His Cys Arg Pro Arg Leu Cys
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (11)..(11)
<223> OTHER INFORMATION: 2-Aminoisobutyric acid
<220> FEATURE:
<221> NAME/KEY: MOD_RES
<222> LOCATION: (13)..(13)
<223> OTHER INFORMATION: Norleucine
<220> FEATURE:
<221> NAME/KEY: MOD_RES
<222> LOCATION: (14)..(14)
<223> OTHER INFORMATION: 3,4,5-trifluorophenyl-L-alanine

<400> SEQUENCE: 5

Cys Arg Pro Arg Leu Cys Lys His Cys Arg Xaa Arg Leu Phe
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (11)..(11)
<223> OTHER INFORMATION: 2-Aminoisobutyric acid
<220> FEATURE:
<221> NAME/KEY: MOD_RES
<222> LOCATION: (13)..(13)
<223> OTHER INFORMATION: Norleucine

```
<220> FEATURE:
<221> NAME/KEY: MOD_RES
<222> LOCATION: (14)..(14)
<223> OTHER INFORMATION: 3,4,5-trifluorophenyl-L-alanine

<400> SEQUENCE: 6

Gln Arg Pro Arg Leu Cys Lys His Cys Arg Xaa Arg Leu Phe
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pyrrolidone carboxylic acid
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (11)..(11)
<223> OTHER INFORMATION: 2-Aminoisobutyric acid
<220> FEATURE:
<221> NAME/KEY: MOD_RES
<222> LOCATION: (13)..(13)
<223> OTHER INFORMATION: Norleucine
<220> FEATURE:
<221> NAME/KEY: MOD_RES
<222> LOCATION: (14)..(14)
<223> OTHER INFORMATION: 3,4,5-trifluorophenyl-L-alanine

<400> SEQUENCE: 7

Glu Arg Pro Arg Leu Cys Lys His Cys Arg Xaa Arg Leu Phe
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (6)..(6)
<223> OTHER INFORMATION: (S)-2-Aminobutyric acid
<220> FEATURE:
<221> NAME/KEY: MOD_RES
<222> LOCATION: (11)..(11)
<223> OTHER INFORMATION: 2-Aminoisobutyric acid
<220> FEATURE:
<221> NAME/KEY: MOD_RES
<222> LOCATION: (13)..(13)
<223> OTHER INFORMATION: Norleucine
<220> FEATURE:
<221> NAME/KEY: MOD_RES
<222> LOCATION: (14)..(14)
<223> OTHER INFORMATION: 3,4,5-trifluorophenyl-L-alanine

<400> SEQUENCE: 8

Cys Arg Pro Arg Leu Xaa Lys His Cys Arg Xaa Arg Leu Phe
1               5                   10
```

-continued

```
<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (9)..(9)
<223> OTHER INFORMATION: (S)-2-Aminobutyric acid
<220> FEATURE:
<221> NAME/KEY: MOD_RES
<222> LOCATION: (11)..(11)
<223> OTHER INFORMATION: 2-Aminobutyric acid
<220> FEATURE:
<221> NAME/KEY: MOD_RES
<222> LOCATION: (13)..(13)
<223> OTHER INFORMATION: Norleucine
<220> FEATURE:
<221> NAME/KEY: MOD_RES
<222> LOCATION: (14)..(14)
<223> OTHER INFORMATION: 3,4,5-trifluorophenyl-L-alanine

<400> SEQUENCE: 9

Cys Arg Pro Arg Leu Cys Lys His Xaa Arg Xaa Arg Leu Phe
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Myristate
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (11)..(11)
<223> OTHER INFORMATION: 2-Aminoisobutyric acid
<220> FEATURE:
<221> NAME/KEY: MOD_RES
<222> LOCATION: (13)..(13)
<223> OTHER INFORMATION: Norleucine
<220> FEATURE:
<221> NAME/KEY: MOD_RES
<222> LOCATION: (14)..(14)
<223> OTHER INFORMATION: 3,4,5-trifluorophenyl-L-alanine

<400> SEQUENCE: 10

Cys Arg Pro Arg Leu Cys Lys His Cys Arg Xaa Arg Leu Phe
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pyrrolidone carboxylic acid
<220> FEATURE:
<221> NAME/KEY: MOD_RES
```

```
<222> LOCATION: (5)..(5)
<223> OTHER INFORMATION: Norleucine
<220> FEATURE:
<221> NAME/KEY: MOD_RES
<222> LOCATION: (6)..(6)
<223> OTHER INFORMATION: (S)-2-Aminobutyric acid
<220> FEATURE:
<221> NAME/KEY: MOD_RES
<222> LOCATION: (9)..(9)
<223> OTHER INFORMATION: (S)-2-Aminobutyric acid
<220> FEATURE:
<221> NAME/KEY: MOD_RES
<222> LOCATION: (11)..(11)
<223> OTHER INFORMATION: 2-Aminoisobutyric acid
<220> FEATURE:
<221> NAME/KEY: MOD_RES
<222> LOCATION: (13)..(13)
<223> OTHER INFORMATION: Norleucine
<220> FEATURE:
<221> NAME/KEY: MOD_RES
<222> LOCATION: (14)..(14)
<223> OTHER INFORMATION: 3,4,5-trifluorophenyl-L-alanine

<400> SEQUENCE: 11

Glu Arg Pro Arg Leu Xaa Lys His Xaa Arg Xaa Arg Leu Phe
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (11)..(11)
<223> OTHER INFORMATION: 2-Aminoisobutyric acid
<220> FEATURE:
<221> NAME/KEY: MOD_RES
<222> LOCATION: (13)..(13)
<223> OTHER INFORMATION: Norleucine
<220> FEATURE:
<221> NAME/KEY: MOD_RES
<222> LOCATION: (14)..(14)
<223> OTHER INFORMATION: 3,4,5-trifluorophenyl-L-alanine

<400> SEQUENCE: 12

Cys Arg Pro Arg Leu Cys His Lys Cys Arg Xaa Arg Leu Phe
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (9)..(9)
<223> OTHER INFORMATION: 2-Aminobutyric acid
<220> FEATURE:
<221> NAME/KEY: MOD_RES
<222> LOCATION: (11)..(11)
<223> OTHER INFORMATION: 2-Aminoisobutyric acid
<220> FEATURE:
```

```
<221> NAME/KEY: MOD_RES
<222> LOCATION: (13)..(13)
<223> OTHER INFORMATION: Norleucine
<220> FEATURE:
<221> NAME/KEY: MOD_RES
<222> LOCATION: (14)..(14)
<223> OTHER INFORMATION: 3,4,5-trifluorophenyl-L-alanine

<400> SEQUENCE: 13

Ala Arg Pro Arg Leu Cys Lys His Xaa Arg Xaa Arg Leu Phe
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylation
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (9)..(9)
<223> OTHER INFORMATION: 2-Aminobutyric acid
<220> FEATURE:
<221> NAME/KEY: MOD_RES
<222> LOCATION: (11)..(11)
<223> OTHER INFORMATION: (S)-2-Aminobutyric acid
<220> FEATURE:
<221> NAME/KEY: MOD_RES
<222> LOCATION: (13)..(13)
<223> OTHER INFORMATION: Norleucine
<220> FEATURE:
<221> NAME/KEY: MOD_RES
<222> LOCATION: (14)..(14)
<223> OTHER INFORMATION: 3,4,5-trifluorophenyl-L-alanine

<400> SEQUENCE: 14

Ala Arg Pro Arg Leu Cys Lys His Xaa Arg Xaa Arg Leu Phe
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (6)..(6)
<223> OTHER INFORMATION: (S)-2-Aminobutyric acid
<220> FEATURE:
<221> NAME/KEY: MOD_RES
<222> LOCATION: (9)..(9)
<223> OTHER INFORMATION: (S)-2-Aminobutyric acid
<220> FEATURE:
<221> NAME/KEY: MOD_RES
<222> LOCATION: (11)..(11)
<223> OTHER INFORMATION: 2-Aminoisobutyric acid
<220> FEATURE:
<221> NAME/KEY: MOD_RES
<222> LOCATION: (13)..(13)
<223> OTHER INFORMATION: Norleucine
<220> FEATURE:
<221> NAME/KEY: MOD_RES
```

```
<222> LOCATION: (14)..(14)
<223> OTHER INFORMATION: 3,4,5-trifluorophenyl-L-alanine

<400> SEQUENCE: 15

Ala Arg Pro Arg Leu Xaa Lys His Xaa Arg Xaa Arg Leu Phe
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Myristate
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (6)..(6)
<223> OTHER INFORMATION: (S)-2-Aminobutyric acid
<220> FEATURE:
<221> NAME/KEY: MOD_RES
<222> LOCATION: (9)..(9)
<223> OTHER INFORMATION: (S)-2-Aminobutyric acid
<220> FEATURE:
<221> NAME/KEY: MOD_RES
<222> LOCATION: (11)..(11)
<223> OTHER INFORMATION: 2-Aminoisobutyric acid
<220> FEATURE:
<221> NAME/KEY: MOD_RES
<222> LOCATION: (13)..(13)
<223> OTHER INFORMATION: Norleucine
<220> FEATURE:
<221> NAME/KEY: MOD_RES
<222> LOCATION: (14)..(14)
<223> OTHER INFORMATION: 3,4,5-trifluorophenyl-L-alanine

<400> SEQUENCE: 16

Ala Arg Pro Arg Leu Xaa Lys His Xaa Arg Xaa Arg Leu Phe
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Myristate
<220> FEATURE:
<221> NAME/KEY: MOD_RES
<222> LOCATION: (5)..(5)
<223> OTHER INFORMATION: Norleucine
<220> FEATURE:
<221> NAME/KEY: MOD_RES
<222> LOCATION: (6)..(6)
<223> OTHER INFORMATION: (S)-2-Aminobutyric acid
<220> FEATURE:
<221> NAME/KEY: MOD_RES
<222> LOCATION: (9)..(9)
<223> OTHER INFORMATION: (S)-2-Aminobutyric acid
<220> FEATURE:
<221> NAME/KEY: MOD_RES
<222> LOCATION: (11)..(11)
<223> OTHER INFORMATION: 2-Aminoisobutyric acid
<220> FEATURE:
<221> NAME/KEY: MOD_RES
<222> LOCATION: (13)..(13)
<223> OTHER INFORMATION: Norleucine
<220> FEATURE:
```

```
<221> NAME/KEY: MOD_RES
<222> LOCATION: (14)..(14)
<223> OTHER INFORMATION: 3,4,5-trifluorophenyl-L-alanine

<400> SEQUENCE: 17

Ala Arg Pro Arg Leu Xaa His Lys Xaa Arg Xaa Arg Leu Phe
1               5                   10
```

COMPOUNDS FOR USE AS APELIN RECEPTOR ANTAGONISTS

FIELD OF THE INVENTION

The present invention relates to compounds and compositions having apelin receptor antagonist activity which may be useful in the treatment of conditions such as cancer.

BACKGROUND OF THE INVENTION

Apelin

The apelin receptor, a class A GPCR first identified in 1993 [1] remained an orphan until the identification of apelin as the cognate ligand in 1998 [2]. Endogenous apelin peptides are derived from the C terminus of the 77 amino acid precursor pre-proapelin. Proteolytic cleavage suggests that apelin-17, apelin-13 and [Pyr¹]apelin-13 are the most biologically relevant. In human heart [3] and plasma [4], [Pyr¹]apelin-13 (Pyr1-RPRLSHKGPMPF) was the predominant isoform detected.

Apelin responses are consistent with coupling via Gαi and via a G protein independent manner through recruitment of β-arrestin, a protein that initiates receptor internalisation as well as downstream signalling [5].

Apelin is vitally important in many homeostatic and signalling processes e.g. in the control of blood pressure and angiogenesis in the cardiovascular system, as a co-receptor for HIV and for modulation of metabolic and homeostatic processes throughout the body [6, 7].

Remarkably, a recently discovered alternative apelin peptide agonist, Elabela/Toddler [8, 9](ELA), also acts through the apelin receptor and is critical in the development of the heart [8], despite having little sequence homology to the established ligand apelin. The APELA gene expresses a 54-amino acid protein comprising a 32-amino-acid mature peptide (ELA-32). Degradation products result in active peptides ELA-21 (LRKHNCLQRRCMPLHSRVPFP), and ELA-11.

Apelin has been reported to be a multifactorial agent in a number of disease processes including e.g. diabetes, cardiovascular disease, infection by HIV, kidney disease, angiogenesis. [10-22].

Apelin has been implicated in the aetiology of a number of different sub-types of cancer [refs. Cancer 23-53, US 20140005181 A1]. Recent work has identified apelin as a sustaining endocrine factor in glioblastoma [60].

Apelin Receptor Antagonists

A number of recent patents have been filed around apelin receptor antagonists. A putative mechanism was claimed for apelin receptor antagonists as a target for cancer (US2017146518 (A1)). A combination of an apelin receptor antagonist and an angiogenesis inhibitor (WO2017/174758) has been claimed to reduce or overcome resistance to anti-angiogenic therapy. A functional antagonist (apelin-13 (F13A)) and apelin receptor antagonists have been reported. [54-60].

For human apelin receptors in vitro, Apelin-13(F13A) exhibits binding, calcium mobilisation and internalisation responses similar to (Pyr1)apelin-13, while in human cardiac tissue, F13A competes for binding with [125I]-(Pyr1) apelin-13 in the left ventricle and effectively constricts endothelium-denuded saphenous vein. Therefore, although apelin-13(F13A) has been reported to act as a functional antagonist, it may in fact act as an apelin receptor agonist in-vitro. [15]

MM54 [cyclo(1-6)CRPRLC-KH-cyclo(9-14)CRPRLC is a competitive macrocyclic apelin receptor antagonist [57]. MM54 showed anti-tumor properties in glioblastoma. In addition, the combination of MM54 with the anti-cancer compound tomozolomide showed synergistic properties [60] in a model of glioblastoma. The pharmacology of MM54 shows binding affinity of 82 nM in apelin expressing hCHO cells, binding to human left ventricle (Kd) of 358 nM and MM54 is an antagonist, pA2=6.63, in the DRx β-Arrestin assay. However, MM54 showed weak agonist activity (pD2=of 5.86, EC50=1.40 μM) in the DRx cAMP assay. In human forearm studies, MM54 unexpectedly showed functional agonist activity indicated by vasodilation. For this reason, there may be additional effects associated with this pharmacological profile including reduction in blood pressure mediated by apelin signalling via cAMP. In addition, there is an increased complexity and cost associated with synthesis of macrocyclic analogs.

Unexpectedly, linear peptide analogs of MM54 were observed to exhibit apelin receptor antagonism. MM107, the linear sequence of MM54, CRPRLCKHCRPRLC, shows binding affinity of 180 nM in apelin receptor expressing hCHO cells, and is an antagonist ($pA_2$=7.03) in the DRx β-Arrestin assay, but surprisingly, and unlike MM54, showed no agonist effects at 100 μM in the DRx cAMP assay. Further modification of the linear structure resulted in the identification of antagonists at the apelin receptor that displayed higher affinity, increased antagonism of apelin receptors in both DRx β-Arrestin and DRx cAMP assays with no evidence of apelin receptor agonist effects. The linear apelin antagonist MM193 also showed significant anti-cancer effects [60] in models of glioblastoma.

SUMMARY OF THE INVENTION

The present inventors have discovered a number of linear peptides which are capable of acting as competitive apelin receptor antagonists. These include compounds that are more potent antagonists than the known macrocyclic apelin receptor antagonist MM54 and have an improved pharmacology profile.

In one aspect the present invention provides compounds comprising the sequence of Formula I:

$$(R^1\text{-}L_c)\text{-}X^1\text{-}L_1\text{-}X^2\text{-}L_2\text{-}X^3\text{-}L_3\text{-}X^4\text{-}L_4\text{-}X^5\text{-}L_5\text{-}X^6\text{-}L_6\text{-}X^7\text{-}L_7\text{-}X^8\text{-}L_8\text{-}X^9\text{-}L_9\text{-}X^{10}\text{-}L_{10}\text{-}X^{11}\text{-}L_{11}\text{-}X^{12}\text{-}L_{12}\text{-}X^{13}\text{-}L_{13}\text{-}X^{14}(\text{-}L_c\text{-}R^2)$$ (Formula I)

wherein $X^1$ may be any amino acid;

$X^2$ may be selected from the group consisting of R, H, and K;

$X^3$ is P;

$X^4$ is R;

$X^5$ may be selected from the group consisting of Nle, L, A, V, I, M, F, Y, and W;

$X^6$ may be selected from the group consisting of Abu, C, A, V, I, L, M, F, Y, W, and P;

$X^7$ may be selected from the group consisting of H, K, A, V, I, L, M, F, Y, W, and R;

$X^8$ may be selected from the group consisting of K, H, A, V, I, L, M, F, Y, W, and R;

$X^9$ may be selected from the group consisting of Abu, C, A, V, I, L, M, F, Y, W, and P;

$X^{10}$ may be selected from the group consisting of R, H, and K;

$X^{11}$ may be selected from the group consisting of Aib, and P;

$X^{12}$ may be selected from the group consisting of R, H, and K;

$X^{13}$ may be selected from the group consisting of Nle, Aib, L, V, I, and A;

$X^{14}$ may be selected from the group consisting of none, C, F, other hydrophobic amino acids (including Alanine (A), Isoleucine (I), Leucine (L), Methionine (M), Tyrosine (Y), Tryptophan (W), Valine (V), Proline (P), Glycine (G)), and $X^{14}$ may specifically be one of 3,4,5-trifluorophenylalanine (Tfpa or (3,4,5-trifluoro) F), β-cyclohexylalanine (Cha), Naphthylalanine (Nal), 4-chlorophenylalanine (4cpa), 4-methoxyphenylalanine, 4-methylphenylalanine, 4-pyridylealanine, 3-pyridylalanine, 2-pyridylalanine, D-(-)-α-phenylglycine, homophenylalanine, 3-styrylalanine, O-benzyl-L-tyrosine, 4-benzoyl-L-phenylalanine, α-methyl-L-phenylalanine, α-methyl-D-phenylalanine, aminoindane, 2-aminoindane, O-benzyltyrosine, or 4-Aminopiperidine-4-carboxylic acid;

wherein:

1) for $X^1$ to $X^{14}$ any natural amino acid listed may independently be optionally modified, and wherein 2) for $X^1$ to $X^{14}$ any modified amino acid listed may independently be optionally further modified and, in options 1) and 2), the modification in option 1) and the further modification in option 2) is optionally alkylation, esterification, N-alkyl amidation, substitution of hydrogen with any halo group or hydroxyl group or conjugation to an $R^3$ moiety through a conjugation linker $L_c$;

each of $L_1$ to $L_{13}$ may be independently a linkage appropriate for joining two amino acids together, such as an amide bond, N-methylated amide, urea, ester, carbamate, peptoid, sulphonamide, alkene, thioamide, thioether, fluoroalkene, azapeptide difluoroketone or epoxide;

$R^1$, $R^2$, and $R^3$ may be independently absent or independently represent the rest of the compound, for example $R^1$, $R^2$, and $R^3$ can independently be a peptide, an acetyl (Ac), formyl, propinyl, biotin, myristoyl, or palmitoyl moiety, a methyl moiety, a saturated or unsaturated fatty acyl moiety, a polyethylene glycol polymer moiety, an immunoglobulin moiety, an immunoglobulin Fc domain moiety, albumin, a methylated moiety, an esterified moiety, or a portion of the natural apelin compound;

each $L_c$ may be independently absent or is a conjugation linker which joins $R^1$ to $X^1$, $R^2$ to $X^{14}$, or an $R^3$ moiety to any of $X^1$ to $X^{14}$ may be is selected from any linkage appropriate for joining $R^1$ to $X^1$, $R^2$ to $X^{14}$ or an $R^3$ moiety to any of $X^1$ to $X^{14}$;

or a pharmaceutically acceptable salt, solvate, amide, ester, prodrug, or deuterated analogue thereof.

In one aspect the present invention provides compounds comprising the sequence of Formula I:

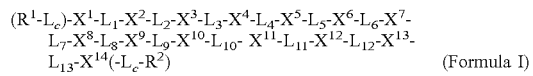

(Formula I)

wherein $X^1$ may be any amino acid;

$X^2$ may be selected from the group consisting of R, H, and K;

$X^3$ is P;

$X^4$ is R;

$X^5$ may be selected from the group consisting of Nle, L, A, V, I, M, F, Y, and W;

$X^6$ may be selected from the group consisting of Abu, C, A, V, I, L, M, F, Y, W, and P;

$X^7$ may be selected from the group consisting of H, K, A, V, I, L, M, F, Y, W, and R;

$X^8$ may be selected from the group consisting of K, H, A, V, I, L, M, F, Y, W, and R;

$X^9$ may be selected from the group consisting of Abu, C, A, V, I, L, M, F, Y, W, and P;

$X^{10}$ may be selected from the group consisting of R, H, and K;

$X^{11}$ may be selected from the group consisting of Aib, and P;

$X^{12}$ may be selected from the group consisting of R, H, and K;

$X^{13}$ may be selected from the group consisting of Nle, Aib, L, V, I, and A;

$X^{14}$ may be selected from the group consisting of C, F, other hydrophobic amino acids (including Alanine (A), Isoleucine (I), Leucine (L), Methionine (M), Tyrosine (Y), Tryptophan (W), Valine (V), Proline (P), Glycine (G)), and $X^{14}$ may specifically be one of 3,4,5-trifluorophenylalanine (Tfpa or (3,4,5-trifluoro)F), β-cyclohexylalanine (Cha), Naphthylalanine (Nal), 4-chlorophenylalanine (4cpa), 4-methoxyphenylalanine, 4-methylphenylalanine, 4-pyridylealanine, 3-pyridylalanine, 2-pyridylalanine, D-(-)-α-phenylglycine, homophenylalanine, 3-styrylalanine, O-benzyl-L-tyrosine, 4-benzoyl-L-phenylalanine, α-methyl-L-phenylalanine, α-methyl-D-phenylalanine or aminoindane;

wherein:

1) for $X^1$ to $X^{14}$ any natural amino acid listed may independently be optionally modified, and wherein 2) for $X^1$ to $X^{14}$ any modified amino acid listed may independently be optionally further modified and, in options 1) and 2), the modification in option 1) and the further modification in option 2) is optionally alkylation, esterification, N-alkyl amidation, substitution of hydrogen with any halo group or hydroxyl group or conjugation to an $R^3$ moiety through a conjugation linker $L_c$;

each of $L_1$ to $L_{13}$ may be independently a linkage appropriate for joining two amino acids together, such as an amide bond, N-methylated amide, urea, ester, carbamate, peptoid, sulphonamide, alkene, thioamide, thioether, fluoroalkene, azapeptide difluoroketone or epoxide;

$R^1$, $R^2$, and $R^3$ may be independently absent or independently represent the rest of the compound, for example $R^1$, $R^2$, and $R^3$ can independently be a peptide, an acetyl (Ac), formyl, propinyl, biotin, myristoyl, or palmitoyl moiety, a methyl moiety, a saturated or unsaturated fatty acyl moiety, a polyethylene glycol polymer moiety, an immunoglobulin moiety, an immunoglobulin Fc domain moiety, albumin, a methylated moiety, an esterified moiety, or a portion of the natural apelin compound;

each $L_c$ may be independently absent or is a conjugation linker which joins $R^1$ to $X^1$, $R^2$ to $X^{14}$, or an $R^3$ moiety to any of $X^1$ to $X^{14}$ may be is selected from any linkage appropriate for joining $R^1$ to $X^1$, $R^2$ to $X^{14}$ or an $R^3$ moiety to any of $X^1$ to $X^{14}$;

or a pharmaceutically acceptable salt, solvate, amide, ester, prodrug, or deuterated analogue thereof.

In one aspect the present invention provides compounds comprising the sequence of Formula I:

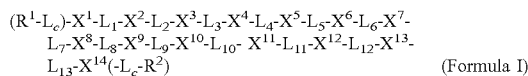 (Formula I)

wherein
$X^1$ is selected from the group consisting of V, I, L, M, P, Y, W, C, Q, Glp, and A;
$X^2$ is R;
$X^3$ is P;
$X^4$ is R;
$X^5$ is selected from the group consisting of A, V, I, Nle, and L;
$X^6$ is selected from the group consisting of Abu, M, P, and C;
$X^7$ is selected from the group consisting of H, R, and K;
$X^8$ is selected from the group consisting of R, K, and H;
$X^9$ is selected from the group consisting of Abu, M, P, and C;
$X^{10}$ is R, or K;
$X^{11}$ is selected from the group consisting of Aib, and P;
$X^{12}$ is R, K, or H;
$X^{13}$ is selected from the group consisting of A, V, I, Nle, and L;
$X^{14}$ is selected from the group consisting of none, C, F, other hydrophobic amino acids (including Alanine (A), Isoleucine (I), Leucine (L), Methionine (M), Tyrosine (Y), Tryptophan (W), Valine (V), Proline (P), Glycine (G)), and $X^{14}$ may specifically be one of 3,4,5-trifluorophenylalanine (Tfpa or (3,4,5-trifluoro)F), β-cyclohexylalanine (Cha), Naphthylalanine (Nal), 4-chlorophenylalanine (4cpa), 4-methoxyphenylalanine, 4-methylphenylalanine, 4-pyridylealanine, 3-pyridylalanine, 2-pyridylalanine, D-(−)-α-phenylglycine, homophenylalanine, 3-styrylalanine, O-benzyl-L-tyrosine, 4-benzoyl-L-phenylalanine, α-methyl-L-phenylalanine, α-methyl-D-phenylalanine, aminoindane, 2-aminoindane, O-benzyltyrosine, or 4-Aminopiperidine-4-carboxylic acid;
wherein:
1) for $X^1$ to $X^{14}$ any natural amino acid listed may independently be optionally modified, and wherein 2) for $X^1$ to $X^{14}$ any modified amino acid listed may independently be optionally further modified and, in options 1) and 2), the modification in option 1) and the further modification in option 2) is optionally alkylation, esterification, N-alkyl amidation, substitution of hydrogen with any halo group or hydroxyl group or conjugation to an $R^3$ moiety through a conjugation linker $L_c$;
each of $L_1$ to $L_{13}$ is independently a linkage appropriate for joining two amino acids together, such as an amide bond, N-methylated amide, urea, ester, carbamate, peptoid, sulphonamide, alkene, thioamide, thioether, fluoroalkene, azapeptide difluoroketone or epoxide;
$R^1$, $R^2$, and $R^3$ are independently absent or independently represent the rest of the compound, for example $R^1$, $R^2$, and $R^3$ can independently be a peptide, an acetyl, formyl, propinyl, biotin, myristoyl, or palmitoyl moiety, a methyl moiety, a saturated or unsaturated fatty acyl moiety, a polyethylene glycol polymer moiety, an immunoglobulin moiety, an immunoglobulin Fc domain moiety, albumin, a methylated moiety, an esterified moiety, or a portion of the natural apelin compound;
each $L_c$ is independently absent or is a conjugation linker which joins $R^1$ to $X^1$, $R^2$ to $X^{14}$, or an $R^3$ moiety to any of $X^1$ to $X^{14}$ and is selected from any linkage appropriate for joining $R^1$ to $X^1$, $R^2$ to $X^{14}$ or an $R^3$ moiety to any of $X^1$ to $X^{14}$;
or a pharmaceutically acceptable salt, solvate, amide, ester, prodrug, or deuterated analogue thereof.

In one aspect the present invention provides compounds comprising the sequence of Formula I:

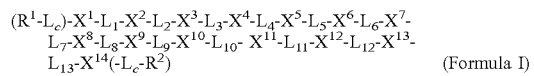 (Formula I)

wherein
$X^1$ is selected from the group consisting of V, I, L, M, P, Y, W, C, Q, Glp, and A;
$X^2$ is R;
$X^3$ is P;
$X^4$ is R;
$X^5$ is selected from the group consisting of A, V, I, Nle, and L;
$X^6$ is selected from the group consisting of Abu, M, P, and C;
$X^7$ is selected from the group consisting of H, R, and K;
$X^8$ is selected from the group consisting of R, K, and H;
$X^9$ is selected from the group consisting of Abu, M, P, and C;
$X^{10}$ is R, or K;
$X^{11}$ is selected from the group consisting of Aib, and P;
$X^{12}$ is R, K, or H;
$X^{13}$ is selected from the group consisting of A, V, I, Nle, and L;
$X^{14}$ is selected from the group consisting of C, F, other hydrophobic amino acids (including Alanine (A), Isoleucine (I), Leucine (L), Methionine (M), Tyrosine (Y), Tryptophan (W), Valine (V), Proline (P), Glycine (G)), and $X^{14}$ may specifically be one of 3,4,5-trifluorophenylalanine (Tfpa or (3,4,5-trifluoro)F), β-cyclohexylalanine (Cha), Naphthylalanine (Nal), 4-chlorophenylalanine (4cpa), 4-methoxyphenylalanine, 4-methylphenylalanine, 4-pyridylealanine, 3-pyridylalanine, 2-pyridylalanine, D-(−)-α-phenylglycine, homophenylalanine, 3-styrylalanine, O-benzyl-L-tyrosine, 4-benzoyl-L-phenylalanine, α-methyl-L-phenylalanine, α-methyl-D-phenylalanine or aminoindane;
wherein:
1) for $X^1$ to $X^{14}$ any natural amino acid listed may independently be optionally modified, and wherein 2) for $X^1$ to $X^{14}$ any modified amino acid listed may independently be optionally further modified and, in options 1) and 2), the modification in option 1) and the further modification in option 2) is optionally alkylation, esterification, N-alkyl amidation, substitution of hydrogen with any halo group or hydroxyl group or conjugation to an $R^3$ moiety through a conjugation linker $L_c$;
each of $L_1$ to $L_{13}$ is independently a linkage appropriate for joining two amino acids together, such as an amide bond, N-methylated amide, urea, ester, carbamate, peptoid, sulphonamide, alkene, thioamide, thioether, fluoroalkene, azapeptide difluoroketone or epoxide;
$R^1$, $R^2$, and $R^3$ are independently absent or independently represent the rest of the compound, for example $R^1$, $R^2$, and $R^3$ can independently be a peptide, an acetyl, formyl, propinyl, biotin, myristoyl, or palmitoyl moiety, a methyl moiety, a saturated or unsaturated fatty acyl moiety, a polyethylene glycol polymer moiety, an immunoglobulin moiety, an immunoglobulin Fc domain moiety, albumin, a methylated moiety, an esterified moiety, or a portion of the natural apelin compound;

each $L_c$ is independently absent or is a conjugation linker which joins $R^1$ to $X^1$, $R^2$ to $X^{14}$, or an $R^3$ moiety to any of $X^1$ to $X^{14}$ and is selected from any linkage appropriate for joining $R^1$ to $X^1$, $R^2$ to $X^{14}$ or an $R^3$ moiety to any of $X^1$ to $X^{14}$;

or a pharmaceutically acceptable salt, solvate, amide, ester, prodrug, or deuterated analogue thereof.

In one aspect the present invention provides compounds that are apelin receptor antagonists.

In one aspect the present invention provides compounds that are apelin receptor ligands.

In one aspect the present invention provides a pharmaceutical composition comprising a compound and a pharmaceutically acceptable diluent, excipient, or carrier.

In one aspect the present invention provides a compound or composition for use in a medicine.

In one aspect the present invention provides a method of treating disease or disorder in a patient, said method comprising administering a compound or a composition of the invention to said patient.

In one aspect the present invention provides a compound or composition for use in the treatment of a disorder or disease selected from the group consisting of a tumor, cancer, metabolic diseases, diabetes, diseases involving angiogenesis and lymphangiogenesis, diseases of obesity including reduction of dietary sugar uptake, cardiovascular disease, neoplasia, peripheral vascular disease, septic shock, hypotension, preeclampsia, ocular degeneration, idiopathic pulmonary fibrosis, inflammatory disease (such as arthritis and inflammatory bowel disease), avascular or ischemic insult, eczema, ulcers, lymphedema, bone diseases, vascular hyperplasia, hemangioma, proteinuric renal disease, diabetic retinopathy, diseases of choroidal vasculature (AMD), macular degenerative disease, psoriasis, endometriosis, glioma, glioblastoma, glioblastoma multiforma, colorectal cancer, renal carcinoma, lung cancer, mammary/breast cancer, endometriosis, any disease involving angiogenesis, and HIV infection.

In one aspect the present invention provides a method of treating a tumor, cancer, metabolic diseases, diabetes, diseases involving angiogenesis and lymphangiogenesis, diseases of obesity including reduction of dietary sugar uptake, cardiovascular disease, neoplasia, peripheral vascular disease, septic shock, hypotension, preeclampsia, ocular degeneration, idiopathic pulmonary fibrosis, inflammatory disease (such as arthritis and inflammatory bowel disease), avascular or ischemic insult, eczema, ulcers, lymphedema, bone diseases, vascular hyperplasia, hemangioma, proteinuric renal disease, diabetic retinopathy, diseases of choroidal vasculature (AMD), macular degenerative disease, psoriasis, endometriosis, glioma, glioblastoma, glioblastoma multiforma, colorectal cancer, renal carcinoma, lung cancer, mammary/breast cancer, endometriosis, any disease involving angiogenesis, and HIV infection, said method comprising administering a compound or a composition of the invention to said patient.

In one aspect the present invention provides a substance or composition for the manufacture of a medicament for the treatment or a disease or disorder selected from a tumor, cancer, metabolic diseases, diabetes, diseases involving angiogenesis and lymphangiogenesis, diseases of obesity including reduction of dietary sugar uptake, cardiovascular disease, neoplasia, peripheral vascular disease, septic shock, hypotension, preeclampsia, ocular degeneration, idiopathic pulmonary fibrosis, inflammatory disease (such as arthritis and inflammatory bowel disease), avascular or ischemic insult, eczema, ulcers, lymphedema, bone diseases, vascular hyperplasia, hemangioma, proteinuric renal disease, diabetic retinopathy, diseases of choroidal vasculature (AMD), macular degenerative disease, psoriasis, endometriosis, glioma, glioblastoma, glioblastoma multiforma, colorectal cancer, renal carcinoma, lung cancer, mammary/breast cancer, endometriosis, any disease involving angiogenesis, and HIV infection.

In one aspect the present invention provides a method of treating disease or disorder in a patient, said method comprising administering a compound or composition of the invention.

In one aspect the present invention provides a compound comprising 6 contiguously linked ($L_{1-14}$) amino acids ($X^{1-14}$) as defined from formula I, wherein the sequence overlaps with part of one of SEQ. ID NOS 3-32.

In one aspect the present invention provides a compound comprising 6 contiguously linked ($L_{1-14}$) amino acids ($X^{1-14}$) as defined from formula I, wherein the sequence overlaps with part of one of SEQ. ID NOS 3-17.

In one aspect the present invention provides a compound comprising 7 contiguously linked ($L_{1-14}$) amino acids ($X^{1-14}$) as defined from formula I, wherein the sequence overlaps with part of one of SEQ. ID NOS 3-32.

In one aspect the present invention provides a compound comprising 7 contiguously linked ($L_{1-14}$) amino acids ($X^{1-14}$) as defined from formula I, wherein the sequence overlaps with part of one of SEQ. ID NOS 3-17.

In one aspect the present invention provides a compound comprising 8 contiguously linked ($L_{1-14}$) amino acids ($X^{1-14}$) as defined from formula I, wherein the sequence overlaps with part of one of SEQ. ID NOS 3-32.

In one aspect the present invention provides a compound comprising 8 contiguously linked ($L_{1-14}$) amino acids ($X^{1-14}$) as defined from formula I, wherein the sequence overlaps with part of one of SEQ. ID NOS 3-17.

In one aspect the present invention provides a compound comprising 9 contiguously linked ($L_{1-14}$) amino acids ($X^{1-14}$) as defined from formula I, wherein the sequence overlaps with part of one of SEQ. ID NOS 3-32.

In one aspect the present invention provides a compound comprising 9 contiguously linked ($L_{1-14}$) amino acids ($X^{1-14}$) as defined from formula I, wherein the sequence overlaps with part of one of SEQ. ID NOS 3-17.

In one aspect the present invention provides a compound comprising 10 contiguously linked ($L_{1-14}$) amino acids ($X^{1-14}$) as defined from formula I, wherein the sequence overlaps with part of one of SEQ. ID NOS 3-32.

In one aspect the present invention provides a compound comprising 10 contiguously linked ($L_{1-14}$) amino acids ($X^{1-14}$) as defined from formula I, wherein the sequence overlaps with part of one of SEQ. ID NOS 3-17.

In one aspect the present invention provides a compound comprising 11 contiguously linked ($L_{1-14}$) amino acids ($X^{1-14}$) as defined from formula I, wherein the sequence overlaps with part of one of SEQ. ID NOS 3-32.

In one aspect the present invention provides a compound comprising 11 contiguously linked ($L_{1-14}$) amino acids ($X^{1-14}$) as defined from formula I, wherein the sequence overlaps with part of one of SEQ. ID NOS 3-17.

In one aspect the present invention provides a compound comprising 12 contiguously linked ($L_{1-14}$) amino acids ($X^{1-14}$) as defined from formula I, wherein the sequence overlaps with part of one of SEQ. ID NOS 3-32.

In one aspect the present invention provides a compound comprising 12 contiguously linked ($L_{1-14}$) amino acids ($X^{1-14}$) as defined from formula I, wherein the sequence overlaps with part of one of SEQ. ID NOS 3-17.

In one aspect the present invention provides a compound comprising 13 contiguously linked ($L_{1-14}$) amino acids ($X^{1-14}$) as defined from formula I, wherein the sequence overlaps with part of one of SEQ. ID NOS 3-32.

In one aspect the present invention provides a compound comprising 13 contiguously linked ($L_{1-14}$) amino acids ($X^{1-14}$) as defined from formula I, wherein the sequence overlaps with part of one of SEQ. ID NOS 3-17.

In one aspect the present invention provides a compound with 6-13 contiguously linked ($L_{1-14}$) amino acids ($X^{1-14}$) as defined from formula I, wherein the sequence overlaps with part of one of SEQ. ID NOS 3-32, for use in a medicine.

In one aspect the present invention provides a compound with 6-13 contiguously linked ($L_{1-14}$) amino acids ($X^{1-14}$) as defined from formula I, wherein the sequence overlaps with part of one of SEQ. ID NOS 3-17, for use in a medicine.

Figure 1A:
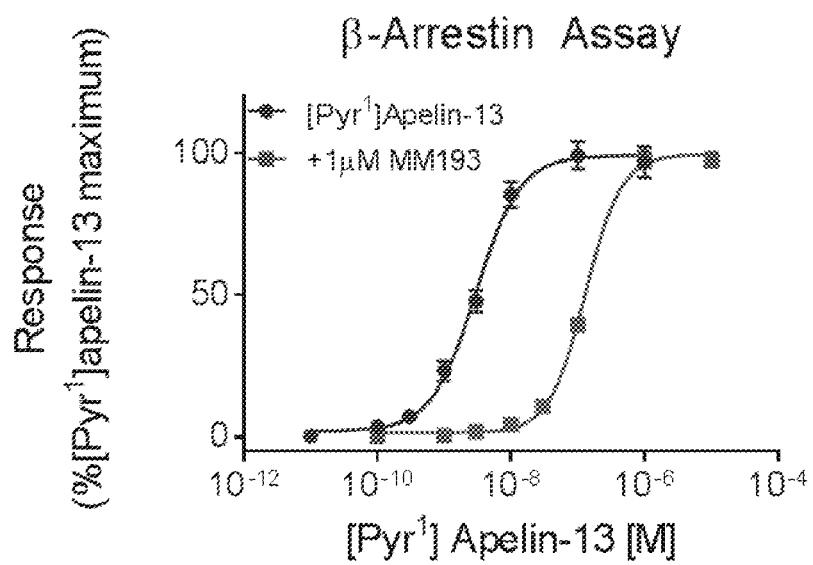
FIG. 1a depicts Antagonism of [pyr1] apelin-13 mediated β-arrestin recruitment by 1 μM MM193. Apelin-13 effect is antagonised by addition of MM193 in a competitive manner.
Figure 1B:
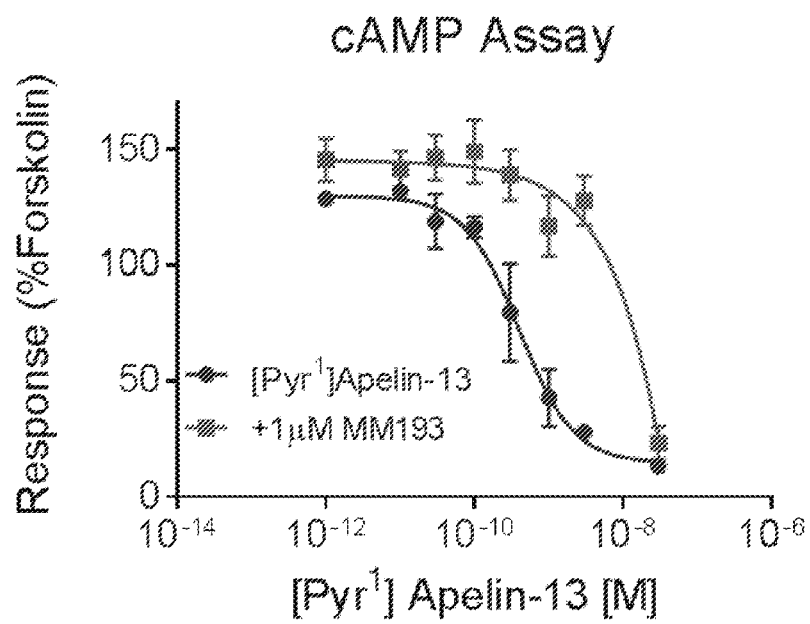
FIG. 1b depicts antagonism of [pyr1] apelin-13 inhibition of forskolin stimulated cAMP accumulation by 1 μM MM193. Apelin-13 effect is antagonised by addition of MM193 in a competitive manner.
Figure 2A:
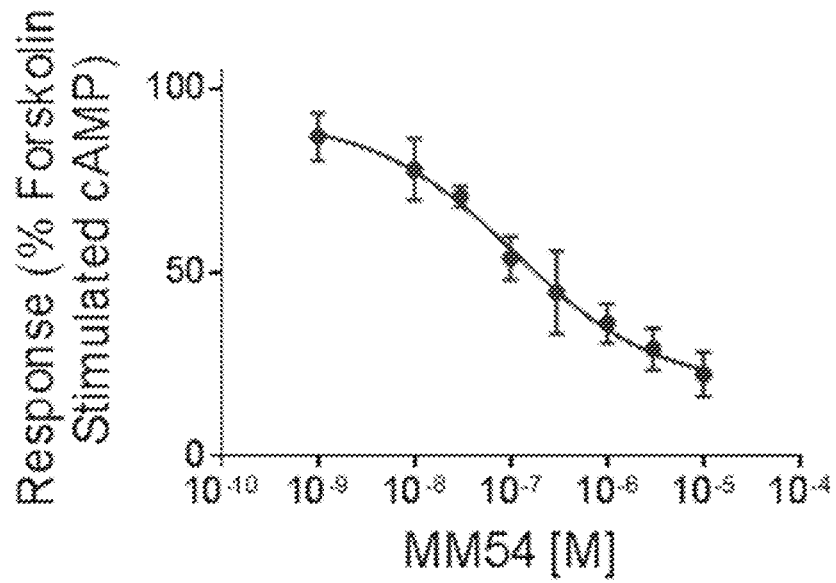
FIG. 2a depicts the effects of MM54 on forskolin stimulated cAMP response.
Figure 2B:
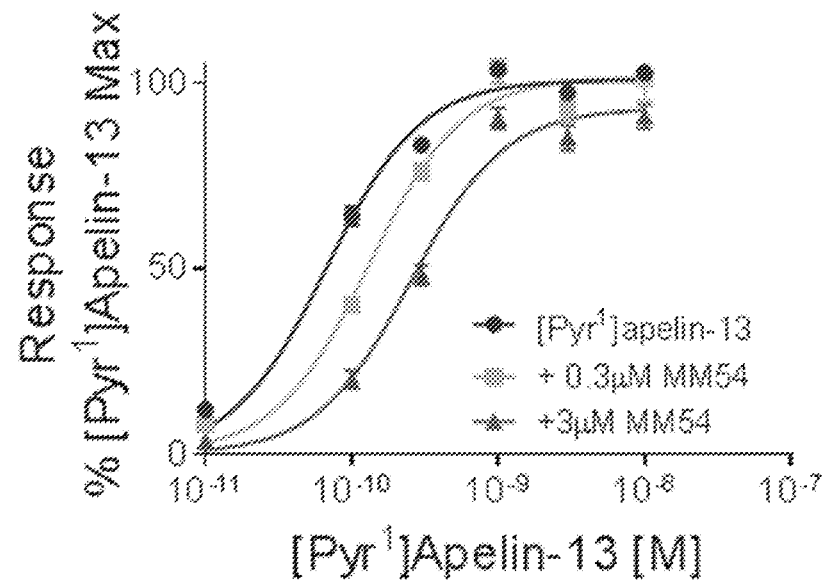
FIG. 2b depicts the effects of MM54 inhibition of β-arrestin recruitment.
Figure 3A:
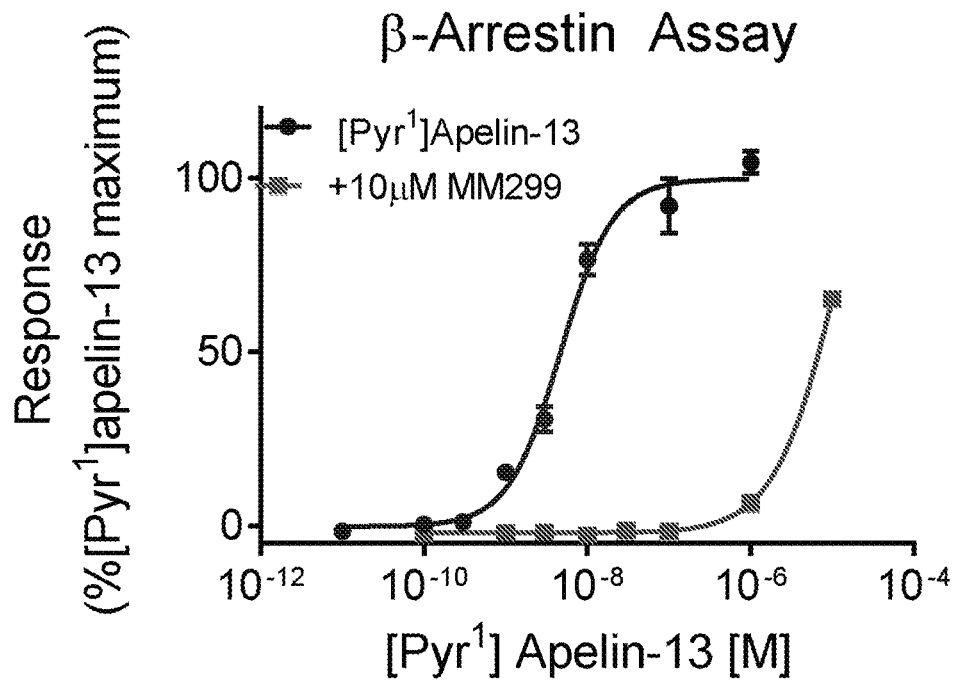
FIG. 3a depicts Antagonism of [Pyr1]apelin-13 mediated β-arrestin recruitment by 1 μM MM299.
Figure 3B:
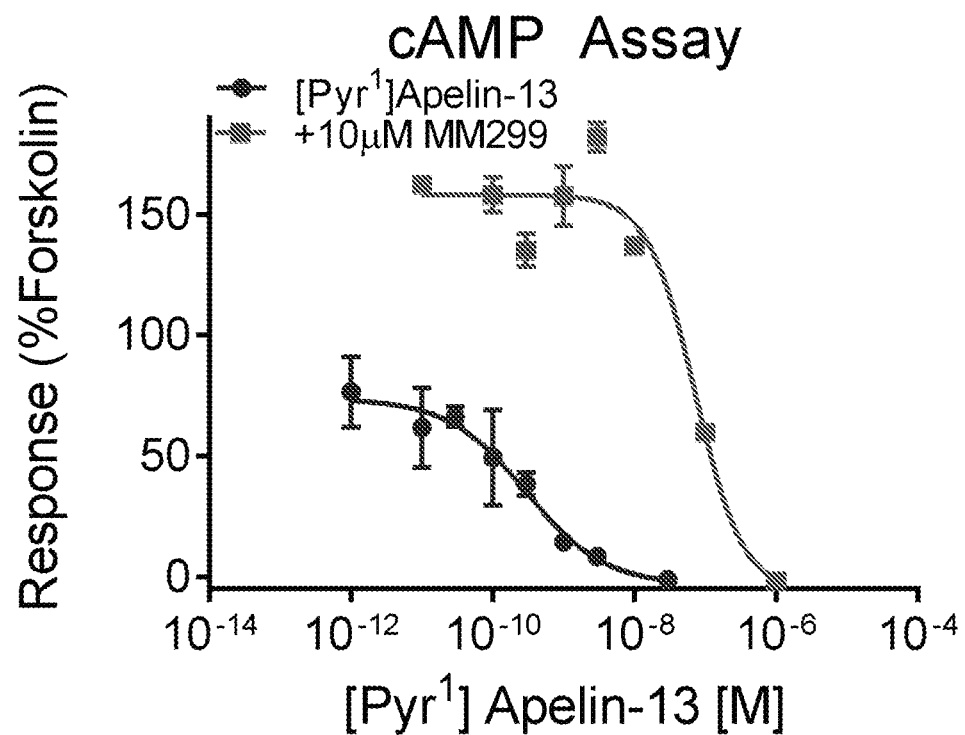
FIG. 3b depicts antagonism of [Pyr1] inhibition of forskolin stimulated cAMP accumulation by 10 μM MM299.
Figure 4A:
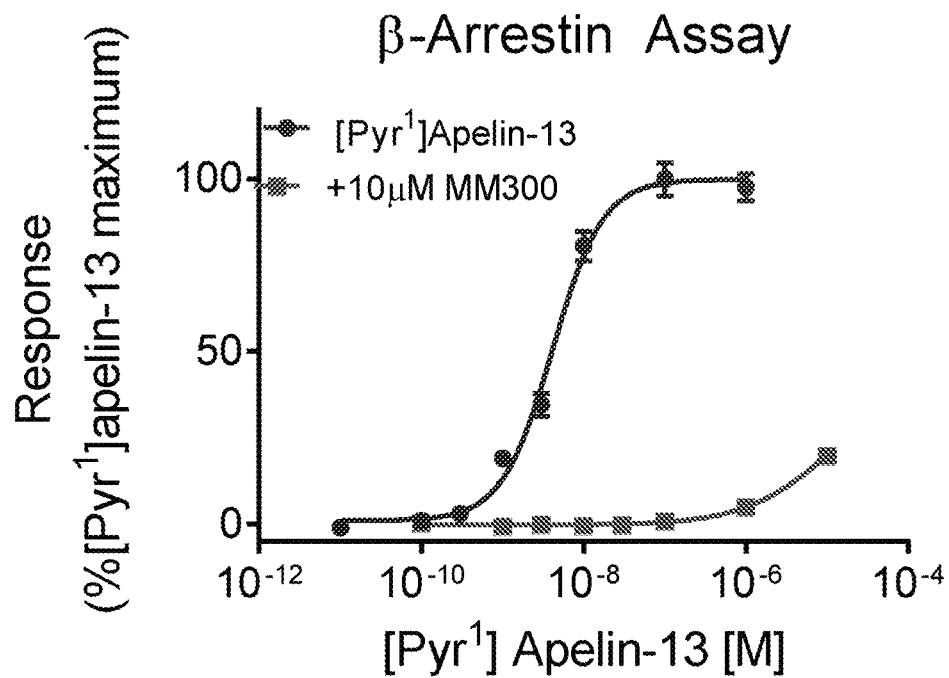
FIG. 4a depicts antagonism of [Pyr1]apelin-13 mediated β-arrestin recruitment by 1 μM MM300.
Figure 4B:
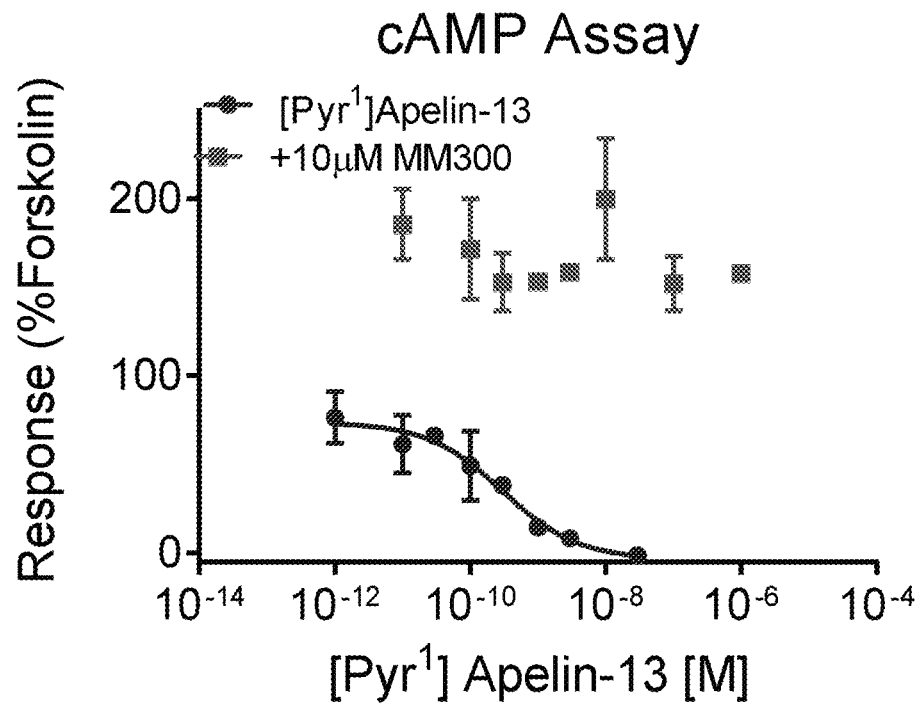
FIG. 4b depicts antagonism of [Pyr1] inhibition of forskolin stimulated cAMP accumulation by 10 μM MM300.

These figures demonstrate antagonism of apelin-13 and show a pharmacology profile consistent with antagonism of apelin receptor signalling. Since apelin receptor signalling appears to modify the glioblastoma disease process (60) these compounds are claimed to modify the glioblastoma disease process by this apelin receptor antagonism mechanism.

DETAILED DESCRIPTION OF THE INVENTION

In one aspect the present invention provides a compound comprising the sequence of Formula I:

$(R^1-L_c)-X^1-L_1-X^2-L_2-X^3-L_3-X^4-L_4-X^5-L_5-X^6-L_6-X^7-L_7-X^8-L_8-X^9-L_9-X^{10}-L_{10}-X^{11}-L_{11}-X^{12}-L_{12}-X^{13}-L_{13}-X^{14}(-L_c-R^2)$   (Formula I)

wherein
$X^1$ is any amino acid;
$X^2$ is selected from the group consisting of R, H, and K;
$X^3$ is P;
$X^4$ is R;
$X^5$ is selected from the group consisting of Nle, L, A, V, I, M, F, Y, and W;
$X^6$ is selected from the group consisting of Abu, C, A, V, I, L, M, F, Y, W, and P;
$X^7$ is selected from the group consisting of H, K, A, V, I, L, M, F, Y, W, and R;
$X^8$ is selected from the group consisting of K, H, A, V, I, L, M, F, Y, W, and R;
$X^9$ is selected from the group consisting of Abu, C, A, V, I, L, M, F, Y, W, and P;
$X^{10}$ is selected from the group consisting of R, H, and K;
$X^{11}$ is selected from the group consisting of Aib, and P;
$X^{12}$ is selected from the group consisting of R, H, and K;
$X^{13}$ is selected from the group consisting of Nle, Aib, L, V, I, and A;
$X^{14}$ is selected from the group consisting of none, C, F, other hydrophobic amino acids (including Alanine (A), Isoleucine (I), Leucine (L), Methionine (M), Tyrosine (Y), Tryptophan (W), Valine (V), Proline (P), Glycine (G)), and $X^{14}$ may specifically be one of 3,4,5-trifluorophenylalanine (Tfpa or (3,4,5-trifluoro)F), β-cyclohexylalanine (Cha), Naphthylalanine (Nal), 4-chlorophenylalanine (4cpa), 4-methoxyphenylalanine, 4-methylphenylalanine, 4-pyridylealanine, 3-pyridylalanine, 2-pyridylalanine, D-(−)-α-phenylglycine, homophenylalanine, 3-styrylalanine, O-benzyl-L-tyrosine, 4-benzoyl-L-phenylalanine, α-methyl-L-phenylalanine, α-methyl-D-phenylalanine, aminoindane, 2-aminoindane, O-benzyltyrosine, or 4-Aminopiperidine-4-carboxylic acid;
wherein:
1) for $X^1$ to $X^{14}$ any natural amino acid listed may independently be optionally modified, and wherein 2) for $X^1$ to $X^{14}$ any modified amino acid listed may independently be optionally further modified and, in options 1) and 2), the modification in option 1) and the further modification in option 2) is optionally alkylation, esterification, N-alkyl amidation, substitution of hydrogen with any halo group or hydroxyl group or conjugation to an $R^3$ moiety through a conjugation linker $L_c$;
each of $L_1$ to $L_{13}$ is independently a linkage appropriate for joining two amino acids together, such as an amide bond, N-methylated amide, urea, ester, carbamate, peptoid, sulphonamide, alkene, thioamide, thioether, fluoroalkene, azapeptide difluoroketone or epoxide;
$R^1$, $R^2$, and $R^3$ are independently absent or independently represent the rest of the compound, for example $R^1$, $R^2$, and $R^3$ can independently be a peptide, an acetyl, formyl, propinyl, biotin, myristoyl, or palmitoyl moiety, a methyl moiety, a saturated or unsaturated fatty acyl moiety, a polyethylene glycol polymer moiety, an immunoglobulin moiety, an immunoglobulin Fc domain moiety, albumin, a methylated moiety, an esterified moiety, or a portion of the natural apelin compound;
each $L_c$ is independently absent or is a conjugation linker which joins $R^1$ to $X^1$, $R^2$ to $X^{14}$, or an $R^3$ moiety to any of $X^1$ to $X^{14}$ and is selected from any linkage appropriate for joining $R^1$ to $X^1$, $R^2$ to $X^{14}$ or an $R^3$ moiety to any of $X^1$ to $X^{14}$;
or a pharmaceutically acceptable salt, solvate, amide, ester, prodrug, or deuterated analogue thereof.

In one aspect the present invention provides a compound comprising the sequence of Formula I:

$(R^1-L_c)-X^1-L_1-X^2-L_2-X^3-L_3-X^4-L_4-X^5-L_5-X^6-L_6-X^7-L_7-X^8-L_8-X^9-L_9-X^{10}-L_{10}-X^{11}-L_{11}-X^{12}-L_{12}-X^{13}-L_{13}-X^{14}(-L_c-R^2)$   (Formula I)

wherein

X¹ is any amino acid;

X² is selected from the group consisting of R, H, and K;

X³ is P;

X⁴ is R;

X⁵ is selected from the group consisting of Nle, L, A, V, I, M, F, Y, and W;

X⁶ is selected from the group consisting of Abu, C, A, V, I, L, M, F, Y, W, and P;

X⁷ is selected from the group consisting of H, K, A, V, I, L, M, F, Y, W, and R;

X⁸ is selected from the group consisting of K, H, A, V, I, L, M, F, Y, W, and R;

X⁹ is selected from the group consisting of Abu, C, A, V, I, L, M, F, Y, W, and P;

X¹⁰ is selected from the group consisting of R, H, and K;

X¹¹ is selected from the group consisting of Aib, and P;

X¹² is selected from the group consisting of R, H, and K;

X¹³ is selected from the group consisting of Nle, Aib, L, V, I, and A;

X¹⁴ is selected from the group consisting of C, F, other hydrophobic amino acids (including Alanine (A), Isoleucine (I), Leucine (L), Methionine (M), Tyrosine (Y), Tryptophan (W), Valine (V), Proline (P), Glycine (G)), and X¹⁴ may specifically be one of 3,4,5-trifluorophenylalanine (Tfpa or (3,4,5-trifluoro)F), β-cyclohexylalanine (Cha), Naphthylalanine (Nal), 4-chlorophenylalanine (4cpa), 4-methoxyphenylalanine, 4-methylphenylalanine, 4-pyridylealanine, 3-pyridylalanine, 2-pyridylalanine, D-(−)-α-phenylglycine, homophenylalanine, 3-styrylalanine, O-benzyl-L-tyrosine, 4-benzoyl-L-phenylalanine, α-methyl-L-phenylalanine, α-methyl-D-phenylalanine or aminoindane;

wherein:
1) for X¹ to X¹⁴ any natural amino acid listed may independently be optionally modified, and wherein 2) for X¹ to X¹⁴ any modified amino acid listed may independently be optionally further modified and, in options 1) and 2), the modification in option 1) and the further modification in option 2) is optionally alkylation, esterification, N-alkyl amidation, substitution of hydrogen with any halo group or hydroxyl group or conjugation to an R³ moiety through a conjugation linker $L_c$;

each of $L_1$ to $L_{13}$ is independently a linkage appropriate for joining two amino acids together, such as an amide bond, N-methylated amide, urea, ester, carbamate, peptoid, sulphonamide, alkene, thioamide, thioether, fluoroalkene, azapeptide difluoroketone or epoxide;

$R^1$, $R^2$, and $R^3$ are independently absent or independently represent the rest of the compound, for example $R^1$, $R^2$, and $R^3$ can independently be a peptide, an acetyl, formyl, propinyl, biotin, myristoyl, or palmitoyl moiety, a methyl moiety, a saturated or unsaturated fatty acyl moiety, a polyethylene glycol polymer moiety, an immunoglobulin moiety, an immunoglobulin Fc domain moiety, albumin, a methylated moiety, an esterified moiety, or a portion of the natural apelin compound;

each $L_c$ is independently absent or is a conjugation linker which joins $R^1$ to $X^1$, $R^2$ to $X^{14}$, or an $R^3$ moiety to any of $X^1$ to $X^{14}$ and is selected from any linkage appropriate for joining $R^1$ to $X^1$, $R^2$ to $X^{14}$ or an $R^3$ moiety to any of $X^1$ to $X^{14}$;

or a pharmaceutically acceptable salt, solvate, amide, ester, prodrug, or deuterated analogue thereof.

In one aspect the present invention provides a compound comprising the sequence of Formula I:

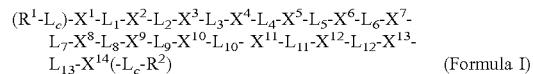
$$(R^1\text{-}L_c)\text{-}X^1\text{-}L_1\text{-}X^2\text{-}L_2\text{-}X^3\text{-}L_3\text{-}X^4\text{-}L_4\text{-}X^5\text{-}L_5\text{-}X^6\text{-}L_6\text{-}X^7\text{-}L_7\text{-}X^8\text{-}L_8\text{-}X^9\text{-}L_9\text{-}X^{10}\text{-}L_{10}\text{-}X^{11}\text{-}L_{11}\text{-}X^{12}\text{-}L_{12}\text{-}X^{13}\text{-}L_{13}\text{-}X^{14}(\text{-}L_c\text{-}R^2)$$ (Formula I)

wherein

X¹ is selected from the group consisting of V, I, L, M, P, Y, W, C, Q, Glp, and A;

X² is R;

X³ is P;

X⁴ is R;

X⁵ is selected from the group consisting of A, V, I, Nle, and L;

X⁶ is selected from the group consisting of Abu, M, P, and C;

X⁷ is selected from the group consisting of H, R, and K;

X⁸ is selected from the group consisting of R, K, or H;

X⁹ is selected from the group consisting of Abu, M, P, and C;

X¹⁰ is R, or K;

X¹¹ is selected from the group consisting of Aib, and P;

X¹² is R, K, or H;

X¹³ is selected from the group consisting of A, V, I, Nle, and L;

X¹⁴ is selected from the group consisting of none, C, F, other hydrophobic amino acids (including Alanine (A), Isoleucine (I), Leucine (L), Methionine (M), Tyrosine (Y), Tryptophan (W), Valine (V), Proline (P), Glycine (G)), and X¹⁴ may specifically be one of 3,4,5-trifluorophenylalanine (Tfpa or (3,4,5-trifluoro)F), β-cyclohexylalanine (Cha), Naphthylalanine (Nal), 4-chlorophenylalanine (4cpa), 4-methoxyphenylalanine, 4-methylphenylalanine, 4-pyridylealanine, 3-pyridylalanine, 2-pyridylalanine, D-(−)-α-phenylglycine, homophenylalanine, 3-styrylalanine, O-benzyl-L-tyrosine, 4-benzoyl-L-phenylalanine, α-methyl-L-phenylalanine, α-methyl-D-phenylalanine, aminoindane, 2-aminoindance, O-benzyltyrosine, or 4-Aminopiperidine-4-carboxylic acid;

wherein:
1) for X¹ to X¹⁴ any natural amino acid listed may independently be optionally modified, and wherein 2) for X¹ to X¹⁴ any modified amino acid listed may independently be optionally further modified and, in options 1) and 2), the modification in option 1) and the further modification in option 2) is optionally alkylation, esterification, N-alkyl amidation, substitution of hydrogen with any halo group or hydroxyl group or conjugation to an R³ moiety through a conjugation linker $L_c$;

each of $L_1$ to $L_{13}$ is independently a linkage appropriate for joining two amino acids together, such as an amide bond, N-methylated amide, urea, ester, carbamate, peptoid, sulphonamide, alkene, thioamide, thioether, fluoroalkene, azapeptide difluoroketone or epoxide;

$R^1$, $R^2$, and $R^3$ are independently absent or independently represent the rest of the compound, for example $R^1$, $R^2$, and $R^3$ can independently be a peptide, an acetyl, formyl, propinyl, biotin, myristoyl, or palmitoyl moiety, a methyl moiety, a saturated or unsaturated fatty acyl moiety, a polyethylene glycol polymer moiety, an immunoglobulin moiety, an immunoglobulin Fc domain moiety, albumin, a methylated moiety, an esterified moiety, or a portion of the natural apelin compound;

each $L_c$ is independently absent or is a conjugation linker which joins $R^1$ to $X^1$, $R^2$ to $X^{14}$, or an $R^3$ moiety to any of $X^1$ to $X^{14}$ and is selected from any linkage appropriate for joining $R^1$ to $X^1$, $R^2$ to $X^{14}$ or an $R^3$ moiety to any of $X^1$ to $X^{14}$;

or a pharmaceutically acceptable salt, solvate, amide, ester, prodrug, or deuterated analogue thereof.

In one aspect the present invention provides a compound comprising the sequence of Formula I:

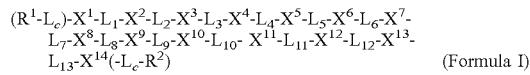

(Formula I)

wherein $X^1$ is selected from the group consisting of V, I, L, M, P, Y, W, C, Q, Glp, and A;

$X^2$ is R;

$X^3$ is P;

$X^4$ is R;

$X^5$ is selected from the group consisting of A, V, I, Nle, and L;

$X^6$ is selected from the group consisting of Abu, M, P, and C;

$X^7$ is selected from the group consisting of H, R, and K;

$X^8$ is selected from the group consisting of R, K, or H;

$X^9$ is selected from the group consisting of Abu, M, P, and C;

$X^{10}$ is R, or K;

$X^{11}$ is selected from the group consisting of Aib, and P;

$X^{12}$ is R, K, or H;

$X^{13}$ is selected from the group consisting of A, V, I, Nle, and L;

$X^{14}$ is selected from the group consisting of C, F, other hydrophobic amino acids (including Alanine (A), Isoleucine (I), Leucine (L), Methionine (M), Tyrosine (Y), Tryptophan (W), Valine (V), Proline (P), Glycine (G)), and $X^{14}$ may specifically be one of 3,4,5-trifluorophenylalanine (Tfpa or (3,4,5-trifluoro)F), β-cyclohexylalanine (Cha), Naphthylalanine (Nal), 4-chlorophenylalanine (4cpa), 4-methoxyphenylalanine, 4-methylphenylalanine, 4-pyridylealanine, 3-pyridylalanine, 2-pyridylalanine, D-(−)-α-phenylglycine, homophenylalanine, 3-styrylalanine, O-benzyl-L-tyrosine, 4-benzoyl-L-phenylalanine, α-methyl-L-phenylalanine, α-methyl-D-phenylalanine or aminoindane;

wherein:

1) for $X^1$ to $X^{14}$ any natural amino acid listed may independently be optionally modified, and wherein 2) for $X^1$ to $X^{14}$ any modified amino acid listed may independently be optionally further modified and, in options 1) and 2), the modification in option 1) and the further modification in option 2) is optionally alkylation, esterification, N-alkyl amidation, substitution of hydrogen with any halo group or hydroxyl group or conjugation to an $R^3$ moiety through a conjugation linker $L_c$;

each of $L_1$ to $L_{13}$ is independently a linkage appropriate for joining two amino acids together, such as an amide bond, N-methylated amide, urea, ester, carbamate, peptoid, sulphonamide, alkene, thioamide, thioether, fluoroalkene, azapeptide difluoroketone or epoxide;

$R^1$, $R^2$, and $R^3$ are independently absent or independently represent the rest of the compound, for example $R^1$, $R^2$, and $R^3$ can independently be a peptide, an acetyl, formyl, propinyl, biotin, myristoyl, or palmitoyl moiety, a methyl moiety, a saturated or unsaturated fatty acyl moiety, a polyethylene glycol polymer moiety, an immunoglobulin moiety, an immunoglobulin Fc domain moiety, albumin, a methylated moiety, an esterified moiety, or a portion of the natural apelin compound;

each $L_c$ is independently absent or is a conjugation linker which joins $R^1$ to $X^1$, $R^2$ to $X^{14}$, or an $R^3$ moiety to any of $X^1$ to $X^{14}$ and is selected from any linkage appropriate for joining $R^1$ to $X^1$, $R^2$ to $X^{14}$ or an $R^3$ moiety to any of $X^1$ to $X^{14}$;

or a pharmaceutically acceptable salt, solvate, amide, ester, prodrug, or deuterated analogue thereof.

In some embodiments $X^1$ can be selected from the group consisting of V, I, L, M, P, Y, W, C, Q, Glp, and A.

In some embodiments $X^2$ can be R.

In some embodiments $X^3$ can be P.

In some embodiments $X^4$ can be R.

In some embodiments $X^5$ can be selected from the group consisting of A, V, I, Nle, and L.

In some embodiments $X^6$ can be selected from the group consisting of Abu, M, P, and C.

In some embodiments $X^7$ can be selected from the group consisting of H, R, and K.

In some embodiments $X^3$ can be selected from the group consisting of R, K, and H.

In some embodiments $X^9$ can be selected from the group consisting of Abu, M, P, and C.

In some embodiments $X^{10}$ can be selected from the group consisting of R, and K.

In some embodiments $X^{11}$ can be selected from the group consisting of Aib, and P.

In some embodiments $X^{12}$ can be selected from the group consisting of R, K, and H.

In some embodiments $X^{13}$ can be selected from the group consisting of A, V, I, Nle, and L.

In some embodiments $X^{14}$ can be selected from the group consisting of none, C, F, other hydrophobic amino acids (including Alanine (A), Isoleucine (I), Leucine (L), Methionine (M), Phenylalanine (F), Tyrosine (Y), Tryptophan (W), Valine (V), Proline (P), Glycine (G)), and $X^{14}$ may specifically be one of 3,4,5-trifluorophenylalanine (Tfpa or (3,4,5-trifluoro)F), β cyclohexylalanine (Cha), Naphthylalanine (Nal), 4-chlorophenylalanine (4cpa), 4 methoxyphenylalanine, 4-methylphenylalanine, 4-pyridylealanine, 3-pyridylalanine, 2 pyridylalanine, D-(−)-α-phenylglycine, homophenylalanine, 3-styrylalanine, O benzyl L tyrosine, 4-benzoyl-L-phenylalanine, α-methyl-L-phenylalanine, α-methyl-D-phenylalanine, aminoindane, 2-aminoindane, O-benzyltyrosine, or 4-Aminopiperidine-4-carboxylic acid.

In some embodiments $X^{14}$ can be selected from the group consisting of C, F, other hydrophobic amino acids (including Alanine (A), Isoleucine (I), Leucine (L), Methionine (M), Phenylalanine (F), Tyrosine (Y), Tryptophan (W), Valine (V), Proline (P), Glycine (G)), and $X^{14}$ may specifically be one of 3,4,5-trifluorophenylalanine (Tfpa or (3,4,5-trifluoro) F), β cyclohexylalanine (Cha), Naphthylalanine (Nal), 4-chlorophenylalanine (4cpa), 4 methoxyphenylalanine, 4-methylphenylalanine, 4-pyridylealanine, 3-pyridylalanine, 2 pyridylalanine, D-(−)-α-phenylglycine, homophenylalanine, 3-styrylalanine, O benzyl L tyrosine, 4-benzoyl-L-phenylalanine, α-methyl-L-phenylalanine, α-methyl-D-phenylalanine or aminoindane.

In some embodiments the compound can be a compound of formula (I) or a pharmaceutically acceptable salt, solvate, or deuterated analogue thereof.

In some embodiments the compound can be a compound of formula (I) or a pharmaceutically acceptable salt or solvate thereof.

In some embodiments one or more of $X^1$ to $X^{14}$ can be each independently linked to an $R^3$ moiety through a conjugation linker $L_c$.

In some embodiments one or more of $X^1$, $X^6$, $X^9$, and $X^{14}$ can be each independently linked to an $R^3$ moiety through a conjugation linker $L_c$, optionally wherein the conjugation linker is a maleimide or pegylated maleimide, optionally wherein $R^3$ is a fatty acid, pegylated, a peptide, a polypeptide, or an antibody molecule.

In some embodiments none of $X^1$ to $X^{14}$ may be linked to $R^3$ through a conjugation linker $L_c$.

In some embodiments one of ($R^1$-$L_c$) and (-$L_c$-$R^2$) can be absent.

In some embodiments both of ($R^1$-$L_c$) and (-$L_c$-$R^2$) may be absent such that the sequence terminates at $X^1$ and $X^{14}$.

In some embodiments for each of $X^1$ to $X^{14}$ none of the natural amino acids listed may be modified and none of the modified amino acids listed may be further modified.

In some embodiments each of $L_1$ to $L_{14}$ can be an amide or N-methylated amide linkage, may alternatively be an amide linkage.

In some embodiments $X^1$ can be C, Q, Glp, or A.
In some embodiments $X^1$ can be C.
In some embodiments $X^1$ can be Q.
In some embodiments $X^1$ can be Glp.
In some embodiments $X^1$ can be A.
In some embodiments $X^2$ can be R.
In some embodiments $X^3$ can be P.
In some embodiments $X^4$ can be R.
In some embodiments $X^2$ can be R and said R can be modified by methylation.
In some embodiments $X^4$ can be R and said R can be modified by methylation.
In some embodiments $X^5$ can be selected from the group consisting of Nle and L.
In some embodiments $X^{13}$ can be selected from the group consisting of Nle and L.
In some embodiments $X^6$ can be selected from the group consisting of C and Abu.
In some embodiments $X^9$ can be independently selected from the group consisting of C and Abu.
In some embodiments $X^7$ can be K and $X^8$ can be H, or wherein $X^7$ can be H and $X^8$ can be K, or wherein $X^7$ can be A and $X^8$ can be K, or wherein $X^7$ can be K and $X^8$ can be A.
In some embodiments one of $X^7$ and $X^8$ can be H and the other can be K.
In some embodiments $X^{10}$ can be R.
In some embodiments $X^{10}$ and $X^{12}$ can be R.
In some embodiments $X^{11}$ can be selected from the group consisting of P and Aib.
In some embodiments $X^{14}$ can be selected from C and (3,4,5-trifluoro-)F, preferably (3,4,5-trifluoro-)F.
In some embodiments $X^1$ can be C, optionally wherein $R^1$ can be myristoyl.
In some embodiments $X^5$ can be Ne.
In some embodiments $X^6$ can be Abu.
In some embodiments $X^7$ can be K and $X^8$ can be H.
In some embodiments $X^9$ can be Abu.
In some embodiments $X^{10}$ can be R.
In some embodiments $X^{11}$ can be Aib.
In some embodiments $X^{12}$ can be R.
In some embodiments $X^{13}$ can be Ne.
In some embodiments $X^{14}$ can be (3,4,5-trifluoro)F.
In some embodiments $X^1$ can be modified.
In some embodiments $X^1$ can be not modified.
In some embodiments $X^2$ can be modified.
In some embodiments $X^2$ can be not modified.
In some embodiments $X^3$ can be modified.
In some embodiments $X^3$ can be not modified.
In some embodiments $X^4$ can be modified.
In some embodiments $X^4$ can be not modified.
In some embodiments $X^5$ can be modified.
In some embodiments $X^5$ can be not modified.
In some embodiments $X^6$ can be modified.
In some embodiments $X^6$ can be not modified.
In some embodiments $X^7$ can be modified.
In some embodiments $X^7$ can be not modified.
In some embodiments $X^8$ can be modified.
In some embodiments $X^8$ can be not modified.
In some embodiments $X^9$ can be modified.
In some embodiments $X^9$ can be not modified.
In some embodiments $X^{10}$ can be modified.
In some embodiments $X^{10}$ can be not modified.
In some embodiments $X^{11}$ can be modified.
In some embodiments $X^{11}$ can be not modified.
In some embodiments $X^{12}$ can be modified.
In some embodiments $X^{12}$ can be not modified.
In some embodiments $X^{13}$ can be modified.
In some embodiments $X^{13}$ can be not modified.
In some embodiments $X^{14}$ can be modified.
In some embodiments $X^{14}$ can be not modified.

In some embodiments one or more of $X^1$ to $X^{14}$ can be C, R, or K and can be modified, wherein the modification comprises directly or indirectly joining said C, R or K to a protein or fatty acid.

In some embodiments $R^1$ can be a C1 to C25 saturated or unsaturated fatty acyl moiety optionally bound to $X^1$ through a conjugation linker $L_c$.

In some embodiments the fatty acyl moiety can comprise a fatty acyl group selected from the group consisting of Butanoyl, Hexanoyl, Octanoyl, Decanoyl, Dodecanoyl, Tridecanoyl, Tetradecanoyl, Pentadecanoyl, Hexadecanoyl, Heptadecanoyl, Octadecanoyl, Octadecandioyl, Octanedioyl, Decanedioyl, Dodecanedioyl, Hexanedioyl, Butanedioyl, Tetradecanedioyl, and Hexadecanedioyl.

In some embodiments $R^1$ can be a polyethyleneglycol polymer moiety optionally bound to $X^1$ through a conjugation linker $L_c$.

In some embodiments the polyethyleneglycol polymer moiety can comprise a 5 kDa, 10 kDa, or 20 kDa polyethylene glycol polymer.

In some embodiments at least one conjugation linker $L_c$ can be present and comprises 3-mercaptopropanoic acid.

In some embodiments $R^1$ is an immunoglobulin moiety or an immunoglobulin Fc domain moiety optionally bound to $X^1$ through a conjugation linker $L_c$.

In some embodiments at least one conjugation linker $L_c$ can be present and can be a peptidyl linker.

In some embodiments at least one conjugation linker $L_c$ can be present and can be a non-peptidyl linker.

In some embodiments the non-peptidyl conjugation linker $L_c$ can comprise a polyethylene glycol polymer.

In some embodiments at least one conjugation linker $L_c$ can be present and can comprise a maleimide moiety, a pegylated maleimide moiety or a thioether.

In some embodiments $X^1$ can be C and $R^1$ can be a protein, for example a protein selected from albumin and albudAb. AlbudAb is defined in this reference: O'Connor-Semmes, Lin J, Hodge R J, Andrews S1, Chism J, Choudhury A, Nunez D J. GSK2374697, a novel albumin-binding domain antibody (AlbudAb), extends systemic exposure of exendin-4: first study in humans—PK/PD and safety. Clin Pharmacol Ther. 2014 December; 96(6):704-12.

In some embodiments the compound can be selected from the following table:

| Comp. No. | (R$^1$-L$_c$) | X$^1$ | X$^2$ | X$^3$ | X$^4$ | X$^5$ | X$^6$ | X$^7$ | X$^8$ | X$^9$ | X$^{10}$ | X$^{11}$ | X$^{12}$ | X$^{13}$ | X$^{14}$ | (R$^2$-L$_c$) |
|---|---|---|---|---|---|---|---|---|---|---|---|---|---|---|---|---|
| MM107 | — | C | R | P | R | L | C | H | K | C | R | P | R | L | C | — |
| MM108 | — | C | R | P | R | L | C | K | H | C | R | P | R | L | C | — |
| MM193 | — | C | R | P | R | Nle | C | K | H | C | R | Aib | R | Nle | (3,4,5-trifluoro-)F | — |
| MM262 | — | Q | R | P | R | Nle | C | K | H | C | R | Aib | R | Nle | (3,4,5-trifluoro-)F | — |
| MM297 | — | Glp | R | P | R | Nle | C | K | H | C | R | Aib | R | Nle | (3,4,5-trifluoro-)F | — |
| MM298 | — | C | R | P | R | Nle | Abu | K | H | C | R | Aib | R | Nle | (3,4,5-trifluoro-)F | — |
| MM299 | — | C | R | P | R | Nle | C | K | H | Abu | R | Aib | R | Nle | (3,4,5-trifluoro-)F | — |
| MM300 | Myristoyl | C | R | P | R | Nle | C | K | H | C | R | Aib | R | Nle | (3,4,5-trifluoro-)F | — |
| MM301 | — | Glp | R | P | R | Nle | Abu | K | H | Abu | R | Aib | R | Nle | (3,4,5-trifluoro-)F | — |
| MM302 | — | C | R | P | R | Nle | C | H | K | C | R | Aib | R | Nle | (3,4,5-trifluoro-)F | — |
| MM312 | — | A | R | P | R | Nle | C | K | H | Abu | R | Aib | R | Nle | (3,4,5-trifluoro-)F | — |
| MM313 | Ac | A | R | P | R | Nle | C | K | H | Abu | R | Aib | R | Nle | (3,4,5-trifluoro-)F | — |
| MM314 | — | A | R | P | R | Nle | Abu | K | H | Abu | R | Aib | R | Nle | (3,4,5-trifluoro-)F | — |
| MM315 | Myristoyl | A | R | P | R | Nle | Abu | K | H | Abu | R | Aib | R | Nle | (3,4,5-trifluoro-)F | — |
| MM316 | Myristoyl | A | R | P | R | Nle | Abu | H | K | Abu | R | Aib | R | Nle | (3,4,5-trifluoro-)F | — |

In some embodiments the compound can be selected from the following table:

| Comp. No. | (R$^1$-L$_c$) | X$^1$ | X$^2$ | X$^3$ | X$^4$ | X$^5$ | X$^6$ | X$^7$ | X$^8$ | X$^9$ | X$^{10}$ | X$^{11}$ | X$^{12}$ | X$^{13}$ | X$^{14}$ | (R$^2$-L$_c$) |
|---|---|---|---|---|---|---|---|---|---|---|---|---|---|---|---|---|
| MM107 | — | C | R | P | R | L | C | H | K | C | R | P | R | L | C | — |
| MM108 | — | C | R | P | R | L | C | K | H | C | R | P | R | L | C | — |
| MM193 | — | C | R | P | R | Nle | C | K | H | C | R | Aib | R | Nle | (3,4,5-trifluoro-)F | — |
| MM262 | — | Q | R | P | R | Nle | C | K | H | C | R | Aib | R | Nle | (3,4,5-trifluoro-)F | — |
| MM297 | — | Glp | R | P | R | Nle | C | K | H | C | R | Aib | R | Nle | (3,4,5-trifluoro-)F | — |
| MM298 | — | C | R | P | R | Nle | Abu | K | H | C | R | Aib | R | Nle | (3,4,5-trifluoro-)F | — |
| MM299 | — | C | R | P | R | Nle | C | K | H | Abu | R | Aib | R | Nle | (3,4,5-trifluoro-)F | — |
| MM300 | Myristoyl | C | R | P | R | Nle | C | K | H | C | R | Aib | R | Nle | (3,4,5-trifluoro-)F | — |
| MM301 | — | Glp | R | P | R | Nle | Abu | K | H | Abu | R | Aib | R | Nle | (3,4,5-trifluoro-)F | — |
| MM302 | — | C | R | P | R | Nle | C | H | K | C | R | Aib | R | Nle | (3,4,5-trifluoro-)F | — |
| MM312 | — | A | R | P | R | Nle | C | K | H | Abu | R | Aib | R | Nle | (3,4,5-trifluoro-)F | — |
| MM313 | Ac | A | R | P | R | Nle | C | K | H | Abu | R | Aib | R | Nle | (3,4,5-trifluoro-)F | — |
| MM314 | — | A | R | P | R | Nle | Abu | K | H | Abu | R | Aib | R | Nle | (3,4,5-trifluoro-)F | — |
| MM315 | Myristoyl | A | R | P | R | Nle | Abu | K | H | Abu | R | Aib | R | Nle | (3,4,5-trifluoro-)F | — |
| MM316 | Myristoyl | A | R | P | R | Nle | Abu | H | K | Abu | R | Aib | R | Nle | (3,4,5-trifluoro-)F | — |
| MM412 | Ac | A | R | P | R | Nle | Abu | K(GluPAL) | H | Abu | R | Aib | R | Nle | (3,4,5-trifluoro-)F | |
| MM413 | | A | R | P | R | Nle | Abu | K | H | Abu | R | Aib | R | Nle | — | — |
| MM413 | | A | R | P | R | Nle | Abu | K | H | Abu | R | Aib | R | Nle | | |
| MM414 | | A | R | P | R | Nle | Abu | K | H | Abu | R | Aib | R | Nle | Alanine | |
| MM415 | | A | R | P | R | Nle | Abu | K | H | Abu | R | Aib | R | Nle | Phenylglycine | |
| MM416 | | A | R | P | R | Nle | Abu | K | H | Abu | R | Aib | R | Nle | Phenylalanine | |
| MM417 | | A | R | P | R | Nle | Abu | K | H | Abu | R | Aib | R | Nle | 4-methoxyphenly-alanine | |
| MM418 | | A | R | P | R | Nle | Abu | K | H | Abu | R | Aib | R | Nle | 4-chlorophenyl-alanine | |
| MM419 | | A | R | P | R | Nle | Abu | K | H | Abu | R | Aib | R | Nle | 4-benzoylphenyl-alanine | |
| MM420 | | A | R | P | R | Nle | Abu | K | H | Abu | R | Aib | R | Nle | O-Benzyltyrosine | |
| MM421 | | A | R | P | R | Nle | Abu | K | H | Abu | R | Aib | R | Nle | 3-(1-naphthyl)alanine | |
| MM422 | | A | R | P | R | Nle | Abu | K | H | Abu | R | Aib | R | Nle | 3-(2-naphthyl)alanine | |
| MM423 | | A | R | P | R | Nle | Abu | K | H | Abu | R | Aib | R | Nle | 2-Aminoindane | |
| MM424 | | A | R | P | R | Nle | Abu | K | H | Abu | R | Aib | R | Nle | 4-Aminopiperidine-4-carboxylic acid | |
| MM426 | Ac | A | R | P | R | Nle | Abu | K(PAL) | H | Abu | R | Aib | R | Nle | (3,4,5-trifluoro-)F | |
| MM428 | | A | R | P | R | Nle | Abu | K | H | Abu | R | Aib | R | Nle | Alpha-Methyl-L-phenylalanine | |

In some embodiments said compound is an apelin receptor antagonist.

In one aspect the present invention provides a pharmaceutical composition comprising a compound of the invention and a pharmaceutically acceptable diluent, excipient, or carrier.

In one aspect the present invention provides a composition that is formulated for:
(a) systemic delivery such as intravenous, subcutaneous, intramuscular, intraperitoneal, intranasal, intravaginal, intrarectal, intrapulmonary, intra-cranial or oral delivery;
(b) local delivery such as topical, or iontophoretic delivery; or
(c) transdermal delivery such as by a patch.
(d) inhalation via the lung
(e) intra-ocular delivery including topical, injectable, contact lenses-releasing medications, biodegradable micro- and nanoparticles, and surgically implanted systems.

In one aspect the present invention provides a compound comprising 6 contiguously linked ($L_{1-14}$) amino acids ($X^{1-14}$) as defined from formula I, wherein the sequence overlaps with part of one of SEQ. ID NOS 3-32.

In one aspect the present invention provides a compound comprising 6 contiguously linked ($L_{1-14}$) amino acids ($X^{1-14}$) as defined from formula I, wherein the sequence overlaps with part of one of SEQ. ID NOS 3-17.

In one aspect the present invention provides a compound comprising 7 contiguously linked ($L_{1-14}$) amino acids ($X^{1-14}$) as defined from formula I, wherein the sequence overlaps with part of one of SEQ. ID NOS 3-32.

In one aspect the present invention provides a compound comprising 7 contiguously linked ($L_{1-14}$) amino acids ($X^{1-14}$) as defined from formula I, wherein the sequence overlaps with part of one of SEQ. ID NOS 3-17.

In one aspect the present invention provides a compound comprising 8 contiguously linked ($L_{1-14}$) amino acids ($X^{1-14}$) as defined from formula I, wherein the sequence overlaps with part of one of SEQ. ID NOS 3-32.

In one aspect the present invention provides a compound comprising 8 contiguously linked ($L_{1-14}$) amino acids ($X^{1-14}$) as defined from formula I, wherein the sequence overlaps with part of one of SEQ. ID NOS 3-17.

In one aspect the present invention provides a compound comprising 9 contiguously linked ($L_{1-14}$) amino acids ($X^{1-14}$) as defined from formula I, wherein the sequence overlaps with part of one of SEQ. ID NOS 3-32.

In one aspect the present invention provides a compound comprising 9 contiguously linked ($L_{1-14}$) amino acids ($X^{1-14}$) as defined from formula I, wherein the sequence overlaps with part of one of SEQ. ID NOS 3-17.

In one aspect the present invention provides a compound comprising 10 contiguously linked ($L_{1-14}$) amino acids ($X^{1-14}$) as defined from formula I, wherein the sequence overlaps with part of one of SEQ. ID NOS 3-32.

In one aspect the present invention provides a compound comprising 10 contiguously linked ($L_{1-14}$) amino acids ($X^{1-14}$) as defined from formula I, wherein the sequence overlaps with part of one of SEQ. ID NOS 3-17.

In one aspect the present invention provides a compound comprising 11 contiguously linked ($L_{1-4}$) amino acids ($X^{1-14}$) as defined from formula I, wherein the sequence overlaps with part of one of SEQ. ID NOS 3-32.

In one aspect the present invention provides a compound comprising 11 contiguously linked ($L_{1-14}$) amino acids ($X^{1-14}$) as defined from formula I, wherein the sequence overlaps with part of one of SEQ. ID NOS 3-17.

In one aspect the present invention provides a compound comprising 12 contiguously linked ($L_{1-14}$) amino acids ($X^{1-14}$) as defined from formula I, wherein the sequence overlaps with part of one of SEQ. ID NOS 3-32.

In one aspect the present invention provides a compound comprising 12 contiguously linked ($L_{1-14}$) amino acids ($X^{1-14}$) as defined from formula I, wherein the sequence overlaps with part of one of SEQ. ID NOS 3-17.

In one aspect the present invention provides a compound comprising 13 contiguously linked ($L_{1-14}$) amino acids ($X^{1-14}$) as defined from formula I, wherein the sequence overlaps with part of one of SEQ. ID NOS 3-32.

In one aspect the present invention provides a compound comprising 13 contiguously linked ($L_{1-14}$) amino acids ($X^{1-14}$) as defined from formula I, wherein the sequence overlaps with part of one of SEQ. ID NOS 3-17.

In one aspect the present invention provides a compound with 6-13 contiguously linked ($L_{1-14}$) amino acids ($X^{1-14}$) as defined from formula I, wherein the sequence overlaps with part of one of SEQ. ID NOS 3-32, for use in a medicine.

In one aspect the present invention provides a compound with 6-13 contiguously linked ($L_{1-14}$) amino acids ($X^{1-14}$) as defined from formula I, wherein the sequence overlaps with part of one of SEQ. ID NOS 3-17, for use in a medicine.

Definitions

Compounds of the invention may comprise two or more amino acids linked together and may be referred to as peptides or polypeptides. The terms 'polypeptide(s)' and 'peptide(s)' are also used interchangeably to refer to two or more amino acids linked together. Peptides are indicated with the N-terminus on the left and the sequence is written from the N-terminus to the C-terminus.

Natural amino acids refer to those found in nature. Typically, most naturally occurring peptides comprise L-amino acids. However, it is not beyond the scope of this invention to envisage apelin receptor antagonists comprising D-amino acids. The L- and D-prefixes refer to the chirality of the amino acid. Unless specified as a D-amino acid, the amino acids used in the compounds of this invention are L-amino-acids. Peptides of the invention may contain modified amino acids (i.e., amino acids not found in nature or natural amino acids that have been synthetically or biosynthetically transformed), which have the following general structure:

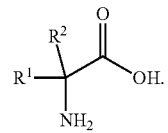

It will be apparent to those skilled in the art how to select appropriate $R^1$ and $R^2$ substituents. For example, $R^1$ and $R^2$ may comprise the same substituent or may comprise different substituents. It is known that having different $R^1$ and $R^2$ substituents may result in a stereogenic centre which may affect the 3-dimensional shape and/or properties of the peptide that the amino acid is part of. $R^1$ and $R^2$ may independently be hydrogen and may not be explicitly represented on structural formulae. Amino acids may have more than one stereogenic centre.

Modified amino acids may also refer to beta (β) and gamma (γ) amino acids, in addition to alpha (α) amino acids (e.g. carbon bound to an amine, carboxylic acid and one or two R groups).

Where one letter codes are used to refer to natural amino acids the codes used are as follows:

| One-letter code | L-Amino acid | Structure |
|---|---|---|
| R | Arginine | 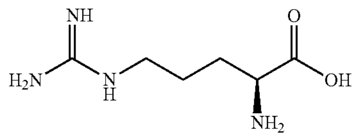 |
| H | Histidine | 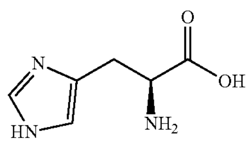 [SMILES: N[C@@H](Cc1c[nH]cn1)C(=O)O] |
| K | Lysine | 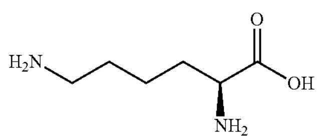 |
| D | Aspartic Acid | 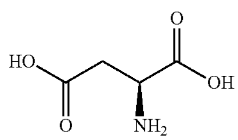 |
| E | Glutamic Acid | 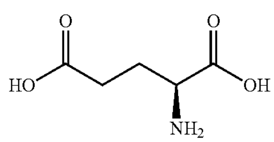 |
| S | Serine | 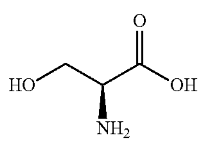 |
| T | Threonine | 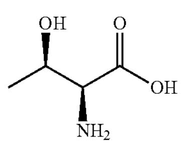 |
| N | Asparagine | 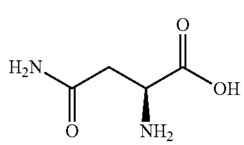 |
| Q | Glutamine | 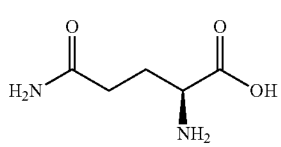 |

-continued

| One-letter code | L-Amino acid | Structure |
|---|---|---|
| C | Cysteine | 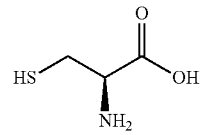 |
| U | Seleno-cysteine | 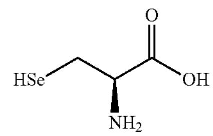 |
| G | Glycine | 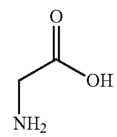 |
| P | Proline | 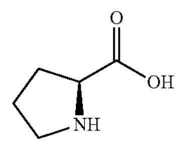 |
| A | Alanine | 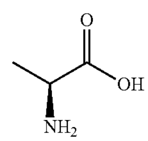 |
| V | Valine | 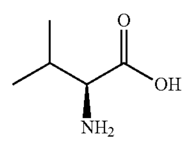 |
| I | Isoleucine | 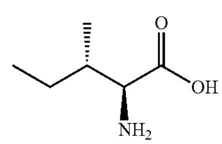 |
| L | Leucine | 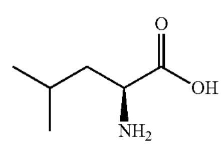 |
| M | Methionine | 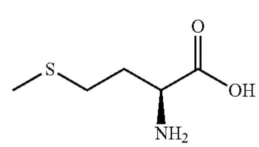 |
| F | Phenyl-alanine | 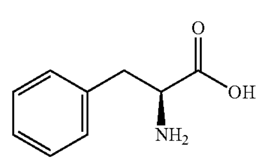 [SMILES: N[C@@H](Cc1ccccc1)C(=O)O] |

| One-letter code | L-Amino acid | Structure |
|---|---|---|
| Y | Tyrosine | 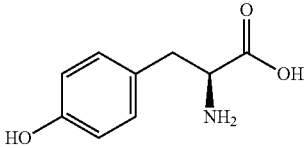 [SMILES: N[C@@H](Cc1ccc(O)cc1)C(=O)O] |
| W | Tryptophan | 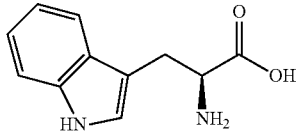 [SMILES: N[C@@H](Cc1c[nH]c2ccccc12)C(=O)O] |

Where the following compound names (or short-hand codes) are used herein, these refer to the corresponding compounds depicted below:

| Name | Structure |
|---|---|
| 3,4,5-trifluorophenyl-L-alanine (Tfpa or (3,4,5-trifluoro-)F) | 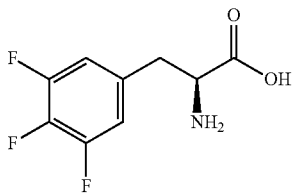 [SMILES: N[C@@H](Cc1cc(F)c(F)c(F)c1)C(=O)O] |
| (S)-β-cyclohexylalanine (Cha) | 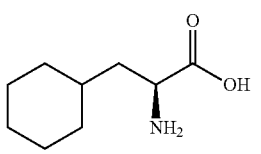 [SMILES: N[C@@H](CC1CCCCC1)C(=O)O] |
| Naphthyl-L-alanine (Nal) may refer to: 3-(1-naphthyl)-L-alanine and 3-(2-naphthyl)-L-alanine | 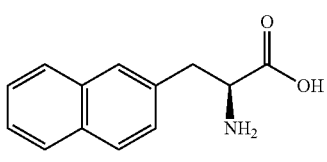 and 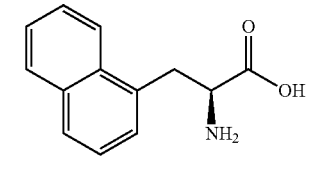 |
| 4-chlorophenyl-L-alanine (4cpa) | 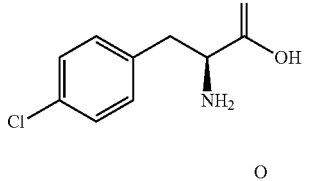 |
| 4-methoxyphenyl-L-alanine | 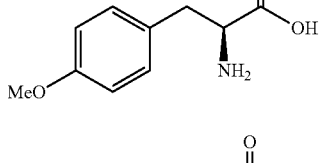 |
| 4-methylphenyl-L-alanine | 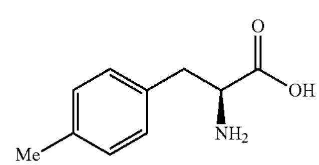 [SMILES: Cc1ccc(C[C@H](N)C(=O)O)cc1] |

-continued

| Name | Structure |
|---|---|
| 3-(4-pyridyl)-L-alanine | 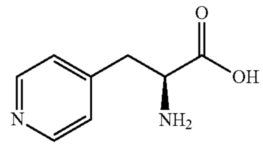 [SMILES: N[C@@H](Cc1ccncc1)C(=O)O] |
| 3-(3-pyridyl)-L-alanine | 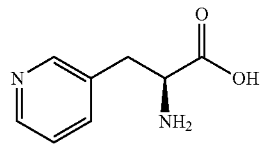 [SMILES: N[C@@H](Cc1cccnc1)C(=O)O] |
| 3-(2-pyridyl)-L-alanine | 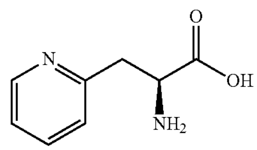 [SMILES: N[C@@H](Cc1ccccn1)C(=O)O] |
| D-(−)-a-Phenylglycine | 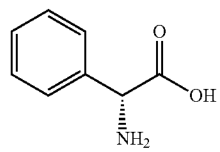 |
| Homophenylalanine | 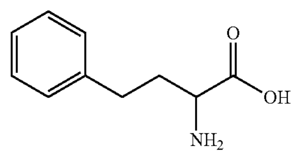 [SMILES: NC(CCc1ccccc1)C(=O)O] |
| 3-styryl-L-alanine | 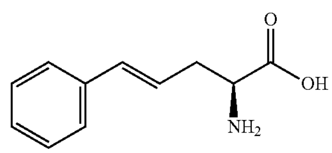 [SMILES: N[C@@H](C/C=C/c1ccccc1)C(=O)O] |
| O-Benzyl-L-tyrosine | 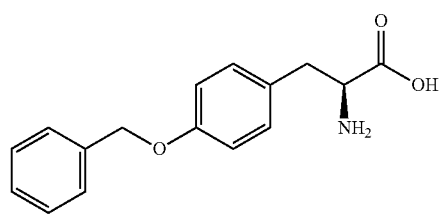 [SMILES: N[C@@H](Cc1ccc(OCc2ccccc2)cc1)C(=O)O] |
| 4-benzoyl-L-phenylalanine | 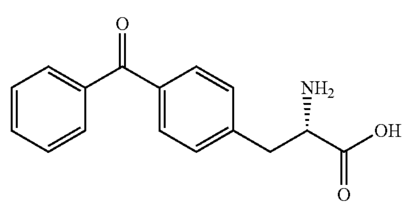 [SMILES: N[C@@H](Cc1ccc(C(=O)c2ccccc2)cc1)C(=O)O] |
| α-Methyl-DL-phenylalanine | 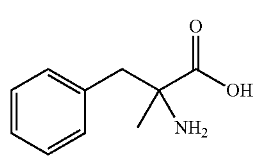 |

-continued

| Name | Structure |
|---|---|
| Aminoindane | (structure: indane with NH$_2$ and COOH at 1-position) |

A more comprehensive list is shown here:

| Name | Structure |
|---|---|
| 3,4,5-trifluorophenyl-L-alanine (Tfpa or (3,4,5-trifluoro-)F) | (structure) |
| (S)-β-cyclohexylalanine (Cha) | (structure) |
| Naphthyl-L-alanine (Nal) may refer to: 3-(1-naphthyl)-L-alanine and 3-(2-naphthyl)-L-alanine | (structure of 3-(2-naphthyl)-L-alanine) and (structure of 3-(1-naphthyl)-L-alanine) |
| 4-chlorophenyl-L-alanine (4cpa) | (structure) |
| 4-methoxyphenyl-L-alanine | (structure) |
| 4-methylphenyl-L-alanine | (structure) |

-continued

| Name | Structure |
|---|---|
| 3-(4-pyridyl)-L-alanine | 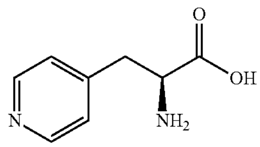 [SMILES: N[C@@H](Cc1ccncc1)C(=O)O] |
| 3-(3-pyridyl)-L-alanine | 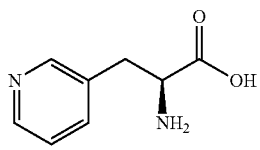 [SMILES: N[C@@H](Cc1cccnc1)C(=O)O] |
| 3-(2-pyridyl)-L-alanine | 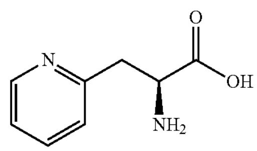 [SMILES: N[C@@H](Cc1ccccn1)C(=O)O] |
| D-(−)-α-Phenylglycine | 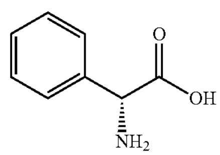 [SMILES: N[C@@H](C(=O)O)c1ccccc1] |
| Homophenylalanine | 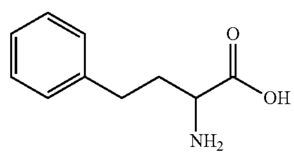 [SMILES: NC(CCc1ccccc1)C(=O)O] |
| 3-styryl-L-alanine | 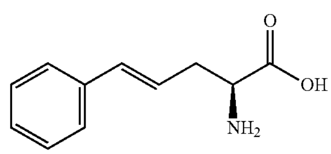 [SMILES: N[C@@H](C/C=C/c1ccccc1)C(=O)O] |
| O-Benzyl-L-tyrosine | 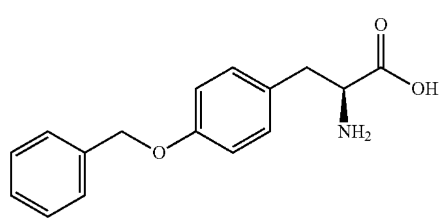 [SMILES: N[C@@H](Cc1ccc(OCc2ccccc2)cc1)C(=O)O] |
| 4-benzoyl-L-phenylalanine | 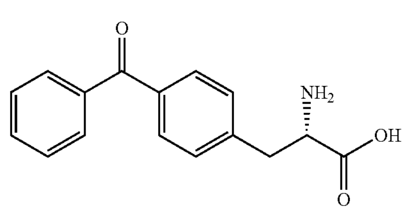 [SMILES: N[C@@H](Cc1ccc(C(=O)c2ccccc2)cc1)C(=O)O] |
| α-Methyl-DL-phenylalanine | 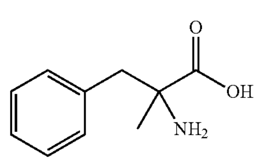 |

| Name | Structure |
|---|---|
| Aminoindane | (indane with NH₂ and COOH at 1-position) |
| 4-Aminopiperidine-4-carboxylic acid | HOOC, NH₂ on piperidine 4-position |
| (Alpha-Methyl-L-phenylalanine) | (phenylalanine with α-methyl, OH, NH₂) |

As used herein, and unless otherwise defined, K(GluPAL) refers to Lysine substituted by palmitic acid with a glutamic acid spacer. As used herein, and unless otherwise defined, K(PAL) refers to Lysine substituted with palmitic acid. As used herein, and unless otherwise defined, PAL refers to palmitic acid.

For any of the natural or modified amino acids described herein, for instance those corresponding to each of $X^1$-$X^{14}$, it is to be understood that the —NH₂ and —CO₂H moieties depicted may not be present in their entirety in the compounds of the invention as they may contribute to the formation of one or more of the linkages $L_1$-$L_{14}$ and/or conjugation linkers $L_c$ also described herein. For example, the —NH₂ moiety of one natural or modified amino acid may combine with the —CO₂H moiety of a neighbouring natural or modified amino acid to form an amide linkage.

For any of the natural or modified amino acids described herein, for instance those corresponding to each of $X^1$-$X^{14}$ in the compounds of Formula I, it is to be understood that one or more atoms depicted may not be present as they may contribute to the formation of one or more conjugation linkers $L_c$ described herein.

For example, a cysteine may be conjugated to:
a) a maleimide, a heterobifunctional maleimide cross-linker, a maleimide conjugated to a fatty acid, a pegylated maleimide linker; and/or
b) linked to another moiety via an iodoacetamide, a 2-thiopyridine, a 3-arylpropiolonitrile a 3-mercaptopropanoic acid moiety, or a thioether moiety by replacement of the hydrogen atom of the thiol moiety.

In another example a suitably functionalised amino acid side-chain (e.g. arginine or lysine) may be conjugated by e.g. a peptidyl linker or a non-peptidyl linker (e.g. using click chemistry), an amide linker or a linker comprising a polyethylene glycol polymer or fatty acid. For other suitable amino acid side-chains such as arginine or lysine a suitable modification is optionally alkylation (mono- or di- or $C_2$-$C_6$ chains), esterification, N-alkyl amidation, or substitution of hydrogen with any alkane, halo group or hydroxyl group.

In another example an aspartic acid side chain may be conjugated by an amide linker, a carbamate, a thioamide, an ester or other suitable linker.

Examples of modified amino acids include but are not limited to hydroxyproline, carboxyglutamate, O-phosphoserine, azetidinecarboxyllic acid, 2-aminoadipic acid, 3-aminoadipic acid, beta-alanine, aminopropionic acid, 2-aminobutyric acid (Abu), 4-aminobutyric acid, 6-aminobutyric acid, 2-aminoglutaric acid, 2-aminoheptanoic acid, 2-aminoisobutyric acid (Aib), 3-aminoisobutyric acid, 2-aminopimelic acid, tertiatry-butylglycine, 2,4-diaminoisobutyric acid, desmosine, 2.2'-diaminopimelic acid, 2,3-diaminopropionic acid, N-ethylglycine, N-methylglycine, N-methylisoleucine, N-methylpentylglycine, N-methylvaline, naphthaline, norvaline, norleucine (Nle), ornithine, pentylglycine, pipecolic acid, 5-oxopyrrolidine-2-carboxylic acid (Glp or Pyr or pE), and thioproline. Amino acids also include naturally occurring amino acids in certain organisms such as ornithine, D-ornithine and D-arginine.

| Code | Modified amino acid | Structure |
|---|---|---|
| Abu | (S)-2-Aminobutyric acid | (structure with NH₂, OH, CH₃) |
| Aib | 2-Aminoisobutyric acid | (structure with two methyls, NH₂, OH) |
| Nle | Norleucine ((2S)-2-Aminohexanoic acid) | (structure with NH₂, OH, butyl chain) |

| Code | Modified amino acid | Structure |
| --- | --- | --- |
| Glp/Pyr/pE | (2S)-5-Oxopyrrolidine-2-carboxylic acid | 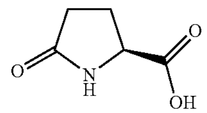 |

It will be apparent to those skilled in the art that any amino acid displayed or recited in any of the above tables or lists can also be selected as the opposite enantiomer, or any diastereomer (if applicable), or as the racemate, and be employed in compounds of the invention.

As used herein, "modification" refers to the replacement of at least part of a compound such as an amino acid for an alternative moiety. Examples of modifications include alkylation, esterification, N-alkyl amidation, or substitution of hydrogen with any halo group or hydroxyl group. The term "modification" also encompasses the conjugation of any of $X^1$-$X^{14}$ in the compounds of Formula I to a compound such as $R^3$ through a conjugation linker $L_c$. For example, a cysteine at $X^1$, $X^6$, $X^9$ or $X^{14}$ in Formula I may be modified by conjugation to a compound $R^3$ through a conjugation linker $L_c$, optionally wherein the conjugation linker $L_c$ is a maleimide, a pegylated maleimide, or a fatty acid.

Any amino acid forming part of a compound of this invention by one or more linkages can be subject to modification. For example, a natural amino acid can be subject to modification, and a modified amino acid can be subject to modification.

In some embodiments, each $R^3$ is a fatty acid independently such as a myristic, palmitic, stearic, oleic, linoleic, linolenic or a conjugated or saturated or branched derivative. In some embodiments, $R^3$ is a pegylated moiety such as PEG1-20 but preferably PEG1-10, PEG-NHS ester, PEG-PFP ester, PEG-t-butyl ester, PEG-alcohol, PEG-amine, amido-PEG-acid. In some embodiments, $R^3$ is a pegylated moiety such as a 5 kDa, 10 kDa, or 20 kDa polyethylene glycol polymer. For example, the term '20 kDa' polyethylene glycol polymer is an average $M_n$ 20,000 polymer.

PEG refers to polyethylene glycol. For example, PEG1-20 can comprise 1-20 units of polymerised ethylene glycol. For example, PEG1-10 can comprise 1-10 units of polymerised ethylene glycol. A PEG-NHS ester can comprise an N-hydroxysuccinimide ester group, a PEG-PFP ester can comprise a pentafluorophenyl ester group, and a PEG-t-butyl ester can comprise a t-butyl ester group. Alcohol, amine, amido, and acid, refer to those functional groups at one or both ends of the PEG molecule. In some embodiments PEG can also be a 5 kDa, 10 kDa, or 20 kDa polyethylene glycol polymer. For example, the term '20 kDa' polyethylene glycol polymer is an average $M_n$ 20,000 polymer.

Also encompassed by the term "modification" are conservative substitutions, for example according to the following table. Amino acids in the same block in the second column and preferably in the same line in the third column may be substituted for each other:

| Aliphatic | Non-polar | G A P |
| --- | --- | --- |
| | | I L V |
| | Polar-uncharged | C S T M |
| | | N Q |
| | Polar-charged | D E |
| | | K R |
| Aromatic | | H F W Y |

In some embodiments of the invention a natural amino acid can be modified wherein the modification comprises substituting the amino acid in question for a different amino acid in the same block in the second column of the table above, preferably for a different amino acid in the same line in the third column of the table above.

As used herein, "a linkage" refers to any moiety suitable for joining two amino acids together. Examples of suitable linkages include an amide bond, N-methylated amide, urea, ester, carbamate, peptoid, sulphonamide, alkene, thioamide, thioether, fluoroalkene, azapeptide, difluoroketone or epoxide.

As used herein, "a conjugation linker" refers to any moiety suitable for joining the amino acid of $X^1$ to the rest of the compound as represented by $R^1$, or any moiety suitable for joining the amino acid of $X^{14}$ to the rest of the compound as represented by $R^2$, or any moiety suitable for joining any of $X^1$ to $X^{14}$ in the compounds of Formula I to the rest of the compound as represented by $R^3$.

Examples of suitable conjugation linkers include a linker that comprises either a 3-mercaptopropanoic acid moiety, a maleimide moiety, a pegylated maleimide moiety, or thioether moiety, or is a peptidyl linker, a non-peptidyl linker (e.g. using click chemistry), an amide linker or a linker comprising a polyethylene glycol polymer linker.

As used herein, "pharmaceutically acceptable" refers to compounds; materials, compositions, and/or dosage forms which are, within the scope of sound medical judgment, suitable for contact with the tissues of human beings and animals without severe toxicity, irritation, allergic response, or other complications, commensurate with a benefit to-risk ratio that is reasonable for the medical condition being treated.

As used herein, "pharmaceutically acceptable salts" refers to derivatives of compounds wherein the parent compound is modified by making acid or base salts thereof. Examples of pharmaceutically acceptable salts include, but are not limited to, mineral or organic acid salts of basic residues such as amines, alkali or organic salts of acidic residues, such as carboxylic acids, and the like. The pharmaceutically acceptable salts include the conventional non-toxic salts or the quaternary ammonium salts of the parent compound formed, for example, from non-toxic inorganic or organic acids. For instance, such conventional non-toxic salts include those derived from inorganic acids such as hydrochloric, hydrobromic, sulfuric, sulfamic, phosphoric, nitric acids and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic acids, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine. Thus, a pharmaceutically acceptable salt can be formed from a compound of the invention having either acidic, basic or both functional groups. For example, a peptide having a carboxylic acid group may, in the presence of a pharmaceutically suitable base, form a carboxylate anion paired with a cation such as a sodium or potassium cation. Similarly, a peptide having an amine functional group may, in the presence of a pharmaceutically suitable acid such as HCl, form a salt. One example of a pharmaceutically acceptable solvate of a compound is a combination of a compound with solvent molecules which yields a complex of such solvent molecules in association with the compound. Particularly suitable hydrates of compounds are such hydrates which either have comparable activity or hydrates which are converted back to the active compound following administration. A pharmaceutically acceptable N-oxide of a compound which contains an amine is such a compound wherein the nitrogen atom of the amine is bonded to an oxygen atom.

Compounds of the Invention

The compound of the invention may be a pro-drug. A pro-drug of a compound of the invention includes pharmaceutically acceptable derivatives which upon administration can convert through metabolism or other process to a biologically active form of the compound. Pro-drugs are particularly desirable where the pro-drug has more favourable properties than does the active compound with respect to bioavailability, stability or suitability for a particular formulation.

A pharmaceutically acceptable crystalline, isomorphic crystalline or amorphous form of the compound of the invention can be any crystalline or non-crystalline form of a pharmaceutically acceptable acidic, basic, zwitterionic, salt, hydrate or any other suitably stable, physiologically compatible form of the compound of the invention.

Modes of Administration

The pharmaceutical compositions of the invention can be delivered or administered intravenously, transdermally, transmucosally, intranasally, subcutaneously, intramuscularly, orally or topically (such as for example to the eye). The compositions can be administered for prophylactic treatment of individuals suffering from, or at risk of a disease or a disorder. For therapeutic applications, a pharmaceutical composition is typically administered to a subject suffering from a disease or disorder, in an amount sufficient to inhibit, prevent, or ameliorate the disease or disorder. An amount adequate to accomplish this is defined as a "therapeutically effective dose."

As used herein, local application or administration refers to administration of a pharmaceutical composition according to the invention to the site of a cancer or tumor, or alternatively for example where the tumor has been excised. Application may be via injection, catheter or delivery as part of a biocompatible device or material. Thus, local application refers to application to a discrete internal area of the body, such as, for example, a soft tissue area (such as muscle, intraocular, brain, kidney, lung etc. or other fleshy internal areas), or other internal area of the body where the compound can have local or systemic beneficial effects.

The compound of the invention may be administered all at once, or may be divided into a number of smaller doses to be administered at intervals of time, or as a controlled release formulation.

Compositions

According to a further aspect of the invention there is provided a composition comprising a compound of the present invention by itself or in conjunction with a pharmaceutically acceptable diluent, excipient, or carrier.

The compounds of the invention can be incorporated into pharmaceutical compositions. The compositions can include an effective amount of the compound in a pharmaceutically acceptable diluent, excipient or carrier. Conventional excipients, carriers and/or diluents for use in pharmaceutical compositions are generally inert and make up the bulk of the preparation. In a particular embodiment, the compound is an apelin antagonist.

The pharmaceutical excipient or carrier can be any compatible, non-toxic substance suitable as a vehicle for delivery the compound of the invention. Suitable excipients or carriers include, but are not limited to, sterile water (preferably pyrogen-free), saline, phosphate-buffered saline (PBS), water/ethanol, water/glycerol, water/sorbitol, water/polyethylene glycol, propylene glycol, cetylstearyl alcohol, carboxymethylcellulose, corn starch, lactose, glucose, microcrystalline cellulose, magnesium stearate, polyvinylpyrrolidone (PVP), citric acid, tartaric acid, oils, fatty substances, waxes or suitable mixtures of any of the foregoing.

The pharmaceutical composition according to the invention can be formulated as a liquid, semisolid or solid dosage form. For example the pharmaceutical composition can be in the form of a solution for injection, drops, syrup, spray, suspension, tablet, patch, capsule, dressing, suppository, ointment, cream, lotion, gel, emulsion, aerosol or in a particulate form, such as pellets or granules, optionally pressed into tablets or lozenges, packaged in capsules or suspended in a liquid. The tablets can contain binders, lubricants, diluents, coloring agents, flavoring agents, wetting agents and may be enteric-coated to survive the acid environment of the stomach and dissolve in the more alkaline conditions of the intestinal lumen. Alternatively, the tablets can be sugar-coated or film coated with a water-soluble film. Pharmaceutically acceptable adjuvants, buffering agents, dispersing agents, and the like, may also be incorporated into the pharmaceutical compositions.

Binders include for instance, starch, mucilage, gelatin and sucrose. Lubricants include talc, lycopodium, magnesium and calcium stearate/stearic acid. Diluents include lactose, sucrose, mannitol, salt, starch and kaolin. Wetting agents include propylene glycol and sorbitan monostearate.

For oral administration, an active ingredient can be formulated as solid dosage forms, such as capsules, tablets, and powders, or in liquid dosage forms, such as elixirs, syrups, and suspensions. Active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours or days Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance. To facilitate drug stability and absorption, peptides of the invention can be released from a capsule after passing through the harsh proteolytic environment of the stomach. Methods for enhancing peptide stability and absorption after oral administration are well known in the art (e.g., Mahato R I. Emerging trends in oral delivery of peptide and protein drugs. Critical Reviews in Therapeutic Drug Carrier Systems. 20:153-214, 2003).

Dosage forms such as lozenges, chewable tablets and chewing gum permit more rapid therapeutic action compared to per-oral dosage forms of the compounds of the invention having significant buccal absorption. Chewing gum formulations are solid, single dose preparations with a base consisting mainly of gum, that are intended to be chewed but not swallowed, and contain one or more compounds of the invention which are released by chewing and are intended to be used for local treatment of pain and inflammation of the mouth or systemic delivery after absorption through the buccal mucosa. See for example, U.S. Pat. No. 6,322,828 to Athanikar and Gubler entitled: Process for manufacturing a pharmaceutical chewing gum.

For nasal administration, the compounds of the invention can be formulated as aerosols. The term "aerosol" includes any gas-borne suspended phase of the compounds of the instant invention which is capable of being inhaled into the bronchioles or nasal passages. Specifically, aerosol includes a gas-borne suspension of droplets of the compounds of the instant invention, as may be produced in a metered dose inhaler or nebulizer, or in a mist sprayer. Aerosol also includes a dry powder composition of a compound of the instant invention suspended in air or other carrier gas, which may be delivered by insufflation from an inhaler device, for example. See Ganderton & Jones, Drug Delivery to the Respiratory Tract, Ellis Horwood (1987); Gonda (1990) Critical Reviews in Therapeutic Drug Carrier Systems 6:273-313; and Raeburn et al. (1992) J. Pharmacol. Toxicol. Methods 27:143-159.

The pharmaceutical compositions of the invention can be prepared in a formulation suitable for systemic delivery, such as for instance by intravenous, subcutaneous, intramuscular, intraperitoneal, intranasal, transdermal, intravaginal, intrarectal, intrapulmonary or oral delivery. Alternatively, the pharmaceutical compositions of the invention can be suitably formulated for local delivery, such as, for instance, for topical, or iontophoretic delivery, or for transdermal delivery by a patch coated, diffused or impregnated with the formulation, and local application to the joints, such as by intra-articular injection.

Preparations for parenteral administration include sterile solutions ready for injection, sterile dry soluble products ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous, and thereby formulated for delivery by injection, infusion, or using implantable pumps. For intravenous, subcutaneous, and intramuscular administration, useful formulations of the invention include microcapsule preparations with controlled release properties (R. Pwar et al. Protein and peptide parenteral controlled delivery. Expert Opin Biol Ther. 4(8): 1203-12, 2004) or encapsulation in liposomes, with an exemplary form being polyethylene coated liposomes, which are known in the art to have an extended circulation time in the vasculature (e.g. Koppal, T. "Drug delivery technologies are right on target", Drug Discov. Dev. 6, 49-50, 2003).

Preparations for transdermal delivery are incorporated into a device suitable for said delivery, said device utilizing, e.g., iontophoresis (Kalia Y N et al. Iontophoretic Drug Delivery. Adv Drug Deliv Rev. 56:619-58, 2004) or a dermis penetrating surface (Prausnitz M R. Microneedles for Transdermal Drug Delivery. Adv Drug Deliv Rev. 56:581-7, 2004), such as are known in the art to be useful for improving the transdermal delivery of drugs. An electrotransport device and methods of operation thereof are disclosed in U.S. Pat. No. 6,718,201. Methods for the use of iontophoresis to promote transdermal delivery of peptides are disclosed in U.S. Pat. Nos. 6,313,092 and 6,743,432.

Other useful transdermal delivery devices employ high velocity delivery under pressure to achieve skin penetration without the use of a needle. Transdermal delivery can be improved, as is known in the art, by the use of chemical enhancers, sometimes referred to in the art as "permeation enhancers", i.e., compounds that are administered along with the drug (or in some cases used to pretreat the skin, prior to drug administration) in order to increase the permeability of the stratum corneum, and thereby provide for enhanced penetration of the drug through the skin. Chemical penetration enhancers are compounds that are innocuous and serve merely to facilitate diffusion of the drug through the stratum corneum, whether by passive diffusion or an energy driven process such as electrotransport. See, for example, Meidan V M et al. Enhanced iontophoretic delivery of buspirone hydrochloride across human skin using chemical enhancers. Int. J. Pharm. 264:73-83, 2003.

Pharmaceutical dosage forms for rectal administration include rectal suppositories, capsules and tablets for systemic effect. Rectal suppositories as used herein mean solid bodies for insertion into the rectum which melt or soften at body temperature releasing one or more pharmacologically or therapeutically active ingredients. Pharmaceutically acceptable substances utilized in rectal suppositories include bases or vehicles and agents that raise the melting point of the suppositories. Examples of bases include cocoa butter (theobroma oil), glycerin-gelatin, carbowax, (polyoxyethylene glycol) and appropriate mixtures of mono-, di- and triglycerides of fatty acids. Combinations of the various bases can also be used. Agents that raise the melting point of suppositories include spermaceti and wax. Rectal suppositories may be prepared either by the compression method or by molding. Rectal suppositories typically weigh about 2 gm to about 3 gm. Tablets and capsules for rectal administration are manufactured using the same pharmaceutically acceptable substance(s) and by the same methods as for formulations for oral administration.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include sodium chloride for injection, Ringers solution for injection, isotonic dextrose for injection, sterile water for injection, dextrose and lactated Ringers solution for injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfite. Local anesthetics include procaine hydrochloride. Suspending and dispersing agents include sodium carboxymethylceluose, hydroxypropyl methylcellulose and polyvinylpyrrolidone. Emulsifying agents include Polysorbate 80 (Tween 80). A sequestering or chelating agent of metal ions such as EDTA can also be incorporated. Pharmaceutical carriers also include ethyl alcohol, polyethylene glycol and propylene glycol for water miscible vehicles and the pH can be adjusted to a physiologically compatible pH by addition of sodium hydroxide, hydrochloric acid, citric acid or lactic acid.

The term "controlled release formulation" encompasses formulations that allow the continuous delivery of compound of the invention to a subject over a period of time, for example, several days to weeks. Such formulations may be administered subcutaneously or intramuscularly and may allow for the continual steady state release of a predetermined amount of compound in the subject over time. The controlled release formulation of the compounds of the invention may be, for example, a formulation of drug containing polymeric microcapsules, such as those described in U.S. Pat. Nos. 4,677,191 and 4,728,721, incorporated herein by reference. The concentration of the pharmaceutically active compound is adjusted so that administration provides an effective amount to produce a desired effect. The exact dose depends on the age, weight and condition of the patient or animal, as is known in the art. For any particular subject, specific dosage regimens can be adjusted over time according to the individual need and the professional judgment of the person administering or supervising the administration of the formulations. Thus, the concentration ranges set forth herein are exemplary only and are not intended to limit the scope or practice of the claimed invention. The unit dose parenteral preparations include packaging in an ampoule or prepackaged in a syringe with, or without a needle for delivery. All preparations for parenteral administration are typically sterile, as is practiced in the art. Illustratively, intravenous infusion of a sterile aqueous buffered solution containing an active compound is an effective mode of administration. In another embodiment a sterile aqueous or oily solution or suspension containing the active material can be injected as necessary to produce the desired pharmacological effect.

Therapeutic Applications

The invention further provides methods of treating a disease or condition, comprising administering to a mammal in need thereof a therapeutically effective amount of one or more compounds or pharmaceutical compositions of the invention.

In an embodiment, the mammal is a human patient/subject.

Examples of diseases and disorders which can be treated using the compounds of the invention are set out below.

The compounds of the invention are antagonists of the apelin receptor and may have therapeutic applications in any disease that has as a component apelin receptor activity.

For example, the compounds of the present invention may have therapeutic applications in the treatment of a disorder or disease selected from the group consisting of a tumor, cancer, metabolic diseases, diabetes, diseases involving angiogenesis and lymphangiogenesis, diseases of obesity including reduction of dietary sugar uptake, cardiovascular disease, neoplasia, peripheral vascular disease, septic shock, hypotension, preeclampsia, ocular degeneration, idiopathic pulmonary fibrosis, inflammatory disease (such as arthritis and inflammatory bowel disease), avascular or ischemic insult, eczema, ulcers, lymphedema, bone diseases, vascular hyperplasia, hemangioma, proteinuric renal disease, diabetic retinopathy, diseases of choroidal vasculature (AMD), macular degenerative disease, psoriasis, endometriosis, glioma, glioblastoma, glioblastoma multiforma, colorectal cancer, renal carcinoma, lung cancer, mammary/breast cancer, endometriosis, any disease involving angiogenesis, and HIV infection.

Wherein the terms 'mammary cancer' and 'breast cancer' are used interchangeably. A patient having a malignant 'mammary tumor' is equivalent to the patient having breast cancer.

In one embodiment, the compounds of the invention may be used in the treatment of glioblastoma, preferably glioblastoma multiforma.

In one embodiment, the compounds of the invention may be used in the treatment of glioma, preferably astrocytoma, oligodendroglioma, or ependymoma.

In one embodiment, the compounds of the invention may be used in the treatment of colorectal cancer.

In one embodiment, the compounds of the invention may be used in the treatment of renal carcinoma.

In one embodiment, the compounds of the invention may be used in the treatment of ocular degeneration.

In one embodiment, the compounds of the invention may be used in the treatment of diabetic retinopathy.

In another embodiment, provided is a method of treating a tumor or disease caused by abnormal angiogenesis in a patient in need thereof, comprising administrating to the patient a therapeutically effective amount of a compound as provided herein In another embodiment, administration of the compound modifies tumor cell growth or endothelial cell growth in the patient by virtue of inhibition of the effects of apelin as a sustaining endocrine factor.

In one embodiment, administration of the compound modifies tumor cell growth or endothelial cell growth in the patient, thereby treating the tumor.

In certain embodiments, the tumor or disease caused by abnormal angiogenesis is cancer. However, abnormal angiogenesis is not limited to cancer. Other diseases, including macular degeneration, are linked to abnormal development of blood vessels.

Methods of Treatment

In a further aspect, the present invention provides a compound or composition of the invention for use in medicine.

In a further aspect, the present invention provides a compound or composition of the invention for use in the treatment of a disorder or disease selected from the group consisting of a tumor, cancer, metabolic diseases, diabetes, diseases involving angiogenesis and lymphangiogenesis, diseases of obesity including reduction of dietary sugar uptake, cardiovascular disease, neoplasia, peripheral vascular disease, septic shock, hypotension, preeclampsia, ocular degeneration, idiopathic pulmonary fibrosis, inflammatory disease (such as arthritis and inflammatory bowel disease), avascular or ischemic insult, eczema, ulcers, lymphedema, bone diseases, vascular hyperplasia, hemangioma, proteinuric renal disease, diabetic retinopathy, diseases of choroidal vasculature (AMD), macular degenerative disease, psoriasis, endometriosis, glioma, glioblastoma, glioblastoma multiforma, colorectal cancer, renal carcinoma, lung cancer, mammary/breast cancer, endometriosis, any disease involving angiogenesis, and HIV infection.

In some embodiments a compound or composition of the invention can be for use in the treatment of a disorder or disease selected from the group consisting of cancer, colorectal cancer, lung cancer, mammary/breast cancer, glioma, glioblastoma, glioblastoma multiforma, renal carcinoma, ocular degeneration, and/or diabetic retinopathy.

In some embodiments a compound or composition of the invention can be for use in the treatment of cancer in a patient.

In some embodiments a compound or composition of the invention can be for use in the treatment of glioblastoma, preferably glioblastoma multiforma in a patient.

In some embodiments a compound or composition of the invention can be for use in the treatment of glioblastoma in a patient.

In some embodiments a compound or composition of the invention can be for use in the treatment of lung cancer in a patient.

In some embodiments a compound or composition of the invention can be for use in the treatment of mammary/breast cancer in a patient.

In some embodiments a compound or composition of the invention can be for use in the treatment of endometriosis in a patient.

In some embodiments a compound or composition of the invention can be for use in the treatment of colorectal cancer in a patient.

In some embodiments a compound or composition of the invention can be for use in the treatment of renal carcinoma in a patient.

In some embodiments a compound or composition of the invention can be for use in the treatment of ocular degeneration in a patient.

In some embodiments a compound or composition of the invention can be for use in the treatment of diabetic retinopathy in a patient.

In some embodiments a compound or composition of the invention can be for use in the treatment of a tumor or disease caused by abnormal angiogenesis in a patient in need thereof, optionally wherein administration of the compound modifies tumor cell growth or endothelial growth in the patient.

In a further aspect, the present invention provides a method of treating disease or disorder in a patient, said method comprising administering a compound or a composition of the invention to said patient.

In some embodiments the present invention provides a method of treating a tumor, cancer, metabolic diseases, diabetes, diseases involving angiogenesis and lymphangiogenesis, diseases of obesity including reduction of dietary sugar uptake, cardiovascular disease, neoplasia, peripheral vascular disease, septic shock, hypotension, preeclampsia, ocular degeneration, idiopathic pulmonary fibrosis, inflammatory disease (such as arthritis and inflammatory bowel disease), avascular or ischemic insult, eczema, ulcers, lymphedema, bone diseases, vascular hyperplasia, hemangioma, proteinuric renal disease, diabetic retinopathy, diseases of choroidal vasculature (AMD), macular degenerative disease, psoriasis, endometriosis, glioma, glioblastoma, glioblastoma multiforma, colorectal cancer, renal carcinoma, lung cancer, mammary/breast cancer, endometriosis, any disease involving angiogenesis, and HIV infection, said method comprising administering a compound a composition of the invention to said patient.

In some embodiments the present invention provides a method of treating cancer, colorectal cancer, lung cancer, mammary cancer, glioblastoma, glioblastoma multiforma, renal carcinoma, ocular degeneration, and/or diabetic retinopathy in a patient, said method comprising administering a compound or a composition of the invention to said patient.

In some embodiments the present invention provides a method of treating glioblastoma, preferably glioblastoma multiforma in a patient, said method comprising administering a compound or a composition of the invention to said patient.

In some embodiments the present invention provides a method of treating glioblastoma, preferably lung cancer in a patient, said method comprising administering a compound or a composition of the invention to said patient.

In some embodiments the present invention provides a method of treating glioblastoma, preferably mammary/breast cancer in a patient, said method comprising administering a compound or a composition of the invention to said patient.

In some embodiments the present invention provides a method of treating endometriosis in a patient, said method comprising administering a compound or a composition of the invention to said patient.

In some embodiments the present invention provides a method of treating colorectal cancer in a patient, said method comprising administering a compound or a composition of the invention to said patient.

In some embodiments the present invention provides a method of treating renal carcinoma in a patient, said method comprising administering a compound or a composition of the invention to said patient.

In some embodiments the present invention provides a method of treating ocular degeneration in a patient, said method comprising administering a compound or a composition of the invention to said patient.

In some embodiments the present invention provides a method of treating diabetic retinopathy in a patient, said method comprising administering a compound or a composition of the invention to said patient.

In some embodiments the present invention provides a method of treating a tumor or disease caused by abnormal angiogenesis in a patient in need thereof, optionally wherein administration of the compound modifies tumor cell growth or endothelial growth in the patient, said method comprising administering a compound or a composition of the invention to said patient.

In a further aspect, the present invention provides a use of a substance or composition of the invention for the manufacture of a medicament for the treatment or a disease or disorder selected from a tumor, cancer, metabolic diseases, diabetes, diseases involving angiogenesis and lymphangiogenesis, diseases of obesity including reduction of dietary sugar uptake, cardiovascular disease, neoplasia, peripheral vascular disease, septic shock, hypotension, preeclampsia, ocular degeneration, idiopathic pulmonary fibrosis, inflammatory disease (such as arthritis and inflammatory bowel disease), avascular or ischemic insult, eczema, ulcers, lymphedema, bone diseases, vascular hyperplasia, hemangioma, proteinuric renal disease, diabetic retinopathy, diseases of choroidal vasculature (AMD), macular degenerative disease, psoriasis, endometriosis, glioma, glioblastoma, glioblastoma multiforma, colorectal cancer, renal carcinoma, lung cancer, mammary/breast cancer, endometriosis, any disease involving angiogenesis, and HIV infection.

In a further aspect, the present invention includes a method for treating a tumor in a human or animal subject comprising the steps of:
  a) identifying the human or animal subject in need of treatment of a tumor
  b) determining sensitivity of the mammal to treatment with an apelin receptor antagonist according to the present invention
  c) administering a therapeutically effective amount of said apelin receptor antagonist to the subject.

In one embodiment of the present invention, the tumor is a glioblastoma.

In one embodiment the invention provides a method of inhibiting growth, invasion and/or proliferation of tumor cells in a subject, wherein the method comprises administering an apelin receptor antagonist of the present invention to the subject in need thereof.

Co-Therapy

An apelin receptor antagonist can be beneficial when administered in combination with one or more anti-cancer or therapeutic agents. Examples include the chemotherapeutic agents selected from the group consisting of temozolomide, etoposide, doxorubicin, cisplatin, paclitaxel, carmustine, lomustine, ceramide and phosphorylcholine.

An apelin receptor antagonist can be beneficial when administered in combination with an anti-angiogenesis inhibitor. [WO 2017174758 A1]

In a further aspect, the invention provides a compound or composition of the invention can be for use in the treatment of a tumor in a subject, said method comprising the steps of:
a) identifying the human or animal subject in need of treatment of a tumor
b) determining sensitivity of the mammal to treatment with an apelin receptor antagonist according to the present invention
c) administering a therapeutically effective amount of said apelin receptor antagonist to the subject.

In some embodiments the tumor is a glioblastoma.

In a further aspect, the invention provides a compound or composition of the invention, for use in the treatment of inhibiting growth, invasion and/or proliferation of tumor cells in a subject, wherein said method comprises administering said compound to the subject in need thereof.

In some embodiments the treatment comprises administering the compound or composition to the patient intravenously.

In some embodiments the treatment comprises administering the compound or composition to a patient who has undergone tumor excision surgery and wherein the compound or composition is administered at the site of tumor excision.

In some embodiments the treatment comprises administering the compound or composition to the patient in combination with one or more additional anti-cancer agents.

In some embodiments the compound or composition and said one or more anti-cancer agents are each administered to the patient simultaneously, separately, or sequentially.

In some embodiments the one or more anti-cancer agents are selected from the group consisting of bevacizumab, temozolomide, vincristine, irinotecan, procarbazine, BiCNU, and carmustine.

In some embodiments the anti-cancer agent is temozolomide.

In some embodiments the anti-cancer agents are chemotherapeutic agents.

In some embodiments the chemotherapeutic agents are selected from the group consisting of temozolomide, etoposide, doxorubicin, cisplatin, paclitaxel, carmustine, lomustine, ceramide and phosphorylcholine and other suitable anti-cancer agents including kinase inhibitors.

In some embodiments the treatment further comprises subjecting the patient to radiation therapy.

In a further aspect, the invention provides a method of treating a tumor in a subject, said method comprising the steps of:
a) identifying the human or animal subject in need of treatment of a tumor
b) determining sensitivity of the mammal to treatment with an apelin receptor antagonist according to the present invention
c) administering a therapeutically effective amount of said apelin receptor antagonist to the subject.

In some embodiments the tumor is a glioblastoma.

In a further aspect, the invention provides a method of inhibiting growth, invasion and/or proliferation of tumor cells in a subject, wherein said method comprises administering a compound or a composition of the invention to the subject in need thereof.

In some embodiments the method comprises administering the compound or composition to the patient intravenously.

In some embodiments the method comprises administering the compound or composition to a patient who has undergone tumor excision surgery and wherein the compound or composition is administered at the site of tumor excision.

In some embodiments the method comprises administering the compound or composition to the patient in combination with one or more additional anti-cancer agents.

In some embodiments the compound or composition and the one or more anti-cancer agents are each administered to the patient simultaneously, separately, or sequentially.

In some embodiments the one or more anti-cancer agents are selected from the group consisting of bevacizumab, temozolomide, vincristine, irinotecan, procarbazine, BiCNU, and carmustine.

In some embodiments the anti-cancer agent is temozolomide.

In some embodiments the anti-cancer agents are chemotherapeutic agents.

In some embodiments the anti-cancer agent is a kinase inhibitor.

In some embodiments the anti-cancer agent is selected from the group consisting of temozolomide, etoposide, doxorubicin, cisplatin, paclitaxel, carmustine, lomustine, ceramide and phosphorylcholine and other suitable anti-cancer agents including kinase inhibitors.

In some embodiments the method further comprises subjecting the patient to radiation therapy.

Apelin Receptor Antagonist Activity

The present inventors have found that the compounds of the invention have the ability to act as apelin receptor antagonists.

A therapeutically effective amount of an apelin receptor antagonist can be administered to humans or mammals other than human. The therapeutically effective amount changes depending on each patient, disease, symptoms, dosage forms and routes of administration. For example in the case of an adult patient (weighing ca. 60 kg) suffering from cancer, the dose may range from 0.05 mg to 10 g per day using as the active ingredient an apelin receptor antagonist or a pharmaceutically active salt thereof according to the present invention. Such quantities can be administered to the patient once or several time each day.

A receptor antagonist (in this case an apelin receptor antagonist) refers to a substance that antagonises or blocks the effects of another ligand at a receptor, rather than activating it like an agonist. A competitive antagonist is a substance that will compete with available agonists for receptor binding sites on the same receptor. Presence of a competitive antagonist will shift an agonist dose-response curve to the right. A Schild plot for a competitive antagonist will have a slope close to 1, and the X-intercept and Y-intercept will each equal the dissociation constant of the antagonist. [Pharmacology in Drug Discovery and Development: Understanding Drug Response, Edition 2, Terry Kenakin, Oct. 21, 2016, Academic Press]

Antagonist activity at the apelin receptor was measured in two assays. The cAMP assay (Example 4A) measures the canonical signalling pathway through the G-protein. pA2 is the negative logarithm to base 10 of the molar concentration of an antagonist that makes it necessary to double the concentration of the agonist needed to elicit the original submaximal response obtained in the absence of antagonist [61].

The β-arrestin assay (Example 4B) measures the alternative signalling pathway and receptor internalisation. pA2 is the negative logarithm to base 10 of the molar concentration of an antagonist that makes it necessary to double the concentration of the agonist needed to elicit the original submaximal response obtained in the absence of antagonist.

Examples of antagonist activity are taken from Table 3.

Example 1

MM193, CRPR-Nle-CKHCR-Aib-R-Nle-(3,4,5-trifluoro-)F, has a binding affinity of Ki=19 nM at the apelin receptor (Cerep) and a pA2=7.68 in the DRx β-Arrestin assay and a pA2=7.37 in the DRx cAMP assay.

Example 2

MM300, Myristoyl-CRPR-Nle-CKHCR-Aib-R-Nle-(3,4,5-trifluoro-)F, has a binding affinity of Ki=13 nM at the apelin receptor (Cerep) and a pA2=8.96 in the DRx β-Arrestin assay, and a pA2=9.66 in the DRx cAMP assay.

Example 3

MM301, Pyr-RPR-Nle-Abu-KH-Abu-R-Aib-R-Nle-(3,4,5-trifluoro-)F, has a binding affinity of Ki=28 nM at the apelin receptor (Cerep) and a pA2=7.28 in the DRx β-Arrestin assay and a pA2=6.29 in the DRx cAMP assay.

The therapeutic effects of apelin receptor antagonists are due to effects on β-Arrestin or cAMP signalling or a combination of both. Compounds may display pA2 values consistent inhibition of β-Arrestin and/or the cAMP signalling with pA2 values from 0-10, preferably with pA2 values from 4-10.

EXAMPLES

Example 1: Synthesis of Compounds

Peptides MM54, MM107, MM108, MM193, MM262. Syntheses were performed by Cambridge Peptides (Cambridge Peptides Limited, 1 Philip Victor Road, Birmingham, West Midlands, B20 2QB, UK) using a PT Symphony and using standard Fmoc chemistry, purified by RP-HPLC on C18 columns. Where applicable, the peptides were cyclised using iodine oxidation, and purified by RP-HPLC. Peptides were analysed by LCMS and mass spectrometry.

Peptides MM297, MM298, MM299, MM300, MM301, MM302, MM312, MM313, MM314, MM315, MM316. MM412, MM413, MM414, MM415, MM416, MM417, MM418, MM419, MM420, MM421, MM422, MM423, MM424, MM426, MM428.

Syntheses were performed by Pepmic Co., Ltd. NO. 35 XingXian Road, High-tech Development Zone, Suzhou, China 215151 using standard fMOC synthesis. Peptides were analysed by LCMS and mass spectrometry.

The final peptide was purified by preparative HPLC using COSMOSIL C18 (30*250 mm, 15 μm, 100 Å), eluted with a linear gradient of CH3CN (11-20% (00520-5,-6), 8-18% (00520-7), 10-20% (00520-8)) in 0.1% TFA/H2O over 30 min at a flow rate of 20 mL/min, and the peptide was detected by UV at 230 nm.

The purity of the collected major peak was verified by analytical HPLC using an injection volume of 20 uL into a Kinetix 100A 4.6×50 mm column, gradient from 2%-80% acetonitrile, in 8 minutes at 60 deg C. with a flow rate of 1.5 ms/min. The peptide sequence and cyclisation was confirmed by electrospray ionization mass spectrometry in positive or negative scan mode.

Characterization of Compounds of the Invention

TABLE 1a

| Compound | Structure |
| --- | --- |
| MM54 | cyclo(1-6)CRPRLC-KH-cyclo(9-14)CRPRLC |
| MM107 | CRPRLCHKCRPRLC |
| MM108 | CRPRLCKHCRPRLC |
| MM193 | CRPR-Nle-CKHCR-Aib-R-Nle-(3,4,5-trifluoro-)F |
| MM262 | QRPR-Nle-CKHCR-Aib-R-Nle-(3,4,5-trifluorophenylalanine) |
| MM297 | pyr-RPR-Nle-CKHCR-Aib-R-Nle-(3,4,5-trifluoro-)F |
| MM298 | CRPR-Nle-Abu-KHCR-Aib-R-Nle-(3,4,5-trifluoro-)F |
| MM299 | CRPR-Nle-CKH-Abu-R-Aib-R-Nle-(3,4,5-trifluoro-)F |
| MM300 | Myristoyl-CRPR-Nle-CKHCR-Aib-R-Nle-(3,4,5-trifluoro-)F |
| MM301 | Pyr-RPR-Nle-Abu-KH-Abu-R-Aib-R-Nle-(3,4,5-trifluoro-)F |
| MM302 | CRPR-Nle-CHKCR-Aib-R-Nle-(3,4,5-trifluoro-)F |
| MM312 | ARPR-Nle-CKH-Abu-R-Aib-R-Nle-(3,4,5-trifluoro-)F |
| MM313 | Ac-ARPR-Nle-CKH-Abu-R-Aib-R-Nle-(3,4,5-trifluoro-)F |
| MM314 | ARPR-Nle-Abu-KH-Abu-R-Aib-R-Nle-(3,4,5-trifluoro-)F |
| MM315 | Mysistoyl-ARPR-Nle-Abu-KH-Abu-R-Aib-R-Nle-(3,4,5-trifluoro-)F |
| MM316 | Mysistoyl-ARPR-Nle-Abu-HK-Abu-R-Aib-R-Nle-(3,4,5-trifluoro-)F |
| MM54 (SEQ ID NO: 2) | cyclo(1-6)CRPRLC-KH-cyclo(9-14)CRPRLC |
| MM107 (SEQ ID NO: 3) | CRPRLCHKCRPRLC |
| MM108 (SEQ ID NO: 4) | CRPRLCKHCRPRLC |
| MM193 (SEQ ID NO: 5) | CRPR-Nle-CKHCR-Aib-R-Nle-(3,4,5-trifluorophenylalanine) |
| MM262 (SEQ ID NO: 6) | QRPR-Nle-CKHCR-Aib-R-Nle-(3,4,5-trifluorophenylalanine) |
| MM297 (SEQ ID NO: 7) | pyr-RPR-Nle-CKHCR-Aib-R-Nle-(3,4,5-trifluorophenylalanine) |
| MM298 (SEQ ID NO: 8) | CRPR-Nle-Abu-KHCR-Aib-R-Nle-(3,4,5-trifluorophenylalanine) |
| MM299 (SEQ ID NO: 9) | CRPR-Nle-CKH-Abu-R-Aib-R-Nle-(3,4,5-trifluorophenylalanine) |
| MM300 (SEQ ID NO: 10) | Myristoyl-CRPR-Nle-CKHCR-Aib-R-Nle-(3,4,5-trifluorophenylalanine) |
| MM301 (SEQ ID NO: 11) | Pyr-RPR-Nle-Abu-KH-Abu-R-Aib-R-Nle-(3,4,5-trifluorophenylalanine) |
| MM302 (SEQ ID NO: 12) | CRPR-Nle-CHKCR-Aib-R-Nle-(3,4,5-trifluorophenylalanine) |

TABLE 1a-continued

| Compound | Structure |
|---|---|
| MM312 (SEQ ID NO: 13) | ARPR-Nle-CKH-Abu-R-Aib-R-Nle-(3,4,5-trifluorophenylalanine) |
| MM313 (SEQ ID NO: 14) | Ac-ARPR-Nle-CKH-Abu-R-Aib-R-Nle-(3,4,5-trifluorophenylalanine) |
| MM314 (SEQ ID NO: 15) | ARPR-Nle-Abu-KH-Abu-R-Aib-R-Nle-(3,4,5-trifluorophenylalanine) |
| MM315 (SEQ ID NO: 16) | Myristoyl-ARPR-Nle-Abu-KH-Abu-R-Aib-R-Nle-(3,4,5-trifluorophenylalanine) |
| MM316 (SEQ ID NO: 17) | Myristoyl-ARPR-Nle-Abu-HK-Abu-R-Aib-R-Nle-(3,4,5-trifluorophenylalanine) |
| MM412 (SEQ ID NO: 18) | Ac-ARPR-Nle-Abu-K(GluPAL)-H-Abu-R-Aib-R-Nle-(3,4,5-trifluoroalanine) |
| MM413 (SEQ ID NO: 19) | ARPR-Nle-Abu-KH-Abu-R-Aib-R-Nle |
| MM414 (SEQ ID NO: 20) | ARPR-Nle-Abu-KH-Abu-R-Aib-R-Nle-Alanine |
| MM415 (SEQ ID NO: 21) | ARPR-Nle-Abu-KH-Abu-R-Aib-R-Nle-Phenylglycine |
| MM416 (SEQ ID NO: 22) | ARPR-Nle-Abu-KH-Abu-R-Aib-R-Nle-Phenylalanine |
| MM417 (SEQ ID NO: 23) | ARPR-Nle-Abu-KH-Abu-R-Aib-R-Nle-(4-methoxyphenylalanine) |
| MM418 (SEQ ID NO: 24) | ARPR-Nle-Abu-KH-Abu-R-Aib-R-Nle-(4-chlorophenylalanine) |
| MM419 (SEQ ID NO: 25) | ARPR-Nle-Abu-KH-Abu-R-Aib-R-Nle-(4-benzoylphenylalanine) |
| MM420 (SEQ ID NO: 26) | ARPR-Nle-Abu-KH-Abu-R-Aib-R-Nle-(O-Benzyltyrosine) |
| MM421 (SEQ ID NO: 27) | ARPR-Nle-Abu-KH-Abu-R-Aib-R-Nle-(3-(1-naphthyl)alanine) |
| MM422 (SEQ ID NO: 28) | ARPR-Nle-Abu-KH-Abu-R-Aib-R-Nle-(3-(2-naphthyl)alanine) |
| MM423 (SEQ ID NO: 29) | ARPR-Nle-Abu-KH-Abu-R-Aib-R-Nle-(2-Aminoindane) |
| MM424 (SEQ ID NO: 30) | ARPR-Nle-Abu-KH-Abu-R-Aib-R-Nle-(4-Aminopiperidine-4-carboxylic acid) |
| MM426 (SEQ ID NO: 31) | Ac-ARPR-Nle-Abu-K(PAL)-H-Abu-R-Aib-R-Nle-(3,4,5-trifluorophenylalanine) |
| MM428 (SEQ ID NO: 32) | ARPR-Nle-Abu-KH-Abu-R-Aib-R-Nle-(Alpha-Methyl-L-phenylalanine) |

TABLE 1b

| Compound | Purity % | Mw Found M + 1 | M + 2 | M + 3 | M + 4 | M + 5 | Theoretical mass (Mw) | Mw expected M + 1 | M + 2 | M + 3 | M + 4 | M + 5 |
|---|---|---|---|---|---|---|---|---|---|---|---|---|
| MM54 | 95.01 | 1737.19 | 869.25 | 580 | 435.3 | | 1735.85 | 1736.86 | 868.93 | 579.62 | 434.97 | 348.18 |
| MM107 | 98.99 | 1741.09 | 871.12 | 581.32 | 436.22 | 348.97 | 1739.88 | 1740.89 | 870.95 | 580.97 | 435.98 | 348.98 |
| MM108 | 95.35 | 1741.19 | 870.98 | 581.21 | 436.18 | 349.13 | 1739.88 | 1740.89 | 870.95 | 580.97 | 435.98 | 348.98 |
| MM193 | 97.69 | 1827.69 | 914.8 | 610 | 458 | 366.5 | 1825.91 | 1826.92 | 913.96 | 609.64 | 457.49 | 366.19 |
| MM262 | 95.95 | 1852 | 926.9 | 618.3 | 464 | 371.4 | 1851.7 | 1852.71 | 926.86 | 618.24 | 463.93 | 371.35 |
| MM297 | 96 | 1835.6 | 918.45 | 612.75 | 459.9 | 368.15 | 1834.66 | 1835.67 | 918.34 | 612.56 | 459.67 | 367.94 |
| MM298 | 95.06 | 1810.61 | 905.5 | 604.05 | 453.4 | 362.95 | 1808.82 | 1809.83 | 905.42 | 603.95 | 453.21 | 362.77 |
| MM299 | 96.08 | 1810.60 | 905.5 | 604.05 | 453.4 | 362.9 | 1808.82 | 1809.83 | 905.42 | 603.95 | 453.21 | 362.77 |
| MM300 | 97.59 | 2038.01 | | 679.95 | 510.2 | 408.45 | 2037.07 | 2038.08 | 1019.54 | 680.03 | 510.28 | 408.42 |
| MM301 | 97.13 | 1800.61 | 900.5 | 600.7 | 450.9 | 360.9 | 1798.89 | 1799.9 | 900.45 | 600.64 | 450.73 | 360.79 |
| MM302 | 95.07 | 1828.21 | | 610.05 | 457.8 | 366.5 | 1826.7 | 1827.71 | 914.36 | 609.91 | 457.68 | 366.35 |
| MM312 | 95.46 | 1777 | 889.35 | 593.2 | 445.25 | 356.95 | 1775.85 | 1776.86 | 888.93 | 592.96 | 444.97 | 356.18 |
| MM313 | 95.08 | 1819 | | 607.25 | 455.7 | 364.8 | 1817.89 | 1818.9 | 909.95 | 606.97 | 455.48 | 364.59 |
| MM314 | 97.38 | 1758.5 | | 587.15 | 440.55 | 352.7 | 1757.77 | 1758.78 | 879.89 | 586.93 | 440.45 | 352.56 |
| MM315 | 95.19 | 1969.25 | | 657.25 | 493.3 | 394.85 | 1968.14 | 1969.15 | 985.08 | 657.06 | 493.04 | 394.64 |
| MM316 | 95.12 | 1969.25 | | 657.35 | 493.2 | 394.85 | 1968.24 | 1969.25 | 985.13 | 657.09 | 493.07 | 394.66 |

| Compound | Purity % | Mw Found M + 1 | M + 2 | M + 3 | M + 4 | M + 5 | Theoretical mass | Mw expected M + 1 | M + 2 | M + 3 | M + 4 | M + 5 |
|---|---|---|---|---|---|---|---|---|---|---|---|---|
| MM54 | 97.15 | 1737.50 | 869.25 | 580.00 | 435.30 | | 1735.84 | 1736.85 | 868.93 | 579.62 | 434.97 | 348.18 |
| MM107 | 98.99 | 1741.09 | 871.12 | 581.32 | 436.22 | 348.97 | 1739.88 | 1740.89 | 870.95 | 580.97 | 435.98 | 348.98 |
| MM108 | 95.35 | 1741.19 | 870.98 | 581.21 | 436.18 | 349.13 | 1739.88 | 1740.89 | 870.95 | 580.97 | 435.98 | 348.98 |
| MM193 | 97.69 | 1827.69 | 914.80 | 610.00 | 458.00 | 366.50 | 1827.20 | 1828.21 | 914.61 | 610.08 | 457.81 | 366.45 |
| MM262 | 95.95 | 1852.00 | 926.90 | 618.30 | 464.00 | 371.40 | 1851.70 | 1852.71 | 926.86 | 618.24 | 463.93 | 371.35 |
| MM297 | 96.00 | 1835.60 | 918.45 | 612.75 | 459.90 | 368.15 | 1834.66 | 1835.67 | 918.34 | 612.56 | 459.67 | 367.94 |
| MM298 | 95.06 | 1809.60 | 905.50 | 604.05 | 453.40 | 362.95 | 1808.82 | 1809.83 | 905.42 | 603.95 | 453.21 | 362.77 |
| MM299 | 96.08 | 1809.60 | 905.50 | 604.05 | 453.40 | 362.90 | 1808.82 | 1809.83 | 905.42 | 603.95 | 453.21 | 362.77 |
| MM300 | 97.59 | 2037.25 | 1019.40 | 679.95 | 510.20 | 408.45 | 2037.07 | 2038.08 | 1019.54 | 680.03 | 510.28 | 408.42 |
| MM301 | 97.13 | 1799.60 | 900.50 | 600.70 | 450.90 | 360.90 | 1798.89 | 1799.90 | 900.45 | 600.64 | 450.73 | 360.79 |
| MM302 | 95.07 | 1827.20 | 915.55 | 610.05 | 457.80 | 366.50 | 1826.70 | 1827.71 | 914.36 | 609.91 | 457.68 | 366.35 |
| MM312 | 95.46 | 1777.00 | 889.35 | 593.20 | 445.25 | 356.95 | 1775.85 | 1776.86 | 888.93 | 592.96 | 444.97 | 356.18 |
| MM313 | 95.08 | 1819.00 | 910.20 | 607.25 | 455.70 | 364.80 | 1817.89 | 1818.90 | 909.95 | 606.97 | 455.48 | 364.59 |
| MM314 | 97.38 | 1758.50 | 880.15 | 587.15 | 440.55 | 352.70 | 1757.77 | 1758.78 | 879.89 | 586.93 | 440.45 | 352.56 |
| MM315 | 96.47 | 1969.40 | 985.60 | 657.60 | 493.35 | 394.85 | 1968.16 | 1969.17 | 985.09 | 657.06 | 493.05 | 394.64 |
| MM316 | 95.12 | 1969.25 | | 657.35 | 493.20 | 394.85 | 1968.24 | 1969.25 | 985.13 | 657.09 | 493.07 | 394.66 |
| MM412 | 95.76 | 2168.40 | 1085.20 | 723.90 | 543.25 | 434.75 | 2167.34 | 2168.35 | 1084.68 | 723.46 | 542.84 | 434.48 |
| MM413 | 98.42 | 1557.60 | 779.80 | 520.20 | 390.30 | 312.30 | 1556.95 | 1557.96 | 779.48 | 519.99 | 390.25 | 312.40 |
| MM414 | 97.78 | 1628.85 | 815.35 | 543.95 | 408.15 | | 1628.04 | 1629.05 | 815.03 | 543.69 | 408.02 | 326.62 |
| MM415 | 99.09 | 1690.40 | 846.30 | 564.55 | 423.60 | 338.95 | 1690.11 | 1691.12 | 846.06 | 564.38 | 423.54 | 339.03 |
| MM416 | 97.88 | 1704.70 | 853.35 | | | | 1704.14 | 1705.15 | 853.08 | 569.06 | 427.04 | 341.84 |
| MM417 | 98.56 | 1734.60 | 868.40 | 579.25 | 434.65 | 347.75 | 1734.10 | 1735.11 | 868.06 | 579.04 | 434.53 | 347.83 |
| MM418 | 98.74 | 1739.00 | 870.50 | | | | 1738.52 | 1739.53 | 870.27 | 580.52 | 435.64 | 348.71 |
| MM419 | 98.53 | 1808.90 | 905.45 | | | | 1808.18 | 1809.19 | 905.10 | 603.74 | 453.05 | 362.64 |
| MM420 | 98.33 | 1810.80 | 906.40 | 604.65 | 453.70 | 363.00 | 1810.20 | 1811.21 | 906.11 | 604.41 | 453.56 | 363.05 |
| MM421 | 98.83 | 1754.85 | 878.40 | 585.95 | 439.65 | 351.75 | 1754.14 | 1755.15 | 878.08 | 585.72 | 439.54 | 351.84 |
| MM422 | 97.74 | 1754.80 | 878.40 | 585.80 | | | 1754.14 | 1755.15 | 878.08 | 585.72 | 439.54 | 351.84 |

TABLE 1b-continued

| MM423 | 97.67 | 1717.05 | 859.40 | 573.35 | 430.20 | 344.20 | 1716.09 | 1717.10 | 859.05 | 573.04 | 430.03 | 344.23 |
| MM424 | 98.75 | 1783.20 | 892.50 | 595.55 | 446.80 | | 1783.18 | 1784.19 | 892.60 | 595.40 | 446.80 | 357.64 |
| MM426 | 96.91 | 2039.55 | 1020.70 | 680.85 | 510.80 | 408.70 | 2038.46 | 2039.47 | 1020.24 | 680.50 | 510.62 | 408.70 |
| MM428 | 95.03 | 1718.85 | 860.40 | 573.96 | 430.65 | 344.60 | 1718.10 | 1719.11 | 860.06 | 573.71 | 430.53 | 344.63 |

Example 2: Binding and Functional Assays

Binding assays were performed by Cerep (Celle L'Evescault, France) on Chinese Hamster Ovary (CHO-K1) cells expressing the human apelin receptor. Initial experiments were performed to determine whether a single concentration of test peptide (1 or 10 µmol/L) inhibited specific binding of [Glp$^{65}$, Nle$^{75}$, Tyr$^{77}$][$^{125}$I]apelin-13 (0.03 nmol/L). The results were expressed as a percent of control specific binding ((measured specific binding/control specific binding)×100) and as a percent inhibition of control specific binding (100−((measured specific binding/control specific binding)×100)) obtained in the presence of the test compounds. Results showing an inhibition higher than 50% was considered to represent significant effects of the test compounds. Results showing an inhibition between 20% and 50% were indicative of weak to moderate effects. Results showing an inhibition lower than 20% were not considered significant and mostly attributable to variability of the signal around the control level. For those compounds showing greater than 50% inhibition of specific binding, competition curves were generated and analysed using non-linear regression analysis of mean replicate values to obtain values of IC$_{50}$ (concentration causing half-maximal inhibition of control specific binding) and Hill coefficients (nH) using Hill equation curve fitting $(Y=D+[(A-D)/(1+(C/C_{50})^{nH})])$, where Y=specific binding, D=minimum specific binding, A=maximum specific binding, C=compound concentration, C$_{50}$=IC$_{50}$, and nH=slope factor). The inhibition constants (K$_i$) were calculated using the Cheng Prusoff equation (K$_i$=IC$_{50}$/(1+(L/K$_D$)), where L=concentration of radioligand in the assay, and K$_D$=equilibrium dissociation constant of the radioligand for the receptor). In each experiment, the respective reference compound, [Pyr$^1$]apelin-13, was tested concurrently with the test compounds.

Example 3: Determination of Affinity (pK$_i$) for the Human Apelin Receptor

For competition binding experiments homogenate of human left ventricle was incubated for 90 min with 0.1 nmol/L [Glp$^{65}$, Nle$^{75}$, Tyr$^{77}$][$^{125}$I]apelin-13 in assay buffer (mmol/L: Tris 50, MgCl$_2$ 5, pH 7.4, 22° C.), in the presence of increasing concentrations of test peptides (0.5 pmol/L-10 µmol/L). Non-specific binding was defined using 1 µmol/L [Pyr$^1$]apelin-13. Equilibrium was broken by centrifugation (20,000 g for 10 min, 4° C.). Pellets were washed with Tris-HCl buffer (50 mmol/L, pH 7.4, 4° C.), re-centrifuged and bound radioactivity in the final pellets counted. Data from triplicate experiments were analysed using the iterative non-linear curve fitting programs EBDA and LIGAND (KELL package, Biosoft, UK) or GraphPad Prism 6 to derive values of affinity (expressed as either the equilibrium dissociation constant K$_D$ or the negative log$_{10}$ of the dissociation constant, pK$_i$±sem) and receptor density (B$_{MAX}$±sem in fmoles bound per mg protein).

Example 4: cAMP and β-Arrestin Assays cAMP (cAMP Hunter™ eXpress AGTRL1 CHO-K1 GPCR Assay, DiscoverX Corporation, Ltd. Birmingham, UK) and β-arrestin (PathHunter® eXpress AGTRL1 CHO-K1 β-Arrestin GPCR Assay, DiscoverX Corporation, Ltd. Birmingham, UK) assays were performed according to the manufacturer's instructions. The cAMP assay measures the canonical signalling pathway through the G-protein. The β-arrestin assay measures the alternative signalling pathway and receptor internalisation.

Example 4A: cAMP Assay

For inhibition of forskolin-induced cAMP accumulation, CHO-K1 cells artificially expressing the human apelin receptor were seeded in Cell Plating medium into 96-well plates and incubated for 24 hours at 37° C. in 5% CO$_2$, followed by replacement of the medium with cAMP Antibody Reagent in Cell Assay Buffer. Basal levels of cAMP were elevated by 30 minutes incubation of cells with 15 µmol/L forskolin, at 37° C., in the absence or presence test peptides (1 pmol/L-0.3 µmol/L) diluted in Cell Assay Buffer. Cells were then incubated with a mixture of Lysis Buffer, cAMP Buffer D and Detection Reagents for 1 hour at room temperature, followed by a 3 hour incubation with cAMP Reagent A at room temperature. Chemiluminescence was read using the LumiLITE™ Microplate Reader (DiscoverX). Concentration-response data for agonists, measured in relative light units (RLU), were analysed using a 4 parameter logistic equation in GraphPad Prism 6 (La Jolla, CA, USA) to determine values of potency expressed as the pD2 value (negative logo of the EC$_{50}$ (where EC$_{50}$ is the concentration producing half maximal response)), and maximum response (E$_{MAX}$). Mean data from replicate experiments were normalised as percentage inhibition of forskolin-stimulated cAMP production. Peptides that did not produce an agonist response but were shown to have receptor affinity in the human heart binding assay were subsequently tested as receptor antagonists. For these experiments concentration response curves were constructed to [Pyr$^1$]apelin-13 in the absence (control) and presence of a single concentration of test peptide (1-30 µM). Data were analysed using the Gaddum/Schild EC$_{50}$ function in GraphPad Prism 6 to determine antagonist affinities expressed as pA$_2$ (the negative logarithm of the concentration of antagonist needed to shift the concentration response curve to [Pyr$^1$]apelin-13 by a factor of 2). The Schild slope, if not different from 1, was constrained to 1 so that pA$_2$ is equal to the negative log of the antagonist dissociation constant K$_B$.

Example 4B: β-Arrestin Assay

For recruitment of β-arrestin, CHO-K1 cells artificially expressing the human apelin receptor were seeded in Cell Plating medium into 96-well plates and incubated for 48 hours at 37° C. in 5% CO$_2$. Concentration response curves were constructed to test peptides (1 pmol/L-30 µmol/L) which were diluted in Cell Plating medium and added to the cells for 90 minutes at 37° C. If no response was obtained then test peptides were investigated as antagonists. For antagonist experiments, an additional 30-minute incubation was carried in the absence or presence of a single concentration (1-30 μmol/L) of test peptide prior to addition of the [Pyr¹]apelin-13 concentration response curve. Detection reagents were then added for a 2-hour incubation at room temperature. Agonist responses, measured in RLUs, were fitted to 4 parameter logistic equation in GraphPad Prism 6 (La Jolla, CA, USA) to determine values of potency $pD_2$ and $E_{MAX}$ as described for the cAMP assay. Data were subsequently normalized to the maximum response to [Pyr¹] apelin-13 that was used as the reference agonist in each experiment. If no agonist response was obtained, test compounds were investigated for antagonist activity by repeating [Pyr]apelin-13 concentration response curves in the absence and presence of a single concentration (1-30 μmol/L of test peptide). Data were analysed as described for the cAMP assay using the Gaddum/Schild $EC_{50}$ function in GraphPad Prism 6 to determine values of $pA_2$.

TABLE 2

Compounds of the invention

| Comp. No. | ($R^1$-$L_c$) | $X^1$ | $X^2$ | $X^3$ | $X^4$ | $X^5$ | $X^6$ | $X^7$ | $X^8$ | $X^9$ | $X^{10}$ | $X^{11}$ | $X^{12}$ | $X^{13}$ | $X^{14}$ | ($R^2$-$L_c$) |
|---|---|---|---|---|---|---|---|---|---|---|---|---|---|---|---|---|
| MM107 | — | C | R | P | R | L | C | H | K | C | R | P | R | L | C | — |
| MM108 | — | C | R | P | R | L | C | K | H | C | R | P | R | L | C | — |
| MM193 | — | C | R | P | R | Nle | C | K | H | C | R | Aib | R | Nle | (3,4,5-trifluoro-)F | — |
| MM262 | — | Q | R | P | R | Nle | C | K | H | C | R | Aib | R | Nle | (3,4,5-trifluoro-)F | — |
| MM297 | — | Glp | R | P | R | Nle | C | K | H | C | R | Aib | R | Nle | (3,4,5-trifluoro-)F | — |
| MM298 | — | C | R | P | R | Nle | Abu | K | H | C | R | Aib | R | Nle | (3,4,5-trifluoro-)F | — |
| MM299 | — | C | R | P | R | Nle | C | K | H | Abu | R | Aib | R | Nle | (3,4,5-trifluoro-)F | — |
| MM300 | Myristoyl (N-terminal) | C | R | P | R | Nle | C | K | H | C | R | Aib | R | Nle | (3,4,5-trifluoro-)F | — |
| MM301 | — | Glp | R | P | R | Nle | Abu | K | H | Abu | R | Aib | R | Nle | (3,4,5-trifluoro-)F | — |
| MM302 | — | C | R | P | R | Nle | C | H | K | C | R | Aib | R | Nle | (3,4,5-trifluoro-)F | — |
| MM312 | — | A | R | P | R | Nle | C | K | H | Abu | R | Aib | R | Nle | (3,4,5-trifluoro-)F | — |
| MM313 | Ac | A | R | P | R | Nle | C | K | H | Abu | R | Aib | R | Nle | (3,4,5-trifluoro-)F | — |
| MM314 | — | A | R | P | R | Nle | Abu | K | H | Abu | R | Aib | R | Nle | (3,4,5-trifluoro-)F | — |
| MM315 | Myristoyl | A | R | P | R | Nle | Abu | K | H | Abu | R | Aib | R | Nle | (3,4,5-trifluoro-)F | — |
| MM316 | Myristoyl | A | R | P | R | Nle | Abu | H | K | Abu | R | Aib | R | Nle | (3,4,5-trifluoro-)F | — |
| MM107 | — | C | R | P | R | L | C | H | K | C | R | P | R | L | C | — |
| MM108 | — | C | R | P | R | L | C | K | H | C | R | P | R | L | C | — |
| MM193 | — | C | R | P | R | Nle | C | K | H | C | R | Aib | R | Nle | (3,4,5-trifluoro-)F | — |
| MM262 | — | Q | R | P | R | Nle | C | K | H | C | R | Aib | R | Nle | (3,4,5-trifluoro-)F | — |
| MM297 | — | Glp | R | P | R | Nle | C | K | H | C | R | Aib | R | Nle | (3,4,5-trifluoro-)F | — |
| MM298 | — | C | R | P | R | Nle | Abu | K | H | C | R | Aib | R | Nle | (3,4,5-trifluoro-)F | — |
| MM299 | — | C | R | P | R | Nle | C | K | H | Abu | R | Aib | R | Nle | (3,4,5-trifluoro-)F | — |
| MM300 | Myristoyl | C | R | P | R | Nle | C | K | H | C | R | Aib | R | Nle | (3,4,5-trifluoro-)F | — |
| MM301 | — | Glp | R | P | R | Nle | Abu | K | H | Abu | R | Aib | R | Nle | (3,4,5-trifluoro-)F | — |
| MM302 | — | C | R | P | R | Nle | C | H | K | C | R | Aib | R | Nle | (3,4,5-trifluoro-)F | — |
| MM312 | — | A | R | P | R | Nle | C | K | H | Abu | R | Aib | R | Nle | (3,4,5-trifluoro-)F | — |
| MM313 | Ac | A | R | P | R | Nle | C | K | H | Abu | R | Aib | R | Nle | (3,4,5-trifluoro-)F | — |
| MM314 | — | A | R | P | R | Nle | Abu | K | H | Abu | R | Aib | R | Nle | (3,4,5-trifluoro-)F | — |
| MM315 | Myristoyl | A | R | P | R | Nle | Abu | K | H | Abu | R | Aib | R | Nle | (3,4,5-trifluoro-)F | — |
| MM316 | Myristoyl | A | R | P | R | Nle | Abu | H | K | Abu | R | Aib | R | Nle | (3,4,5-trifluoro-)F | — |
| MM412 | Ac | A | R | P | R | Nle | Abu | K(GluPAL) | H | Abu | R | Aib | R | Nle | (3,4,5-trifluoro-)F | |
| MM413 | | A | R | P | R | Nle | Abu | K | H | Abu | R | Aib | R | Nle | — | — |
| MM413 | | A | R | P | R | Nle | Abu | K | H | Abu | R | Aib | R | Nle | | |
| MM414 | | A | R | P | R | Nle | Abu | K | H | Abu | R | Aib | R | Nle | Alanine | |
| MM415 | | A | R | P | R | Nle | Abu | K | H | Abu | R | Aib | R | Nle | Phenylglycine | |
| MM416 | | A | R | P | R | Nle | Abu | K | H | Abu | R | Aib | R | Nle | Phenylalanine | |
| MM417 | | A | R | P | R | Nle | Abu | K | H | Abu | R | Aib | R | Nle | 4-methoxyphenly-alanine | |
| MM418 | | A | R | P | R | Nle | Abu | K | H | Abu | R | Aib | R | Nle | 4-chlorophenyl-alanine | |
| MM419 | | A | R | P | R | Nle | Abu | K | H | Abu | R | Aib | R | Nle | 4-benzoylphenyl-alanine | |
| MM420 | | A | R | P | R | Nle | Abu | K | H | Abu | R | Aib | R | Nle | O-Benzyltyrosine | |
| MM421 | | A | R | P | R | Nle | Abu | K | H | Abu | R | Aib | R | Nle | 3-(1-naphthyl)alanine | |
| MM422 | | A | R | P | R | Nle | Abu | K | H | Abu | R | Aib | R | Nle | 3-(2-naphthyl)alanine | |
| MM423 | | A | R | P | R | Nle | Abu | K | H | Abu | R | Aib | R | Nle | 2-Aminoindane | |
| MM424 | | A | R | P | R | Nle | Abu | K | H | Abu | R | Aib | R | Nle | 4-Aminopiperidine-4-carboxylic acid | |
| MM426 | Ac | A | R | P | R | Nle | Abu | K(PAL) | H | Abu | R | Aib | R | Nle | (3,4,5-trifluoro-)F | |
| MM428 | | A | R | P | R | Nle | Abu | K | H | Abu | R | Aib | R | Nle | Alpha-Methyl-L-phenylalanine | |

TABLE 3

Results of cAMP and β-arrestin assays

| Compound ref | $K_i$ (nM) | HLV $pK_i$ | DRx β-Arrestin | DRx cAMP |
|---|---|---|---|---|
| [Pyr¹]apelin-13 pERPRLSHKGPMPF (SEQ ID NO: 1) | 1.2 | 8.83 | $pD_2$ = 8.53 | $pD_2$ = 9.52 |
| MM54 cyclo(1-6)CRPRLC-KH-cyclo(9-14)CRPRLC (SEQ ID NO: 2) | 82 | 6.45 | $pA_2$ = 6.63 | $pD_2$ = 5.86 |
| MM107 CRPRLCHKCRPRLC (SEQ ID NO: 3) | 180 | | $pA_2$ = 7.24 | $pA_2$ = 5.33 |
| MM108 CRPRLCKHCRPRLC (SEQ ID NO: 4) | 140 | | $pA_2$ = 7.41 | $pA_2$ 6.97 |
| MM193 CRPR-Nle*-CKHCR-Aib*-R-Nle*-(3,4,5-trifuoro-)F (SEQ ID NO: 5) | 19 | 6.12 | $pA_2$ = 7.68 | $pA_2$ = 7.37 |
| MM262 QRPR-Nle-CKHCR-Aib-R-Nle-(3,4,5-trifluoro-)F (SEQ ID NO: 6) | 34 | | $pA_2$ = 7.53 | $pA_2$ = 6.35 |
| MM297 pyr-RPR-Nle-CKHCR-Aib*-R-Nle*-(3,4,5-trifluoro-)F (SEQ ID NO: 7) | 55 | | $pA_2$ = 7.38 | $pA_2$ = 6.08 |
| MM298 CRPR-Nle-Abu-KHCR-Aib*-R-Nle-(3,4,5-trifluoro-)F (SEQ ID NO: 8) | 16 | | $pA_2$ = 7.76 | $pA_2$ = 7.59 |
| MM299 CRPR-Nle-CKH-Abu-R-Aib*-R-Nle*-(3,4,5-trifluoro-)F (SEQ ID NO: 9) | 6.1 | | $pA_2$ = 8.10 | $pA_2$ = 7.32 |
| MM300 Myristoyl-CRPR-Nle-CKHCR-Aib*-R-Nle-(3,4,5-trifluoro-)F (SEQ ID NO: 10) | 13 | | $pA_2$ = 8.96 | $pA_2$ = 9.66 |
| MM301 Pyr-RPR-Nle-Abu-KH-Abu-R-Aib*-R-Nle-(3,4,5-trifluoro-)F (SEQ ID NO: 11) | 28 | | $pA_2$ = 7.28 | $pA_2$ = 6.29 |
| MM302 CRPR-Nle*-CHKCR-Aib*-R-Nle*-(3,4,5-trifluoro-)F (SEQ ID NO: 12) | 17 | | $pA_2$ = 8.57 | $pA_2$ = 7.70 |
| MM312 ARPR-Nle-CKH-Abu-R-Aib-R-Nle-(3,4,5-trifluoro-)F (SEQ ID NO: 13) | 190 | | $pA_2$ = 5.87 | $pA_2$ = 6.60 |
| MM313 Ac-ARPR-Nle-CKH-Abu-R-Aib-R-Nle-(3,4,5-trifluoro-)F (SEQ ID NO: 14) | 53 | | $pA_2$ = 5.97 | $pA_2$ = 6.66 |
| MM314 ARPR-Nle-Abu-KH-Abu-R-Aib-R-Nle-(3,4,5-trifluoro-)F (SEQ ID NO: 15) | 10 | | $pA_2$ = 5.90 | $pA_2$ = 6.43 |
| MM315 Myristoyl-ARPR-Nle-Abu-KH-Abu-R-Aib-R-Nle-(3,4,5-trifluoro-)F (SEQ ID NO: 16) | 3 | | $pA_2$ = 6.99 | $pA_2$ = 8.52 |
| MM316 Myristoyl-ARPR-Nle-Abu-HK-Abu-R-Aib-R-Nle-(3,4,5-trifluoro-)F (SEQ ID NO: 17) | 3 | | $pA_2$ = 5.95 | $pA_2$ = 7.41 |
| [Pyr¹]apelin-13 pERPRLSHKGPMPF (SEQ ID NO: 1) | 1.2 | 8.83 | $pD_2$ = 8.51 | $pD_2$ = 9.43 |
| MM54 cyclo(1-6)CRPRLC-KH-cyclo(9-14)CRPRLC (SEQ ID NO: 2) | 82 | 6.56 | $pA_2$ = 6.93 | $pD_2$ = 5.86 |
| MM107 CRPRLCHKCRPRLC (SEQ ID NO: 3) | 180 | | $pA_2$ = 7.24 | $pA_2$ = 6.24 |
| MM108 CRPRLCKHCRPRLC (SEQ ID NO: 4) | 140 | | $pA_2$ = 7.41 | $pA_2$ 6.72 |
| MM193 CRPR-Nle*-CKHCR-Aib*-R-Nle*-(3,4,5-trifluoro-)F (SEQ ID NO: 5) | 19 | 6.12 | $pA_2$ = 7.68 | $pA_2$ = 7.11 |
| MM262 QRPR-Nle-CKHCR-Aib-R-Nle-(3,4,5-trifluoro-)F (SEQ ID NO: 6) | 34 | | $pA_2$ = 7.53 | $pA_2$ = 6.87 |
| MM297 pyr-RPR-Nle-CKHCR-Aib*-R-Nle*-(3,4,5-trifluoro-)F (SEQ ID NO: 7) | 55 | | $pA_2$ = 7.38 | $pA_2$ = 6.14 |
| MM298 CRPR-Nle-Abu-KHCR-Aib*-R-Nle-(3,4,5-trifluoro-)F (SEQ ID NO: 8) | 16 | | $pA_2$ = 7.76 | $pA_2$ = 7.12 |
| MM299 CRPR-Nle-CKH-Abu-R-Aib*-R-Nle*-(3,4,5-trifluoro-)F (SEQ ID NO: 9) | 6.1 | | $pA_2$ = 8.53 | $pA_2$ = 6.95 |
| MM300 Myristoyl-CRPR-Nle-CKHCR-Aib*-R-Nle-(3,4,5-trifluoro-)F (SEQ ID NO: 10) | 13 | | $pA_2$ = 8.50 | $pA_2$ = 6.77 |
| MM301 Pyr-RPR-Nle-Abu-KH-Abu-R-Aib*-R-Nle-(3,4,5-trifluoro-)F (SEQ ID NO: 11) | 28 | | $pA_2$ = 7.28 | $pA_2$ = 6.34 |
| MM302 CRPR-Nle*-CHKCR-Aib*-R-Nle*-(3,4,5-trifluoro-)F (SEQ ID NO: 12) | 17 | | $pA_2$ = 8.64 | $pA_2$ = 7.26 |
| MM312 ARPR-Nle-CKH-Abu-R-Aib-R-Nle-(3,4,5-trifluoro-)F (SEQ ID NO: 13) | 160 | | $pA_2$ = 7.52 | $pA_2$ = 6.84 |
| MM313 Ac-ARPR-Nle-CKH-Abu-R-Aib-R-Nle-(3,4,5-trifluoro-)F (SEQ ID NO: 14) | 47 | | $pA_2$ = 7.55 | $pA_2$ = 6.92 |
| MM314 ARPR-Nle-Abu-KH-Abu-R-Aib-R-Nle-(3,4,5-trifluoro-)F (SEQ ID NO: 15) | 8.9 | | $pA_2$ = 7.46 | $pA_2$ = 6.71 |
| MM315 Myristoyl-ARPR-Nle-Abu-KH-Abu-R-Aib-R-Nle-(3,4,5-trifluoro-)F (SEQ ID NO: 16) | 2.7 | | $pA_2$ = 9.64 | $pA_2$ = 8.11 |
| MM316 Myristoyl-ARPR-Nle-Abu-HK-Abu-R-Aib-R-Nle-(3,4,5-trifluoro-)F (SEQ ID NO: 17) | 2.8 | | $pA_2$ = 8.82 | $pA_2$ = 7.88 |

As evidenced by the data in Table 3 there exists a class of linear apelin receptor antagonists which display a range of pharmacological properties including apelin receptor affinity, C-AMP inhibition and β-arrestin inhibition.

The disclosed compound affinities (Cerep Ki) range from 80 nM to 3 nM which indicates high binding affinity to the apelin receptor. High binding affinity often confers high receptor selectivity at the required concentration for receptor inhibition. High binding affinity generally translates to a lower effective therapeutic dose. Compounds disclosed have higher binding affinity than the previously published antagonist MM54 [Brain, Volume 140, Issue 11, 1 Nov. 2017, Pages 2939-2954] and show antagonism at both cAMP and β-Arrestin.

The disclosed activity at the human left ventricle assay (HLV $pK_i$) shows that the compounds can bind to a human apelin receptor in excised human tissue.

The disclosed activity in the β-Arrestin assay (DRx β-Arrestin, pA2 range 5.87-8.96) is indicative of the ability of the antagonist compounds to inhibit the ability of apelin-13 to activate this pathway, which is generally accepted to be followed by receptor internalisation, signalling and de-activation (desensitisation) of the receptor. Greater antagonist activity corresponds to less β-arrestin activation by apelin-13.

The disclosed activity in the c-AMP assay (DRx cAMP, pA2 range 5.86-9.7) is indicative of inhibition of a cascade of receptor signalling modulated by the release of c-AMP. Greater antagonist activity corresponds to less c-AMP activity by apelin-13.

In this class of compounds there is evidence for bias towards either C-AMP (MM300) or towards β-arrestin (MM302) inhibition. This is an unexpected and novel finding. For example, MM193 is similar in inhibition between β-arrestin and cAMP pathways while MM302 shows almost a log unit of bias towards inhibition of the β-arrestin pathway.

Bias towards cAMP pathway inhibition or β-Arrestin pathway inhibition at the Apelin receptor is novel and identifies selective apelin receptor inhibitors that could confer more specific therapeutic effects.

Embodiments of the invention are set out in the following numbered clauses

1. A compound comprising the sequence of Formula I:

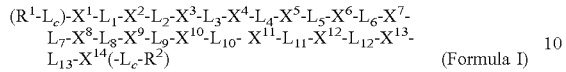

(Formula I)

wherein
$X^1$ is any amino acid;
$X^2$ is selected from the group consisting of R, H, and K;
$X^3$ is p;
$X^4$ is R;
$X^5$ is selected from the group consisting of Nle, L, A, V, I, M, F, Y, and W;
$X^6$ is selected from the group consisting of Abu, C, A, V, I, L, M, F, Y, W, and P;
$X^7$ is selected from the group consisting of H, K, A, V, I, L, M, F, Y, W, and R;
$X^8$ is selected from the group consisting of K, H, A, V, I, L, M, F, Y, W, and R;
$X^9$ is selected from the group consisting of Abu, C, A, V, I, L, M, F, Y, W, and P;
$X^{10}$ is selected from the group consisting of R, H, and K;
$X^{11}$ is selected from the group consisting of Aib, and P;
$X^{12}$ is selected from the group consisting of R, H, and K;
$X^{13}$ is selected from the group consisting of Nle, Aib, L, V, I, and A;
$X^{14}$ is selected from the group consisting of C, F, other hydrophobic amino acids (including Alanine (A), Isoleucine (I), Leucine (L), Methionine (M), Tyrosine (Y), Tryptophan (W), Valine (V), Proline (P), Glycine (G)), and $X^{14}$ may specifically be one of 3,4,5-trifluorophenylalanine (Tfpa or (3,4,5-trifluoro)F), β-cyclohexylalanine (Cha), Naphthylalanine (Nal), 4-chlorophenylalanine (4cpa), 4-methoxyphenylalanine, 4-methylphenylalanine, 4-pyridylealanine, 3-pyridylalanine, 2-pyridylalanine, D-(−)-α-phenylglycine, homophenylalanine, 3-styrylalanine, O-benzyl-L-tyrosine, 4-benzoyl-L-phenylalanine, α-methyl-L-phenylalanine, α-methyl-D-phenylalanine or aminoindane;
wherein:
1) for $X^1$ to $X^{14}$ any natural amino acid listed may independently be optionally modified, and wherein
2) for $X^1$ to $X^{14}$ any modified amino acid listed may independently be optionally further modified and, in options 1) and 2), the modification in option 1) and the further modification in option 2) is optionally alkylation, esterification, N-alkyl amidation, substitution of hydrogen with any halo group or hydroxyl group or conjugation to an $R^3$ moiety through a conjugation linker $L_c$;
each of $L_1$ to $L_{13}$ is independently a linkage appropriate for joining two amino acids together, such as an amide bond, N-methylated amide, urea, ester, carbamate, peptoid, sulphonamide, alkene, thioamide, thioether, fluoroalkene, azapeptide difluoroketone or epoxide;
each $L_c$ is independently absent or is a conjugation linker which joins $R^1$ to $X^1$, $R^2$ to $X^1$, or an $R^3$ moiety to any of $X^1$ to $X^{14}$ and is selected from any linkage appropriate for joining $R^1$ to $X^1$, $R^2$ to $X^{14}$ or an $R^3$ moiety to any of $X^1$ to $X^{14}$;
or a pharmaceutically acceptable salt, solvate, amide, ester, prodrug, or deuterated analogue thereof.

2. A compound according to clause 1, comprising the sequence of Formula I:

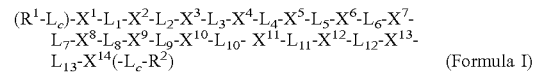

(Formula I)

wherein
$X^1$ is selected from the group consisting of V, I, L, M, P, Y, W, C, Q, Glp, and A;
$X^2$ is R;
$X^3$ is P;
$X^4$ is R;
$X^5$ is selected from the group consisting of A, V, I, Nle, and L;
$X^6$ is selected from the group consisting of Abu, M, P, and C;
$X^7$ is selected from the group consisting of H, R, and K;
$X^8$ is selected from the group consisting of R, K, and H;
$X^9$ is selected from the group consisting of Abu, M, P, and C;
$X^{10}$ is R, or K;
$X^{11}$ is selected from the group consisting of Aib, and P;
$X^{12}$ is R, K, or H;
$X^{13}$ is selected from the group consisting of A, V, I, Nle, and L;
$X^{14}$ is selected from the group consisting of C, F, other hydrophobic amino acids (Alanine (A), Isoleucine (I), Leucine (L), Methionine (M), Tyrosine (Y), Tryptophan (W), Valine (V), Proline (P), Glycine (G)), and $X^{14}$ may specifically be one of 3,4,5-trifluorophenylalanine (Tfpa or (3,4,5-trifluoro)F), β-cyclohexylalanine (Cha), Naphthylalanine (Nal), 4-chlorophenylalanine (4cpa), 4-methoxyphenylalanine, 4-methylphenylalanine, 4-pyridylealanine, 3-pyridylalanine, 2-pyridylalanine, D-(−)-α-phenylglycine, homophenylalanine, 3-styrylalanine, O-benzyl-L-tyrosine, 4-benzoyl-L-phenylalanine, α-methyl-L-phenylalanine, α-methyl-D-phenylalanine or aminoindane;
wherein:
1) for $X^1$ to $X^{14}$ any natural amino acid listed may independently be optionally modified, and wherein
2) for $X^1$ to $X^{14}$ any modified amino acid listed may independently be optionally further modified and, in options 1) and 2), the modification in option 1) and the further modification in option 2) is optionally alkylation, esterification, N-alkyl amidation, substitution of hydrogen with any halo group or hydroxyl group or conjugation to an $R^3$ moiety through a conjugation linker $L_c$;
each of $L_1$ to $L_{13}$ is independently a linkage appropriate for joining two amino acids together, such as an amide bond, N-methylated amide, urea, ester, carbamate, peptoid, sulphonamide, alkene, thioamide, thioether, fluoroalkene, azapeptide difluoroketone or epoxide;
$R^1$, $R^2$, and $R^3$ are independently absent or independently represent the rest of the compound, for example $R^1$, $R^2$, and $R^3$ can independently be a peptide, an acetyl, formyl, propinyl, biotin, myristoyl, or palmitoyl moiety, a methyl moiety, a saturated or unsaturated fatty acyl moiety, a polyethylene glycol polymer moiety, an immunoglobulin moiety, an immunoglobulin Fc domain moiety, albumin, a methylated moiety, an esterified moiety, or a portion of the natural apelin compound; each $L_c$ is independently absent or is a conjugation linker which joins $R^1$ to $X^1$, $R^2$ to $X^1$, or an $R^3$ moiety to any of $X^1$ to $X^{14}$ and is selected from any linkage appropriate for joining $R^1$ to $X^1$, $R^2$ to $X^{14}$ or an $R^3$ moiety to any of $X^1$ to $X^{14}$;

or a pharmaceutically acceptable salt, solvate, amide, ester, prodrug, or deuterated analogue thereof.

2a. A compound according to any preceding clause, wherein $X^1$ is selected from the group consisting of V, I, L, M, P, Y, W, C, Q, Glp, and A.

2b. A compound according to any preceding clause, wherein $X^2$ is R.

2c. A compound according to any preceding clause, wherein $X^3$ is P.

2d. A compound according to any preceding clause, wherein $X^4$ is R.

2e. A compound according to any preceding clause, wherein $X^5$ is selected from the group consisting of A, V, I, Nle, and L.

2f. A compound according to any preceding clause, wherein $X^6$ is selected from the group consisting of Abu, M, P, and C.

2g. A compound according to any preceding clause, wherein $X^7$ is selected from the group consisting of H, R, and K.

2h. A compound according to any preceding clause, wherein $X^8$ is selected from the group consisting of R, K, and H.

2i. A compound according to any preceding clause, wherein $X^9$ is selected from the group consisting of Abu, M, P, and C.

2j. A compound according to any preceding clause, wherein $X^{10}$ is selected from the group consisting of R, and K.

2k. A compound according to any preceding clause, wherein $X^{11}$ is selected from the group consisting of Aib, and P.

2l. A compound according to any preceding clause, wherein $X^{12}$ is selected from the group consisting of R, K, and H.

2m. A compound according to any preceding clause, wherein $X^{13}$ is selected from the group consisting of A, V, I, Nle, and L.

2n. A compound according to any preceding clause, wherein $X^{14}$ is selected from the group consisting of C, F, other hydrophobic amino acids (including Alanine (A), Isoleucine (I), Leucine (L), Methionine (M), Tyrosine (Y), Tryptophan (W), Valine (V), Proline (P), Glycine (G)), and $X^{14}$ may specifically be one of 3,4,5-trifluorophenylalanine (Tfpa or (3,4,5-trifluoro) F), p cyclohexylalanine (Cha), Naphthylalanine (Nal), 4-chlorophenylalanine (4cpa), 4 methoxyphenylalanine, 4-methylphenylalanine, 4-pyridylealanine, 3-pyridylalanine, 2 pyridylalanine, D-(–)-α-phenylglycine, homophenylalanine, 3-styrylalanine, O benzyl L tyrosine, 4-benzoyl-L-phenylalanine, α-methyl-L-phenylalanine, α-methyl-D-phenylalanine or aminoindane.

3. A compound according to any preceding clause, wherein the compound is a compound of formula (I) or a pharmaceutically acceptable salt, solvate, or deuterated analogue thereof.

4. A compound according to any preceding clause, wherein the compound is a compound of formula (I) or a pharmaceutically acceptable salt or solvate thereof.

5. A compound according to any preceding clause, wherein one or more of $X^1$ to $X^{14}$ is each independently linked to an $R^3$ moiety through a conjugation linker $L_c$.

6. A compound according to clause 5, wherein one or more of $X^1$, $X^6$, $X^9$, and $X^{14}$ is each independently linked to an $R^3$ moiety through a conjugation linker $L_c$, optionally wherein the conjugation linker is a maleimide or pegylated maleimide, optionally wherein $R^3$ is a fatty acid, pegylated, a peptide, a polypeptide, or an antibody molecule.

7. A compound according to clauses 1-4, wherein none of $X^1$ to $X^{14}$ is linked to $R^3$ through a conjugation linker $L_c$.

8. A compound according to any preceding clause, wherein one of $(R^1-L_c)$ and $(-L_c-R^2)$ is absent.

9. A compound according to any preceding clause, wherein both of $(R^1-L_c)$ and $(-L_c-R^2)$ are absent such that the sequence terminates at $X^1$ and $X^{14}$.

10. A compound according to any preceding clause, wherein for each of $X^1$ to $X^{14}$ none of the natural amino acids listed are modified and none of the modified amino acids listed are further modified.

11. A compound according to any preceding clause, wherein each of $L_1$ to $L_{14}$ is an amide or N-methylated amide linkage, preferably an amide linkage.

12. A compound according to any preceding clause, wherein $X^1$ is C, Q, Glp, or A.

12a. A compound according to any preceding clause, wherein $X^1$ is C.

12b. A compound according to any preceding clause, wherein $X^1$ is Q.

12c. A compound according to any preceding clause, wherein $X^1$ is Glp.

12d. A compound according to any preceding clause, wherein $X^1$ is A.

13. A compound according to any preceding clause, wherein $X^2$ is R.

14. A compounds according to any preceding clause, wherein $X^3$ is P.

15. A compound according to any preceding clause, wherein $X^4$ is R.

16. A compound according to any preceding clause, wherein $X^2$ is R and said R is modified by methylation.

17. A compound according to any preceding clause, wherein $X^4$ is R and said R is modified by methylation.

18. A compound according to any preceding clause, wherein $X^5$ is selected from the group consisting of Nle and L.

19. A compound according to any preceding clause, wherein $X^{13}$ is selected from the group consisting of Nle and L.

20. A compound according to any preceding clause, wherein $X^6$ is selected from the group consisting of C and Abu.

21. A compound according to any preceding clause, wherein $X^9$ is independently selected from the group consisting of C and Abu 22. A compound according to any preceding clause, wherein $X^7$ is K and $X^8$ is H, or wherein $X^7$ is H and $X^8$ is K, or wherein $X^7$ is A and $X^8$ is K, or wherein $X^7$ is K and $X^8$ is A.

23. A compound according to any preceding clause, wherein one of $X^7$ and $X^8$ is H and the other is K.

24. A compound according to any preceding clause, wherein $X^{10}$ is R.

25. A compound according to any preceding clause, wherein $X^{10}$ and $X^{12}$ is R.

26. A compound according to any preceding clause, wherein $X^{11}$ is selected from the group consisting of P and Aib.
27. A compound according to any preceding clause, wherein $X^{14}$ is selected from C and (3,4,5-trifluoro-)F, preferably (3,4,5-trifluoro-)F.
28. A compound according to any preceding clause, wherein $X^1$ is C, optionally wherein $R^1$ is myristoyl.
29. A compound according to any preceding clause, wherein $X^5$ is Ne.
30. A compound according to any preceding clause, wherein $X^6$ is Abu.
31. A compound according to any preceding clause, wherein $X^7$ is K and $X^3$ is H.
32. A compound according to any preceding clause, wherein $X^9$ is Abu.
33. A compound according to any preceding clause, wherein $X^{10}$ is R.
34. A compound according to any preceding clause, wherein $X^{11}$ is Aib.
35. A compound according to any preceding clause, wherein $X^{12}$ is R.
36. A compound according to any preceding clause, wherein $X^{13}$ is Ne.
37. A compound according to any preceding clause, wherein $X^{14}$ is (3,4,5-trifluoro)F.
37a. A compound according to any preceding clause, wherein $X^1$ is modified.
37b. A compound according to any preceding clause, wherein $X^1$ is not modified.
37c. A compound according to any preceding clause, wherein $X^2$ is modified.
37d. A compound according to any preceding clause, wherein $X^2$ is not modified.
37e. A compound according to any preceding clause, wherein $X^3$ is modified.
37f. A compound according to any preceding clause, wherein $X^3$ is not modified.
37g. A compound according to any preceding clause, wherein $X^4$ is modified.
37h. A compound according to any preceding clause, wherein $X^4$ is not modified.
37i. A compound according to any preceding clause, wherein $X^5$ is modified.
37j. A compound according to any preceding clause, wherein $X^5$ is not modified.
37k. A compound according to any preceding clause, wherein $X^6$ is modified.
37l. A compound according to any preceding clause, wherein $X^6$ is not modified.
37m. A compound according to any preceding clause, wherein $X^7$ is modified.
37n. A compound according to any preceding clause, wherein $X^7$ is not modified.
37o. A compound according to any preceding clause, wherein $X^8$ is modified.
37p. A compound according to any preceding clause, wherein $X^8$ is not modified.
37q. A compound according to any preceding clause, wherein $X^9$ is modified.
37r. A compound according to any preceding clause, wherein $X^9$ is not modified.
37s. A compound according to any preceding clause, wherein $X^{10}$ is modified.
37t. A compound according to any preceding clause, wherein $X^{10}$ is not modified.
37u. A compound according to any preceding clause, wherein $X^{11}$ is modified.
37v. A compound according to any preceding clause, wherein $X^{11}$ is not modified.
37w. A compound according to any preceding clause, wherein $X^{12}$ is modified.
37x. A compound according to any preceding clause, wherein $X^{12}$ is not modified.
37y. A compound according to any preceding clause, wherein $X^{13}$ is modified.
37z. A compound according to any preceding clause, wherein $X^{13}$ is not modified.
37aa. A compound according to any preceding clause, wherein $X^{14}$ is modified.
37ab. A compound according to any preceding clause, wherein $X^{14}$ is not modified.
38. A compound according to any preceding clause, wherein one or more of $X^1$ to $X^{14}$ is C, R, or K and is modified, wherein the modification comprises directly or indirectly joining said C, R or K to a protein or fatty acid.
39. A compound according to any preceding clause, wherein $R^1$ is a C1 to C25 saturated or unsaturated fatty acyl moiety optionally bound to $X^1$ through a conjugation linker $L_c$.
40. A compound according to any preceding clause, wherein the fatty acyl moiety comprises a fatty acyl group selected from the group consisting of Butanoyl, Hexanoyl, Octanoyl, Decanoyl, Dodecanoyl, Tridecanoyl, Tetradecanoyl, Pentadecanoyl, Hexadecanoyl, Heptadecanoyl, Octadecanoyl, Octadecandioyl, Octanedioyl, Decanedioyl, Dodecanedioyl, Hexanedioyl, Butanedioyl, Tetradecanedioyl, and Hexadecanedioyl.
41. A compound according to any one of clauses 1-38, wherein $R^1$ is a polyethyleneglycol polymer moiety optionally bound to $X^1$ through a conjugation linker $L_c$.
42. A compound according to clause 41, wherein the polyethyleneglycol polymer moiety comprises a 5 kDa, 10 kDa, or 20 kDa polyethylene glycol polymer.
43. A compound according to any preceding clause, wherein at least one conjugation linker $L_c$ is present and comprises 3-mercaptopropanoic acid.
44. A compound according to any one of clauses 1-38, wherein $R^1$ is an immunoglobulin moiety or an immunoglobulin Fc domain moiety optionally bound to $X^1$ through a conjugation linker $L_c$.
45. A compound according to any preceding clause, wherein at least one conjugation linker $L_c$ is present and is a peptidyl linker.
46. A compound according to any one of clauses 1-44, wherein at least one conjugation linker $L_c$ is present and is a non-peptidyl linker.
47. A compound according to clause 46, wherein the non-peptidyl conjugation linker $L_c$ comprises a polyethylene glycol polymer.
48. A compound according to any preceding clause, wherein at least on conjugation linker $L_c$ is present and comprises a maleimide moiety, pegylated maleimide moiety or thioether.
49. A compound according to any one of clauses 1-38 and 41-48, wherein $X^1$ is C and $R^1$ is a protein, for example a protein selected from albumin and albudAb.
50. A compound according to any preceding clause, wherein the compound is selected from the following table:

| Comp. No. | (R¹-L_c) | X¹ | X² | X³ | X⁴ | X⁵ | X⁶ | X⁷ | X⁸ | X⁹ | X¹⁰ | X¹¹ | X¹² | X¹³ | X¹⁴ | (R²-L_c) |
|---|---|---|---|---|---|---|---|---|---|---|---|---|---|---|---|---|
| MM107 | — | C | R | P | R | L | C | H | K | C | R | P | R | L | C | — |
| MM108 | — | C | R | P | R | L | C | K | H | C | R | P | R | L | C | — |
| MM193 | — | C | R | P | R | Nle | C | K | H | C | R | Aib | R | Nle | (3,4,5-trifluoro-)F | — |
| MM262 | — | Q | R | P | R | Nle | C | K | H | C | R | Aib | R | Nle | (3,4,5-trifluoro-)F | — |
| MM297 | — | Glp | R | P | R | Nle | C | K | H | C | R | Aib | R | Nle | (3,4,5-trifluoro-)F | — |
| MM298 | — | C | R | P | R | Nle | Abu | K | H | C | R | Aib | R | Nle | (3,4,5-trifluoro-)F | — |
| MM299 | — | C | R | P | R | Nle | C | K | H | Abu | R | Aib | R | Nle | (3,4,5-trifluoro-)F | — |
| MM300 | Myristoyl | C | R | P | R | Nle | C | K | H | C | R | Aib | R | Nle | (3,4,5-trifluoro-)F | — |
| MM301 | — | Glp | R | P | R | Nle | Abu | K | H | Abu | R | Aib | R | Nle | (3,4,5-trifluoro-)F | — |
| MM302 | — | C | R | P | R | Nle | C | H | K | C | R | Aib | R | Nle | (3,4,5-trifluoro-)F | — |
| MM312 | — | A | R | P | R | Nle | C | K | H | Abu | R | Aib | R | Nle | (3,4,5-trifluoro-)F | — |
| MM313 | Ac | A | R | P | R | Nle | C | K | H | Abu | R | Aib | R | Nle | (3,4,5-trifluoro-)F | — |
| MM314 | — | A | R | P | R | Nle | Abu | K | H | Abu | R | Aib | R | Nle | (3,4,5-trifluoro-)F | — |
| MM315 | Myristoyl | A | R | P | R | Nle | Abu | K | H | Abu | R | Aib | R | Nle | (3,4,5-trifluoro-)F | — |
| MM316 | Myristoyl | A | R | P | R | Nle | Abu | H | K | Abu | R | Aib | R | Nle | (3,4,5-trifluoro-)F | — |

51. The compound of any one of the preceding clauses, wherein said compound is an apelin receptor antagonist.

52. A pharmaceutical composition comprising a compound of any one of the preceding clauses and a pharmaceutically acceptable diluent, excipient, or carrier.

53. A pharmaceutical composition according to clause 52, wherein the composition is formulated for:
   (a) systemic delivery such as intravenous, subcutaneous, intramuscular, intraperitoneal, intranasal, intravaginal, intrarectal, intrapulmonary, intra-cranial, or oral delivery;
   (b) local delivery such as topical, or iontophoretic delivery;
   (c) transdermal delivery such as by a patch;
   (d) inhalation via the lung; or
   (e) intra-ocular delivery including topical, injectable, contact lenses-releasing medications, biodegradable micro- and nanoparticles, and surgically implanted systems.

54. A compound or composition according to any one of the preceding clauses for use in medicine.

55. A compound or composition according to any one of clauses 1-53, for use in the treatment of a disorder or disease selected from the group consisting of a tumor, cancer, metabolic diseases, diabetes, diseases involving angiogenesis and lymphangiogenesis, diseases of obesity including reduction of dietary sugar uptake, cardiovascular disease, neoplasia, peripheral vascular disease, septic shock, hypotension, preeclampsia, ocular degeneration, idiopathic pulmonary fibrosis, inflammatory disease (such as arthritis and inflammatory bowel disease), avascular or ischemic insult, eczema, ulcers, lymphedema, bone diseases, vascular hyperplasia, hemangioma, proteinuric renal disease, diabetic retinopathy, diseases of choroidal vasculature (AMD), macular degenerative disease, psoriasis, endometriosis, glioma, glioblastoma, glioblastoma multiforma, colorectal cancer, renal carcinoma, lung cancer, mammary/breast cancer, endometriosis, any disease involving angiogenesis, and HIV infection.

56. A compound or composition according to any one of clauses 1-53, for use in the treatment of a disorder or disease selected from the group consisting of cancer, colorectal cancer, lung cancer, mammary/breast cancer, glioma, glioblastoma, glioblastoma multiforma, renal carcinoma, ocular degeneration, and/or diabetic retinopathy.

56a. A compound or composition according to any one of clauses 1-53, for use in the treatment of glioma, preferably astrocytoma, oligodendroglioma, or ependymoma, in a patient.

57. A compound or composition according to any one of clauses 1-53, for use in the treatment of cancer in a patient.

58. A compound or composition according to any one of clauses 1-53, for use in the treatment of glioblastoma, preferably glioblastoma multiforma in a patient.

59. A compound or composition according to any one of clauses 1-53, for use in the treatment of glioblastoma in a patient.

60. A compound or composition according to any one of clauses 1-53, for use in the treatment of lung cancer in a patient.

61. A compound or composition according to any one of clauses 1-53, for use in the treatment of mammary/breast cancer in a patient.

62. A compound or composition according to any one of clauses 1-53, for use in the treatment of endometriosis in a patient.

63. A compound or composition according to any one of clauses 1-53, for use in the treatment of colorectal cancer in a patient.

64. A compound or composition according to any one of clauses 1-53, for use in the treatment of renal carcinoma in a patient.

65. A compound or composition according to any one of clauses 1-53, for use in the treatment of ocular degeneration in a patient.

66. A compound or composition according to any one of clauses 1-53, for use in the treatment of diabetic retinopathy in a patient.

67. A compound or composition according to any one of clauses 1-53, for use in the treatment of a tumor or disease caused by abnormal angiogenesis in a patient in need thereof, optionally wherein administration of the compound modifies tumor cell growth or endothelial growth in the patient.

68. A compound or composition according to any one of clauses 1-53, for use in the treatment of a tumor in a subject, said method comprising the steps of:
   a) identifying the human or animal subject in need of treatment of a tumor;
   b) determining sensitivity of the mammal to treatment with an apelin receptor antagonist compound as defined in any one of clauses 1-51 or composition as defined in clause 52 or 53; and c) administering a therapeutically effective amount of said compound or composition to the subject.
69. The compound or composition for use according to any one of clauses 67-68, wherein the tumor is a glioblastoma.
70. A compound or composition according to any one of clauses 1-53, for use in the treatment of inhibiting growth, invasion and/or proliferation of tumor cells in a subject, wherein said method comprises administering said compound to the subject in need thereof.
71. The compound or composition for use in any one of clauses 67-70, wherein said treatment comprises administering the compound or composition to the patient intravenously.
72. The compound or composition for use in any one of clauses 67-71, wherein said treatment comprises administering the compound or composition to a patient who has undergone tumor excision surgery and wherein the compound or composition is administered at the site of tumor excision.
73. The compound or composition for use in clauses 67-72, wherein said treatment comprises administering the compound or composition to the patient in combination with one or more additional anti-cancer agents.
74. The compound or composition for use in clause 73, wherein said compound or composition and said one or more anti-cancer agents are each administered to the patient simultaneously, separately, or sequentially.
75. The compound or composition for use in clause 74, wherein the one or more anti-cancer agents are selected from the group consisting of bevacizumab, temozolomide, vincristine, irinotecan, procarbazine, BiCNU, and carmustine.
76. The compound or composition for use as claimed in clause 74, wherein the anti-cancer agent is temozolomide.
77. The compound or composition for use in clause 73, wherein the anti-cancer agents are chemotherapeutic agents.
78. The compound or composition for use in clause 77, wherein the chemotherapeutic agents are selected from the group consisting of temozolomide, etoposide, doxorubicin, cisplatin, paclitaxel, carmustine, lomustine, ceramide and phosphorylcholine, and other suitable anti-cancer agents including kinase inhibitors.
79. The compound or composition for use in any one of clauses 67-78, wherein said treatment further comprises subjecting the patient to radiation therapy.
80. A method of treating disease or disorder in a patient, said method comprising administering a compound according to any one of clauses 1 to 51 or a composition according to any one of clauses 52 to 53 to said patient.
81. A method of treating a tumor, cancer, metabolic diseases, diabetes, diseases involving angiogenesis and lymphangiogenesis, diseases of obesity including reduction of dietary sugar uptake, cardiovascular disease, neoplasia, peripheral vascular disease, septic shock, hypotension, preeclampsia, ocular degeneration, idiopathic pulmonary fibrosis, inflammatory disease (such as arthritis and inflammatory bowel disease), avascular or ischemic insult, eczema, ulcers, lymphedema, bone diseases, vascular hyperplasia, hemangioma, proteinuric renal disease, diabetic retinopathy, diseases of choroidal vasculature (AMD), macular degenerative disease, psoriasis, endometriosis, glioma, glioblastoma, glioblastoma multiforma, colorectal cancer, renal carcinoma, lung cancer, mammary/breast cancer, endometriosis, any disease involving angiogenesis, and HIV infection, said method comprising administering a compound according to any one of clauses 1 to 51 or a composition according to any one of clauses 52 to 53 to said patient.
82. A method of treating cancer, colorectal cancer, lung cancer, mammary/breast cancer, glioma, glioblastoma, glioblastoma multiforma, renal carcinoma, ocular degeneration, and/or diabetic retinopathy in a patient, said method comprising administering a compound according to any one of clauses 1 to 51 or a composition according to any one of clauses 52 to 53 to said patient.
82a. A method of treating glioma, preferably astrocytoma, oligodendroglioma, or ependymoma, said method comprising administering a compound according to any one of clauses 1 to 51 or a composition according to any one of clauses 52 to 53 to said patient.
83. A method of treating glioblastoma, preferably glioblastoma multiforma in a patient, said method comprising administering a compound according to any one of clauses 1 to 51 or a composition according to any one of clauses 52 to 53 to said patient.
84. A method of treating cancer, preferably lung cancer in a patient, said method comprising administering a compound according to any one of clauses 1 to 51 or a composition according to any one of clauses 52 to 53 to said patient.
85. A method of treating cancer, preferably mammary/breast cancer in a patient, said method comprising administering a compound according to any one of clauses 1 to 51 or a composition according to any one of clauses 52 to 53 to said patient.
86. A method of treating endometriosis in a patient, said method comprising administering a compound according to any one of clauses 1 to 51 or a composition according to any one of clauses 52 to 53 to said patient.
87. A method of treating colorectal cancer in a patient, said method comprising administering a compound according to any one of clauses 1 to 51 or a composition according to any one of clauses 52 to 53 to said patient.
88. A method of treating renal carcinoma in a patient, said method comprising administering a compound according to any one of clauses 1 to 51 or a composition according to any one of clauses 52 to 53 to said patient.
89. A method of treating ocular degeneration in a patient, said method comprising administering a compound according to any one of clauses 1 to 51 or a composition according to any one of clauses 52 to 53 to said patient.
90. A method of treating diabetic retinopathy in a patient, said method comprising administering a compound according to any one of clauses 1 to 51 or a composition according to any one of clauses 52 to 53 to said patient.
91. A method of treating a tumor or disease caused by abnormal angiogenesis in a patient in need thereof, optionally wherein administration of the compound modifies tumor cell growth or endothelial growth in the patient, said method comprising administering a compound according to any one of clauses 1 to 51 or a composition according to any one of clauses 52 to 53 to said patient.

92. A method of treating a tumor in a subject, said method comprising the steps of:
   a) identifying the human or animal subject in need of treatment of a tumor;
   b) determining sensitivity of the mammal to treatment with an apelin receptor antagonist compound as defined in any one of clauses 1-51 or composition as defined in clause 52 or 53; and
   c) administering a therapeutically effective amount of said apelin receptor antagonist compound or composition to the subject.
93. The method of clauses 91 or 92, wherein the tumor is a glioblastoma.
94. A method of inhibiting growth, invasion and/or proliferation of tumor cells in a subject, wherein said method comprises administering a compound according to any one of clauses 1 to 51 or a composition according to any one of clauses 52 to 53 to the subject in need thereof.
95. The method of any of clauses 91-94, comprising administering the compound or composition to the patient intravenously.
96. The method of any of clauses 91-95, wherein said method comprises administering the compound or composition to a patient who has undergone tumor excision surgery and wherein the compound or composition is administered at the site of tumor excision.
97. The method of any of clauses 91-96, wherein said method comprises administering the compound or composition to the patient in combination with one or more additional anti-cancer agents.
98. The method of clause 97, wherein said compound or composition and said one or more anti-cancer agents are each administered to the patient simultaneously, separately, or sequentially.
99. The method of clause 98, wherein the one or more anti-cancer agents are selected from the group consisting of bevacizumab, temozolomide, vincristine, irinotecan, procarbazine, BiCNU, and carmustine.
100. The method of clause 98, wherein the anti-cancer agent is temozolomide.
101. The compound or composition for use in clause 97, wherein the anti-cancer agents are chemotherapeutic agents.
102. The method of clause 101, wherein the chemotherapeutic agents are selected from the group consisting of temozolomide, etoposide, doxorubicin, cisplatin, paclitaxel, carmustine, lomustine, ceramide and phosphorylcholine, and other suitable anti-cancer agents including kinase inhibitors.
103. The method of any of clauses 91-102, wherein said method further comprises subjecting the patient to radiation therapy.
104. Use of a substance or composition according to clauses 1-53 for the manufacture of a medicament for the treatment or a disease or disorder selected from a tumor, cancer, metabolic diseases, diabetes, diseases involving angiogenesis and lymphangiogenesis, diseases of obesity including reduction of dietary sugar uptake, cardiovascular disease, neoplasia, peripheral vascular disease, septic shock, hypotension, preeclampsia, ocular degeneration, idiopathic pulmonary fibrosis, inflammatory disease (such as arthritis and inflammatory bowel disease), avascular or ischemic insult, eczema, ulcers, lymphedema, bone diseases, vascular hyperplasia, hemangioma, proteinuric renal disease, diabetic retinopathy, diseases of choroidal vasculature (AMD), macular degenerative disease, psoriasis, endometriosis, glioma, glioblastoma, glioblastoma multiforma, colorectal cancer, renal carcinoma, lung cancer, mammary/breast cancer, endometriosis, any disease involving angiogenesis, and HIV infection.
105. A compound comprising 6 contiguously linked ($L_{1-14}$) amino acids ($X^{1-14}$) as defined from formula I, wherein the sequence overlaps with part of one of SEQ. ID NOS 3-17.
106. A compound comprising 7 contiguously linked ($L_{1-14}$) amino acids ($X^{1-14}$) as defined from formula I, wherein the sequence overlaps with part of one of SEQ. ID NOS 3-17.
107. A compound comprising 8 contiguously linked ($L_{1-14}$) amino acids ($X^{1-14}$) as defined from formula I, wherein the sequence overlaps with part of one of SEQ. ID NOS 3-17.
108. A compound comprising 9 contiguously linked ($L_{1-14}$) amino acids ($X^{1-14}$) as defined from formula I, wherein the sequence overlaps with part of one of SEQ. ID NOS 3-17.
109. A compound comprising 10 contiguously linked ($L_{1-14}$) amino acids ($X^{1-14}$) as defined from formula I, wherein the sequence overlaps with part of one of SEQ. ID NOS 3-17.
110. A compound comprising 11 contiguously linked ($L_{1-14}$) amino acids ($X^{1-14}$) as defined from formula I, wherein the sequence overlaps with part of one of SEQ. ID NOS 3-17.
111. A compound comprising 12 contiguously linked ($L_{1-14}$) amino acids ($X^{1-14}$) as defined from formula I, wherein the sequence overlaps with part of one of SEQ. ID NOS 3-17.
112. A compound comprising 13 contiguously linked ($L_{1-14}$) amino acids ($X^{1-14}$) as defined from formula I, wherein the sequence overlaps with part of one of SEQ. ID NOS 3-17.
113. A compound of clauses 105-112, for use in clauses 53-104.
114. A compound comprising the sequence of Formula I:

$$(R^1\text{-}L_c)\text{-}X^1\text{-}L_1\text{-}X^2\text{-}L_2\text{-}X^3\text{-}L_3\text{-}X^4\text{-}L_4\text{-}X^5\text{-}L_5\text{-}X^6\text{-}L_6\text{-}X^7\text{-}L_7\text{-}X^8\text{-}L_8\text{-}X^9\text{-}L_9\text{-}X^{10}\text{-}L_{10}\text{-}X^{11}\text{-}L_{11}\text{-}X^{12}\text{-}L_{12}\text{-}X^{13}\text{-}L_{13}\text{-}X^{14}(\text{-}L_c\text{-}R^2) \quad \text{(Formula I)}$$

wherein $X^1$ is any amino acid;

$X^2$ is selected from the group consisting of R, H, and K;

$X^3$ is p;

$X^4$ is R;

$X^5$ is selected from the group consisting of Nle, L, A, V, I, M, F, Y, and W;

$X^6$ is selected from the group consisting of Abu, C, A, V, I, L, M, F, Y, W, and P;

$X^7$ is selected from the group consisting of H, K, A, V, I, L, M, F, Y, W, and R;

$X^3$ is selected from the group consisting of K, H, A, V, I, L, M, F, Y, W, and R;

$X^9$ is selected from the group consisting of Abu, C, A, V, I, L, M, F, Y, W, and P;

$X^{10}$ is selected from the group consisting of R, H, and K;

$X^{11}$ is selected from the group consisting of Aib, and P;

$X^{12}$ is selected from the group consisting of R, H, and K;

$X^{13}$ is selected from the group consisting of Nle, Aib, L, V, I, and A;

$X^{14}$ is selected from the group consisting of none, C, F, other hydrophobic amino acids (including Alanine (A), Isoleucine (I), Leucine (L), Methionine (M), Tyrosine (Y), Tryptophan (W), Valine (V), Proline (P), Glycine (G)), and $X^{14}$ may specifically be one of 3,4,5-trifluorophenylalanine (Tfpa or (3,4,5-trifluoro)F), β-cyclohexylalanine (Cha), Naphthylalanine (Nal), 4-chlorophenylalanine (4cpa), 4-methoxyphenylalanine, 4-methylphenylalanine, 4-pyridylealanine, 3-pyridylalanine, 2-pyridylalanine, D-(−)-α-phenylglycine, homophenylalanine, 3-styrylalanine, O-benzyl-L-tyrosine, 4-benzoyl-L-phenylalanine, α-methyl-L-phenylalanine, α-methyl-D-phenylalanine, aminoindane, 2-aminoindane, O-benzyltyrosine, or 4-Aminopiperidine-4-carboxylic acid;

wherein:
1) for $X^1$ to $X^{14}$ any natural amino acid listed may independently be optionally modified, and wherein 2) for $X^1$ to $X^{14}$ any modified amino acid listed may independently be optionally further modified and, in options 1) and 2), the modification in option 1) and the further modification in option 2) is optionally alkylation, esterification, N-alkyl amidation, substitution of hydrogen with any halo group or hydroxyl group or conjugation to an $R^3$ moiety through a conjugation linker $L_c$;

each of $L_1$ to $L_{13}$ is independently a linkage appropriate for joining two amino acids together, such as an amide bond, N-methylated amide, urea, ester, carbamate, peptoid, sulphonamide, alkene, thioamide, thioether, fluoroalkene, azapeptide difluoroketone or epoxide;

$R^1$, $R^2$, and $R^3$ are independently absent or independently represent the rest of the compound, for example $R^1$, $R^2$, and $R^3$ can independently be a peptide, an acetyl, formyl, propinyl, biotin, myristoyl, or palmitoyl moiety, a methyl moiety, a saturated or unsaturated fatty acyl moiety, a polyethylene glycol polymer moiety, an immunoglobulin moiety, an immunoglobulin Fc domain moiety, albumin, a methylated moiety, an esterified moiety, or a portion of the natural apelin compound;

each $L_c$ is independently absent or is a conjugation linker which joins $R^1$ to $X^1$, $R^2$ to $X^1$, or an $R^3$ moiety to any of $X^1$ to $X^{14}$ and is selected from any linkage appropriate for joining $R^1$ to $X^1$, $R^2$ to $X^{14}$ or an $R^3$ moiety to any of $X^1$ to $X^{14}$;

or a pharmaceutically acceptable salt, solvate, amide, ester, prodrug, or deuterated analogue thereof.

115. A compound according to clause 114 as further defined in any one of clauses 2 to 53.

116. A compound according to clause 115 for use in any one of clauses 54-104.

117. A compound according to any one of clauses 1 to 53, 105,-112, or 114-115, or a compound for use according to any one of clauses 54-104, 113 or 116, wherein $X^7$ is K and is modified wherein the modification comprises directly or indirectly joining K to a fatty acid

REFERENCES

[1] B. F. O'dowd, M. Heiber, A. Chan, H. H. Q. Heng, L. C. Tsui, J. L. Kennedy, X. M. Shi, A. Petronis, S. R. George, T. Nguyen, *Gene* 1993, 136, 355-360.

[2] Tatemoto, K. et al. (1998) Isolation and characterization of a novel endogenous peptide ligand for the human APJ receptor. *Biochem. Biophys. Res. Commun.* 251, 471-476

[3] Maguire J. J. [Pyr⁴]apelin-13 identified as the predominant apelin isoform in the human heart: vasoactive mechanisms and inotropic action in disease. *Hypertension.* 2009; 54:598-604.

[4] Zhen E. Y. Pyrogutamy apelin-13 identified as the major apelin isoform in human plasma. *Anal. Biochem.* 2013, 442, 1-9.

[5] Yang P. R., Maguire J. J., Davenport A. P. Apelin, Elabela/Todder, and biased agonists as novel therapeutic agents in the cardiovascular system *Trends Pharmacol Sci* 2015, 36, 560-567.

[6] O'Carroll, A. M.; Loait, S. J.; Harris, L. E.; Pope, G. R., The apelin receptor APJ: journey from an orphan to a multifaceted regulator of homeostasis. *J Endocrinol* 2013, 219 (1), R13-R35.

[7] Pitkin, S. L. et al. International Union of Basic and Clinical Pharmacology. LXXIV. Apelin receptor nomenclature, distribution, pharmacology, and function. *Pharmacol. Rev.* 2010, 62, 331-342

[8] Chng S C, Ho L, Tian J, Reversade B. ELABELA: a hormone essential for heart development signals via the apelin receptor. *Dev Cell.* 2013, 27, 672-680.

[9] Pauli A, Norris M L, Valen E, Chew G L, Gagnon J A, Zimmerman S, Mitchell A, Ma J, Dubrulle J, Reyon D, Tsai S Q, Joung J K, Saghatelian A, Schier A F. Toddler: an embryonic signal that promotes cell movement via Apelin receptors. *Science.* 2014, 343, 1248636.

[10] Kleinz, M. J.; Davenport, A. P., Emerging roles of apelin in biology and medicine. *Pharmacol Therapeut* 2005, 107(2), 198-211.

[11] Sorli, S. C.; van den Berghe, L.; Masri, B.; Knibieher, B.; Audigier, Y., Therapeutic potential of interfering with apelin signalling. *Drug Discov Today* 2006, 11 (23-24), 1100-1106.

[12] Charles, C. J., The apelin peptides as putative targets in cardiovascular drug discovery and development. *Expert Opin Drug Dis* 2008, 3(1), 51-64.

[13] Barnes, G.; Japp, A. G.; Newby, D. E., Translational promise of the apeline-APJ system. *Heart* 2010, 96(13), 1011-1016.

[14] Castan-Laurell, I.; Dray, C.; Attane, C.; Duparc, T.; Knauf, C.; Valet, P., Apelin, diabetes, and obesity. *Endocrine* 2011, 40(1), 1-9.

[15] O'Carroll, A. M.; Loait, S. J.; Harris, L. E.; Pope, G. R., The apelin receptor APJ: journey from an orphan to a multifaceted regulator of homeostasis. *J Endocrino* 2013, 219(1), R13-R35.

[16] Cao, J. G.; Li, H. N.; Chen, L. X., Targeting Drugs to APJ Receptor: The Prospect of Treatment of Hypertension and Other Cardiovascular Diseases. *Curr Drug Targets* 2015, 16(2), 148-155.

[17] Cao, J. G.; Li, L. F.; Chen, L. X., Apelin/APJ: Vascular Function Regulatory Factor and New Targets for Drug Treatment. *Prog Biochem Biophys* 2015, 42(8), 721-732.

[18] Chen, Z.; Wu, D.; Li, L. F.; Chen, L. X., Apelin/APJ System: A Novel Therapeutic Target for Myocardial Ischemia/Reperfusion Injury. *DNA Cell Biol* 2016, 35(12), 766-775.

[19] Hu, H. L.; He, L.; Li, L. F.; Chen, L. X., Apelin/APJ system as a therapeutic target in diabetes and its complications. *Mol Genet Metab* 2016, 119(1-2), 20-27.

[20] Salska, A.; Chizynski, K., Apelin—a potential target in the diagnosis and treatment of the diseases of civilization. *Acta Cardio* 2016, 71(5), 505-517.

[21] Liu, J. Q.; Liu, M. Q.; Chen, L. X., Novel pathogenesis: regulation of apoptosis by Apelin/APJ system. *Acta Bioch Bioph Sin* 2017, 49(6), 471-478.

[22] Wu, L. L.; Chen, L. X.; Li, L. F., Apelin/APJ system: A novel promising therapy target for pathological angiogenesis. *Clin Chim Acta* 2017, 466, 78-84.

[23] Kalin, R. E.; Kretz, M. P.; Meyer, A. M.; Kispert, A.; Heppner, F. L.; Brandli, A. W., Paracrine and autocrine mechanisms of apelin signaling govern embryonic and tumor angiogenesis. *Dev Biol* 2007, 305(2), 599-614.

[24] Sorli, S. C.; Le Gonidec, S.; Knibiehler, B.; Audigier, Y., Apelin is a potent activator of tumour neoangiogenesis. *Oncogene* 2007, 26(55), 7692-7699.

[25] Wang, Z. Q.; Greeley, G. H.; Qiu, S. M., Immunohistochemical localization of apelin in human normal breast and breast carcinoma. *J Mo Histo* 2008, 39(1), 121-124.

[26] Berta, J.; Kenessey, I.; Dobos, J.; Tovari, J.; Klepetko, W.; Ankersmit, H. J.; Hegedus, B.; Renyi-Vamos, F.; Varga, J.; Lorincz, Z.; Paku, S.; Ostoros, G.; Rozsas, A.; Timar, J.; Dome, B., Apelin Expression in Human Non-small Cell Lung Cancer Role in Angiogenesis and Prognosis. *J Thorac Onco* 2010, 5(8), 1120-1129.

[27] Rayalam, S.; Della-Fera, M. A.; Kasser, T.; Warren, W.; Baile, C. A., Emerging Role of Apelin as a Therapeutic Target in Cancer: A Patent Review. *Recent Pat Anti-Canc* 2011, 6(3), 367-372.

[28] Choi, Y. S.; Yang, H. I.; Cho, S.; Jung, J. A.; Jeon, Y. E.; Kim, H. Y.; Seo, S. K.; Lee, B. S., Serum asymmetric dimethyarginine, apelin, and tumor necrosis factor-alpha levels in non-obese women with polycystic ovary syndrome. *Steroids* 2012, 77(13), 1352-1358.

[29] Heo, K.; Kim, Y. H.; Sung, H. J.; Li, H. Y.; Yoo, C. W.; Kim, J. Y.; Park, J. Y.; Lee, U. L.; Nam, B. H.; Kim, E. O.; Kim, S. Y.; Lee, S. H.; Park, J. B.; Choi, S. W., Hypoxia-induced up-regulation of apelin is associated with a poor prognosis in oral squamous cell carcinoma patients. *Oral Oncol* 2012, 48(6), 500-506.

[30] Kidoya, H.; Kunii, N.; Naito, H.; Muramatsu, F.; Okamoto, Y.; Nakayama, T.; Takakura, N., The apelin/APJ system induces maturation of the tumor vasculature and improves the efficiency of immune therapy. *Oncogene* 2012, 31(27), 3254-3264.

[31] Farid, R. M.; Abu-Zeid, R. M.; El-Tawil, A., Apelin Expression in the Fibrosis-Cancer Axis in Hepatitis C Virus Patients. *Hepatology* 2013, 58, 1189a-1189a.

[32] Kawahara, H.; Naito, H.; Takara, K.; Wakabayashi, T.; Kidoya, H.; Takakura, N., Tumor Endothelial Cell-Specific Drug Delivery System Using Apelin-Conjugated Liposomes. *Plos One* 2013, 8(6).

[33] Kidova, H.; Kunii, N.; Naito, H.; Takeshita, C.; Takakura, N., Tumor vessel maturation by apelin/APJ system improves the efficiency of immunotherapy. *Eur J Cancer* 2013, 49, S128-S128.

[34] Diakowska, D.; Markocka-Maczka, K.; Szelachowski, P.; Grabowski, K., Serum Levels of Resistin, Adiponectin, and Apelin in Gastroesophageal Cancer Patients. *Dis Markers* 2014, Article ID 619649.

[35] Muto, J.; Shirabe, K.; Yoshizumi, T.; Ikegami, T.; Aishima, S.; Ishigami, K.; Yonemitsu, Y.; Ikeda, T.; Soejima, Y.; Maehara, Y., The Apelin-APJ System Induces Tumor Arteriogenesis in Hepatocellular Carcinoma. *Anticancer Res* 2014, 34(10), 5313-5320.

[36] Picault, F. X.; Chaves-Almagro, C.; Projetti, F.; Prats, H.; Masri, B.; Audigier, Y., Tumour co-expression of apelin and its receptor is the basis of an autocrine loop involved in the growth of colon adenocarcinomas. *Eur J Cancer* 2014, 50(3), 663-674.

[37] Atinkaya, S. O.; Nergiz, S.; Kucuk, M.; Yuksel, H., Apelin levels are higher in obese patients with endometrial cancer. *J Obstet Gynaecol Re* 2015, 41(2), 294-300.

[38] Lacquaniti, A.; Altavilla, G.; Picone, A.; Donato, V.; Chirico, V.; Mondello, P.; Aloisi, C.; Marabello, A.; Loddo, S.; Buemi, A.; Lorenzano, G.; Buemi, M., Apelin beyond kidney failure and hyponatremia: a useful biomarker for cancer disease progression evaluation. *Clin Exp Med* 2015, 15(1), 97-105.

[39] Wan, Y. P.; Zeng, Z. C.; Xi, M.; Wan, S.; Hua, W.; Liu, Y. L.; Zhou, Y. L.; Luo, H. W.; Jiang, F. N.; Zhong, W. D., Dysreguated microRNA-224/apelin axis associated with aggressive progression and poor prognosis in patients with prostate cancer. *Hum Pathol* 2015, 4 (2), 295-303.

[40] Devapatla, B. K.; Jaiprasart, P.; Dogra, S.; Ha, J. H.; Woo, S., Apelin/Apj pathway for targeting ovarian tumor microenvironment. *Cancer Res* 2016, 76.

[41] Ermin, S.; Cok, G.; Veral, A.; Kose, T., The role of apelin in the assessment of response to chemotherapy and prognosis in stage 4 nonsmall cell lung cancer. *Turk J Med Sci* 2016, 46(5), 1353-1359.

[42] Feng, M. Y.; Yao, G. D.; Yu, H. W.; Qing, Y.; Wang, K. A., Tumor apelin, not serum apelin, is associated with the clinical features and prognosis of gastric cancer. *Bmc Cancer* 2016, 16(1), 794.

[43] Hall, C.; Ehrlich, L.; White, T.; O'Brien, A.; Lairmore, T. C.; Alpini, G.; Glaser, S., Activation of the Apelin double right arrow Apelin Receptor Axis in Cholangiocarcinoma Promotes Tumor Growth and Angiogenesis. *Gastroenterology* 2016, 150 (4), S1124-S1124.

[44] Kim, H. S.; Kim, J. W., Paradoxical expressions of hypoxia-inducible factor-1 alpha and apelin affecting cervical carcinogenesis and prognosis. *Journal of Clinical Oncology* 2016 34:15_suppl, e17006-e17006.

[45] Salman, T.; Demir, L.; Varol, U.; Akyol, M.; Oflazoglu, U.; Yildiz, Y.; Taskaynatan, H.; Cengiz, H.; Guvendi, G.; Kucukzeybek, Y.; Alacacioglu, A.; Tarhan, O., Serum apelin levels and body composition changes in breast cancer patients treated with an aromatase inhibitor. *J Buon* 2016, 21(6), 1419-1424.

[46] Yang, Y. J.; Lv, S. Y.; Ye, W. L.; Zhang, L., Apelin/APJ system and cancer. *Clin Chim Acta* 2016, 457, 112-116.

[47] Zhang, L.; Takara, K.; Yamakawa, D.; Kidoya, H.; Takakura, N., Apelin as a marker for monitoring the tumor vessel normalization window during antiangiogenic therapy. *Cancer Sci* 2016, 107(1), 36-44.

[48] Hall, C.; Ehrlich, L.; Venter, J.; O'Brien, A.; White, T.; Zhou, T. H.; Dang, T.; Meng, F. Y.; Invernizzi, P.; Bernuzzi, F.; Alpini, G.; Lairmore, T. C.; Glaser, S., Inhibition of the apelin/apelin receptor axis decreases cholangiocarcinoma growth. *Cancer Lett,* 2017, 386, 179-188.

[49] Hao, Y. Z.; Li, M. L.; Ning, F. L.; Wang, X. W., APJ Is Associated with Treatment Response in Gastric Cancer Patients Receiving Concurrent Chemoradiotherapy and Endostar Therapy. *Cancer Biother Radio* 2017, 32(4), 133-138.

[50] Hoffmann, M.; Fiedor, E.; Ptak, A., Bisphenol A and its derivatives tetrabromobisphenol A and tetrachlorobisphenol A induce apelin expression and secretion in ovarian cancer cells through a peroxisome proliferator-activated receptor gamma-dependent mechanism. *Toxicol Lett* 2017, 269, 15-22.

[51] Ni, Y. Y.; Liu, D.; Ge, G.; Zhu, Y. H.; Zhang, L., Apelin is a novel circulating biomarker for the diagnosis of lung cancer. *Int J Clin Exp Patho* 2017, 10(5), 5559-5565.

[52] Zhang, H. P.; Zou, J.; Xu, Z. Q.; Ruan, J.; Yang, S. D.; Yin, Y.; Mu, H. J., Association of leptin, visfatin, apelin, resistin and adiponectin with clear cell renal cell carcinoma. *Oncol Lett* 2017, 13(1), 463-468.

[53] Zuurbier, L.; Rahman, A.; Cordes, M.; Scheick, J.; Wong, T. J.; Rustenburg, F.; Joseph, J. C.; Dynoodt, P.; Casey, R.; Drillenburg, P.; Gerhards, M.; Barat, A.; Klinger, R.; Fender, B.; O'Connor, D. P.; Betge, J.; Ebert, M. P.; Gaiser, T.; Prehn, J. H. M.; Griffioen, A. W.; van Grieken, N. C. T.; Ylstra, B.; Byrne, A. T.; van der Flier, L. G.; Gallagher, W. M.; Postel, R., Apelin: A putative novel predictive biomarker for bevacizumab response in colorectal cancer. *Oncotarget* 2017, 8(26), 42949-42961.

[54] Lee, D. K.; Saldivia, V. R.; Nguyen, T.; Cheng, R.; George, S. R.; O'Dowd, B. F., Modification of the terminal residue of apelin-13 antagonizes its hypotensive action. *Endocrinology* 2005, 146(1), 231-236.

[55] Maloney, P. R.; Khan, P.; Hedrick, M.; Gosalia, P.; Milewski, M.; Li, L.; Roth, G. P.; Sergienko, E.; Suyama, E.; Sugarman, E.; Nguyen, K.; Mehta, A.; Vasile, S.; Su, Y.; Stonich, D.; Nguyen, H.; Zeng, F. Y.; Novo, A. M.; Vicchiarelli, M.; Diwan, J.; Chung, T. D. Y.; Pinkerton, A. B.; Smith, L. H., Functional antagonists of the Apelin (APJ) receptor. *In Probe Reports from the NIH Molecular Libraries Program*, Bethesda (Md.), 2010.

[56] Masri, B.; Barak, L. S.; Bai, Y.; Knibieher, B.; Caron, M. G.; Audigier, Y., Identification and pharmacological properties of an antagonist of apelin receptors. *Regul Peptides* 2010, 164(1), 26-26.

[57] Macaluso, N. J.; Pitkin, S. L.; Maguire, J. J.; Davenport, A. P.; Glen, R. C., Discovery of a competitive apelin receptor (APJ) antagonist. *ChemMedChem* 2011, 6 (6), 1017-23.

[58] Maloney, P. R.; Khan, P.; Hedrick, M.; Gosalia, P.; Milewski, M.; Li, L.; Roth, G. P.; Sergienko, E.; Suyama, E.; Sugarman, E.; Nguyen, K.; Mehta, A.; Vasile, S.; Su, Y.; Stonich, D.; Nguyen, H.; Zeng, F. Y.; Novo, A. M.; Vicchiarelli, M.; Diwan, J.; Chung, T. D.; Smith, L. H.; Pinkerton, A. B., Discovery of 4-oxo-6-((pyrimidin-2-ythio)methyl)-4H-pyran-3-yl 4-nitrobenzoate (ML221) as a functional antagonist of the apelin (APJ) receptor. *Bioorganic & medicinal chemistry letters* 2012, 22(21), 6656-60.

[59] Le Gonidec, S.; Chaves-Almagro, C.; Bai, Y.; Kang, H. J.; Smith, A.; Wanecq, E.; Huang, X. P.; Prats, H.; Knibiehler, B.; Roth, B. L.; Barak, L. S.; Caron, M. G.; Valet, P.; Audigier, Y.; Masri, B., Protamine is an antagonist of apelin receptor, and its activity is reversed by heparin. *Faseb J* 2017, 31(6), 2507-2519.

[60] Harford-Wright E., Andre-Gregoire G., Jacobs K. A., Treps L., Le Gonidec S., Lecair H. M., Gonzalez-Diest S., Roux Q., Guillonneau F., Loussouarn D., Oliver L., Vallette F. M., Foufelle F., Valet P., Davenport A. P., Glen R. C., Bidere N., Gavard J. Pharmacological targeting of apelin impairs glioblastoma growth. *Brain,* 2017, 140 (11), 2939-2954.

[61] Neubig et al., International Union of Pharmacology Committee on Receptor Nomenclature and Drug Classification. XXXVIII. Update on Terms and Symbols in Quantitative Pharmacology. *Pharmacol Rev.* 2003, 55, 597-606.

---

The invention claimed is:

1. A linear compound comprising the sequence of Formula I:

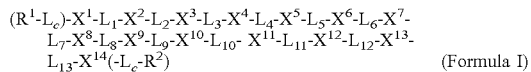

(Formula I)

wherein:

$X^1$ is any amino acid;
$X^2$ is selected from the group consisting of R, H, and K;
$X^3$ is P;
$X^4$ is R;
$X^5$ is selected from the group consisting of Nle, L, A, V, I, M, F, Y, and W;
$X^6$ is selected from the group consisting of Abu, C, A, V, I, L, M, F, Y, W, and P;
$X^7$ is selected from the group consisting of H, K, A, V, I, L, M, F, Y, W, and R;
$X^8$ is selected from the group consisting of K, H, A, V, I, L, M, F, Y, W, and R;
$X^9$ is selected from the group consisting of Abu, C, A, V, I, L, M, F, Y, W, and P;
$X^{10}$ is selected from the group consisting of R, H, and K;
$X^{11}$ is selected from the group consisting of Aib, and P;
$X^{12}$ is selected from the group consisting of R, H, and K;
$X^{13}$ is selected from the group consisting of Nle, Aib, L, V, I, and A;
$X^{14}$ is absent or is selected from the group consisting of C, F, other hydrophobic amino acids, 3,4,5-trifluorophenylalanine (Tfpa or (3,4,5-trifluoro)F), β-cyclohexylalanine (Cha), Naphthylalanine (Nal), 4-chlorophenylalanine (4cpa), 4-methoxyphenylalanine, 4-methylphenylalanine, 4-pyridylealanine, 3-pyridylalanine, 2-pyridylalanine, D-(-)-α-phenylglycine, homophenylalanine, 3-styrylalanine, O-benzyl-L-tyrosine, 4-benzoyl-L-phenylalanine, α-methyl-L-phenylalanine, α-methyl-D-phenylalanine or aminoindane, 2-aminoindane, O-benzyltyrosine, and 4-Aminopiperidine-4-carboxylic acid;

wherein:
1) for $X^1$ to $X^{14}$ any natural amino acid listed may independently be optionally modified, and wherein 2) for $X^1$ to $X^{14}$ any modified amino acid listed may independently be optionally further modified and, in options 1) and 2), the modification in option 1) and the further modification in option 2) is optionally alkylation, esterification, N-alkyl amidation, substitution of hydrogen with any halo group or hydroxyl group or conjugation to an $R^3$ moiety through a conjugation linker $L_c$;

each of $L_1$ to $L_{13}$ is independently a linkage appropriate for joining two amino acids together;

$R^1$, $R^2$, and $R^3$ are independently absent or are independently selected from the group consisting of a peptide moiety, an acetyl moiety, a formyl moiety, a propinyl moiety, a biotin moiety, a myristoyl moiety, a palmitoyl moiety, a methyl moiety, a saturated or unsaturated fatty acyl moiety, a polyethylene glycol polymer moiety, an immunoglobulin moiety, an immunoglobulin Fc domain moiety, an albumin moiety, a methylated moiety, an esterified moiety, and a portion of the natural apelin compound;

each $L_c$ is independently absent or is a conjugation linker which joins $R^1$ to $X^1$, $R^2$ to $X^{14}$, or an $R^3$ moiety to any of $X^1$ to $X^{14}$ and is selected from any linkage appropriate for joining $R^1$ to $X^1$, $R^2$ to $X^{14}$ or an $R^3$ moiety to any of $X^1$ to $X^{14}$;

or a pharmaceutically acceptable salt, solvate, amide, ester, prodrug, or deuterated analogue thereof.

2. The compound of claim 1 or a pharmaceutically acceptable salt, solvate, amide, ester, prodrug, or deuterated analogue thereof, wherein:

$X^1$ is selected from the group consisting of V, I, L, M, P, Y, W, C, Q, Glp, and A;
$X^2$ is R;
$X^3$ is P;
$X^4$ is R;
$X^5$ is selected from the group consisting of A, V, I, Nle, and L;
$X^6$ is selected from the group consisting of Abu, M, P, and C;
$X^7$ is selected from the group consisting of H, R, and K;
$X^8$ is selected from the group consisting of R, K, and H;
$X^9$ is selected from the group consisting of Abu, M, P, and C;
$X^{10}$ is R, or K;
$X^{11}$ is selected from the group consisting of Aib, and P;
$X^{12}$ is R, K, or H;
$X^{13}$ is selected from the group consisting of A, V, I, Nle, and L;
$X^{14}$ is absent or is selected from the group consisting of C, F, other hydrophobic amino acids, 3,4,5-trifluorophenylalanine (Tfpa or (3,4,5-trifluoro)F), β-cyclohexylalanine (Cha), Naphthylalanine (Nal), 4-chlorophenylalanine (4cpa), 4-methoxyphenylalanine, 4-methylphenylalanine, 4-pyridylealanine, 3-pyridylalanine, 2-pyridylalanine, D-(-)-α-phenylglycine, homophenylalanine, 3-styrylalanine, O-benzyl-L-tyrosine, 4-benzoyl-L-phenylalanine, α-methyl-L-phenylalanine, α-methyl-D-phenylalanine or aminoindane, 2-aminoindane; O-benzyltyrosine, or 4-Aminopiperidine-4-carboxylic acid;

wherein:
1) for $X^1$ to $X^{14}$ any natural amino acid listed may independently be optionally modified, and wherein 2) for $X^1$ to $X^{14}$ any modified amino acid listed may independently be optionally further modified and, in options 1) and 2), the modification in option 1) and the further modification in option 2) is optionally alkylation, esterification, N-alkyl amidation, substitution of hydrogen with any halo group or hydroxyl group or conjugation to an $R^3$ moiety through a conjugation linker $L_c$;

each of $L_1$ to $L_{13}$ is independently a linkage appropriate for joining two amino acids together;

$R^1$, $R^2$, and $R^3$ are independently absent or are independently selected from the group consisting of a peptide moiety, an acetyl moiety, a formyl moiety, a propinyl moiety, a biotin moiety, a myristoyl moiety, a palmitoyl moiety, a methyl moiety, a saturated or unsaturated fatty acyl moiety, a polyethylene glycol polymer moiety, an immunoglobulin moiety, an immunoglobulin Fc domain moiety, an albumin moiety, a methylated moiety, an esterified moiety, and a portion of the natural apelin compound;

each $L_c$ is independently absent or is a conjugation linker which joins $R^1$ to $X^1$, $R^2$ to $X^{14}$, or an $R^3$ moiety to any of $X^1$ to $X^{14}$ and is selected from any linkage appropriate for joining $R^1$ to $X^1$, $R^2$ to $X^{14}$ or an $R^3$ moiety to any of $X^1$ to $X^{14}$.

3. The compound of claim 1 or a pharmaceutically acceptable salt, solvate, amide, ester, prodrug, or deuterated analogue thereof, wherein:
(i) $X^1$ is C, Q, Glp, or A;
(ii) $X^2$ is R;
(iii) $X^3$ is P;
(iv) $X^4$ is R;
(v) $X^2$ is R and said R is modified by methylation;
(vi) $X^4$ is R and said R is modified by methylation;
(vii) $X^5$ is selected from the group consisting of Ne and L;
(viii) $X^{13}$ is selected from the group consisting of Ne and L;
(ix) $X^6$ is selected from the group consisting of C and Abu;
(x) $X^9$ is independently selected from the group consisting of C and Abu;
(xi) $X^7$ is K and $X^3$ is H, or wherein $X^7$ is H and $X^3$ is K, or wherein $X^7$ is A and $X^3$ is K, or wherein $X^7$ is K and $X^8$ is A;
(xii) $X^7$ and $X^8$ is H and the other is K;
(xiii) $X^{10}$ is R;
(xiv) $X^{10}$ and $X^{12}$ is R;
(xv) $X^{11}$ is selected from the group consisting of P and Aib;
(xvi) $X^{14}$ is selected from C and (3,4,5-trifluoro-)F; or
(xvii) any combination of (i) to (xvi).

4. The compound of claim 1 or a pharmaceutically acceptable salt, solvate, amide, ester, prodrug, or deuterated analogue thereof, wherein
(i) $X^1$ is C, optionally wherein $R^1$ is myristoyl;
(ii) $X^5$ is Nle;
(iii) $X^6$ is Abu;
(iv) $X^7$ is K and $X^8$ is H;
(v) $X^9$ is Abu;
(vi) $X^{10}$ is R;
(vii) $X^{11}$ is Aib;
(viii) $X^{12}$ is R;
(ix) $X^{13}$ is Nle;
(x) $X^{14}$ is (3,4,5-triflioro)F; or
(xi) any combination of (i)-(x).

5. The compound of claim 1, or a pharmaceutically acceptable salt, solvate, amide, ester, prodrug, or deuterated analogue thereof, wherein $X^{14}$ is selected from the group consisting of Alanine (A), Isoleucine (I), Leucine (L), Methionine (M), Tyrosine (Y), Tryptophan (W), Valine (V), Proline (P), and Glycine (G).

6. The compound of claim 1, or a pharmaceutically acceptable salt, solvate, amide, ester, prodrug, or deuterated analogue thereof, wherein each of $L_1$ to $L_{13}$ is independently an amide bond, N-methylated amide, urea, ester, carbamate, peptoid, sulphonamide, alkene, thioamide, thioether, fluoroalkene, azapeptide difluoroketone or epoxide.

7. The compound of claim 1 or a pharmaceutically acceptable salt, solvate, amide, ester, prodrug, or deuterated analogue thereof, wherein $X^{14}$ is (3,4,5-trifluoro-)F.

8. The compound of claim 1, wherein the compound is selected from the group consisting of: MM107, MM108, MM193, MM262, MM297-MM302, MM312-MM316, MM412-MM424, MM426 and MM428, and pharmaceutically acceptable salts, solvates, amides, esters, prodrugs, and deuterated analogues thereof.

9. The compound of claim 1, wherein the compound is selected from the group consisting of: MM107, MM108, MM193, MM262, MM297-MM302, MM312-MM316, MM412-MM424, MM426 and MM428, and pharmaceutically acceptable salts thereof.

10. A pharmaceutical composition comprising the compound of claim 1 or a pharmaceutically acceptable salt, solvate, amide, ester, prodrug, or deuterated analogue thereof and a pharmaceutically acceptable diluent, excipient, or carrier.

* * * * *